United States Patent
Burke et al.

(10) Patent No.: US 9,732,102 B2
(45) Date of Patent: *Aug. 15, 2017

(54) SYSTEM FOR CONTROLLING THE REACTIVITY OF BORONIC ACIDS

(71) Applicant: The Board of Trustees of the University of Illinois, Urbana, IL (US)

(72) Inventors: Martin D. Burke, Champaign, IL (US); Eric P. Gillis, Wallingford, CT (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/144,153

(22) Filed: May 2, 2016

(65) Prior Publication Data

US 2017/0002026 A1    Jan. 5, 2017

Related U.S. Application Data

(60) Continuation of application No. 13/654,820, filed on Oct. 18, 2012, now Pat. No. 9,328,127, which is a division of application No. 13/190,223, filed on Jul. 25, 2011, now Pat. No. 8,318,983, which is a division of application No. 11/937,338, filed on Nov. 8, 2007, now Pat. No. 8,013,203.

(60) Provisional application No. 60/951,405, filed on Jul. 23, 2007.

(51) Int. Cl.
| | | |
|---|---|---|
| C07F 5/02 | (2006.01) |
| C07F 9/02 | (2006.01) |
| C07C 45/68 | (2006.01) |
| C07C 51/353 | (2006.01) |
| C07C 67/343 | (2006.01) |
| C07D 213/55 | (2006.01) |
| C07D 307/81 | (2006.01) |
| C07F 5/04 | (2006.01) |

(52) U.S. Cl.
CPC ............. *C07F 5/025* (2013.01); *C07C 45/68* (2013.01); *C07C 51/353* (2013.01); *C07C 67/343* (2013.01); *C07D 213/55* (2013.01); *C07D 307/81* (2013.01); *C07F 5/02* (2013.01); *C07F 5/04* (2013.01); *Y02P 20/55* (2015.11)

(58) Field of Classification Search
CPC ............. C07F 5/025; C07F 5/02; C07F 9/02
USPC .................... 568/6; 560/126; 562/7
See application file for complete search history.

(56) References Cited

U.S. PATENT DOCUMENTS 8,318,983 B2 * 11/2012 Burke ................ C07F 5/02
560/126

OTHER PUBLICATIONS

Gillis et al. JACS, 2007,129, 6716-6117.*

* cited by examiner

*Primary Examiner* — Yevegeny Valenrod
(74) *Attorney, Agent, or Firm* — Dana M. Gordon; Foley Hoag LLP

(57) ABSTRACT

A protected organoboronic acid includes a boron having an $sp^3$ hybridization, a conformationally rigid protecting group bonded to the boron, and an organic group bonded to the boron through a boron-carbon bond. A method of performing a chemical reaction includes contacting a protected organoboronic acid with a reagent, the protected organoboronic acid including a boron having an $sp^3$ hybridization, a conformationally rigid protecting group bonded to the boron, and an organic group bonded to the boron through a boron-carbon bond. The organic group is chemically transformed, and the boron is not chemically transformed.

19 Claims, 21 Drawing Sheets

| Entry | R | conc. M | Base | Solvent | Temp°C | Isolated yield |
|---|---|---|---|---|---|---|
| 1 | MeO-C6H4- (3-) | 0.08 | NaOH | THF:H2O 5:1 | 60 | 97% |
| 2 | MeO-C6H4- (3-) | 0.33 | NaOH | THF:H2O 5:1 | 60 | 96% |
| 3 | 4-pyridyl | 0.08 | K2CO3 | dioxane:H2O 5:1 | 100 | 95% |
| 4 | 4-pyridyl | 0.33 | K2CO3 | dioxane:H2O 5:1 | 100 | 96% |

SYSTEM FOR CONTROLLING THE REACTIVITY OF BORONIC ACIDS

REFERENCE TO RELATED APPLICATIONS

This application is a continuation of U.S. patent application Ser. No. 13/654,820, filed Oct. 18, 2012, now U.S. Pat. No. 9,328,127, which is a divisional of U.S. patent application Ser. No. 13/190,223, filed Jul. 25, 2011, now U.S. Pat. No. 8,318,983, which is a divisional of U.S. patent application Ser. No. 11/937,338, filed Nov. 8, 2007, now U.S. Pat. No. 8,013,203, which claims the benefit of U.S. Provisional Patent Application No. 60/951,405 entitled "System for Controlling the Reactivity of Boronic Acids" filed Jul. 23, 2007.

BACKGROUND

The Suzuki-Miyaura reaction is a palladium- or nickel-catalyzed cross coupling between a boronic acid or a boronic ester and an organohalide or an organo-pseudohalide. (Miyaura, A. *Chem. Rev.*, 1995) This cross coupling transformation is a powerful method for C—C bond formation in complex molecule synthesis. The reaction is tolerant of functional groups, and has become increasingly general and widespread in its use for coupling of organic compounds. (Barder, 2005; Billingsley, 2007; Littke, 2000; Nicolaou, 2005).

Boronic acids are notoriously sensitive to many common reagents. (Hall, 2005; Tyrell, 2003) It is therefore typical to introduce the boronic acid functional group during the last step of a building block synthesis. However, many of the methods for doing so (hydroboration, trapping organometallic reagents with trimethylborate, etc.) are intolerant to a variety of common functional groups, such as alcohols, aldehydes, ketones, alkynes and olefins. This makes the synthesis of structurally complex boronic acid building blocks quite challenging. In contrast, organostannanes are remarkably tolerant to a wide variety of reaction conditions and are routinely carried through multiple steps en route to structurally complex coupling partners. As a result, organostannanes have found widespread use in complex molecule synthesis (De Souza, M. V. N., 2006; Pattenden, G., 2002; Hong, B.-C., 2006) despite their well-known drawbacks including toxicity, high molecular weight, and byproducts that are difficult to remove. The ability to similarly carry protected boronic acids through multi-step synthetic sequences could substantially heighten their utility and broaden the scope of their applicability.

One area of research on the Suzuki-Miyaura reaction is the development of protecting groups for the boronic acid functional group. A compound that includes a protected boronic acid and another functional group can undergo chemical transformations of the other functional group without chemically transforming the boron. Removal of the protecting group (deprotection) then provides the free boronic acid, which can undergo a Suzuki-Miyaura reaction to cross-couple the compound with an organohalide or an organo-pseudohalide.

In one example of a boronic acid protecting group, each of the two B—OH groups is converted into a boronic ester group (>B—O—R) or a boronic amide group (>B—NH—R), where R is an organic group. The organic group can be removed by hydrolysis to provide the free boronic acid. Current data suggest that transmetalation between boronic acids and Pd(II) requires formation of an electronically-activated anionic boron 'ate' complex and/or a hydroxo $\mu_2$-bridged organoboronate-Pd(II) intermediate. Both mechanisms require a vacant boron p-orbital that is Lewis acidic. Bidentate ligands that contain strongly electron-donating heteroatoms are known to inhibit the cross-coupling of organoboron compounds, presumably by reducing the Lewis acidity of the $sp^2$-hybridized boron center. Harnessing this effect, a few selective cross-couplings with boron-protected organoboranes that contain halogens have been reported recently. (Deng, 2002; Hohn, 2004; Holmes, 2006; Noguchi, 2007) Examples of protecting groups used in these selective reactions include pinacol esters (boronic ester) and 1,8-diaminonaphthalene (boronic amide). The heteroatom-boron bonds in these protected compounds tend to be very strong, however. The relatively harsh conditions required for cleaving these ligands typically are incompatible with complex molecule synthesis.

In another example of a protected boronic acid, the boron containing compound is converted into a tetracoordinate anion, such as $[R—BF_3]^-$, where R represents an organic group. Compounds containing these protecting groups are present as salts with a counterion, such as $K^+$ or $Na^+$. These anionic compounds are reported to be effective for inhibiting the reaction of boron during chemical transformations such as nucleophilic substitution, 1,3-dipolar cycloaddition, metal-halogen exchange, oxidation, epoxidation, dihydroxylation, carbonylation, and alkenation (Wittig or Horner-Wadsworth-Emmons reactions). (Molander, 2007) The boron itself is not protected from the Suzuki-Miyaura reaction, but can be used directly in the coupling transformation. Another class of tetracoordinate boron anions, $[R—B(OH)_3]^-$, has been reported in the context of purifying boronic acids for use in the Suzuki-Miyaura reaction. (Cammidge, 2006) As with the trifluoroboronate anion, the trihydroxyboronate anion is reactive in the Suzuki-Miyaura reaction.

These typical protection strategies for boronic acids each have some disadvantages. Boronic esters and boronic amides can protect the boron from a wide variety of reaction conditions, including Suzuki-Miyaura reaction conditions. However, the harsh conditions required for deprotection of boronic esters and boronic amides can cause undesirable side reactions with other functional groups. Trifluoroboronate anions also are unreactive in a wide variety of reaction conditions. However, this protection strategy does not allow for selective Suzuki-Miyaura reactions, since both protected and unprotected boron atoms will be eliminated in the coupling transformation.

It would be desirable to protect boronic acid groups in a wide variety of synthetic reactions, including the Suzuki-Miyaura reaction. Ideally, protected boronic acids would undergo deprotection under mild conditions with high yields. Such a system for controlling the reactivity of boronic acids could greatly expand the versatility of the Suzuki-Miyaura reaction or of other reactions of boronic acids.

SUMMARY

In one aspect, the invention provides a protected organoboronic acid including a boronate group and an organic group. The boronate group includes a boron having an $sp^3$ hybridization and a conformationally rigid protecting group bonded to the boron. The organic group is bonded to the boron through a boron-carbon bond. The organic group is not selected from the group consisting of —$CH_2H_5$, —$C(CH_3)_2H(CH_3)_2$, cyclopentyl, tetrahydropyranyl, norbornyl, 2,4,4-trimethyl-bicyclo[3.1.1]heptanyl, —$C_6H_5$, —C₆H₄—CH₃, —C₆H₄—CHO, —C₆H₄—OCH₃, —C₆H₄—F, —C₆H₄—Cl, —C₆H₄—Br, —C₆H₄—CF₃, and —C₆H₄—NO₂.

In another aspect, the invention provides a protected organoboronic acid, selected from the group consisting of protected organoboronic acids 8d, 8e, 8f, 8e, 9a, 9b, 9c, 9d, 9e, 9f, 13, 14, 16, 17, 19, 20, 21, 22, 23, 24, 25, 26, 27, 30, 54a, 54b, 54c, 54d, 61, 64, 66, 68, 70, 72, 74, 75, 80, 84, 91, 94, 302, and 306.

In yet another aspect, the invention provides a method of performing a chemical reaction, including contacting a protected organoboronic acid with a reagent, the protected organoboronic acid including a boronate group and an organic group. The boronate group includes a boron having an sp³ hybridization and a conformationally rigid protecting group bonded to the boron. The organic group is bonded to the boron through a boron-carbon bond. The organic group is chemically transformed, and the boron is not chemically transformed.

In yet another aspect, the invention provides a method of performing a chemical reaction, including contacting a protected organoboronic acid and an organohalide with a palladium catalyst, in the presence of aqueous base, to provide a cross-coupled product. The protected organoboronic acid including a boronate group and an organic group. The boronate group includes a boron having an sp³ hybridization and a conformationally rigid protecting group bonded to the boron. The organic group is bonded to the boron through a boron-carbon bond.

In yet another aspect, the invention provides a method of forming a protected organoboronic acid, including reacting a compound represented by formula (I)

R¹—B(OH)₂     (I);

with a protecting reagent. The compound represented by formula (I) may be formed in situ.

In yet another aspect, the invention provides a method of forming a protected organoboronic acid, including reacting a compound represented by formula (XII)

with a N-substituted imino-di-carboxylic acid. The compound represented by formula (XII) may be formed in situ.

In yet another aspect, the invention provides a method of forming a protected organoboronic acid, including reacting a compound represented by formula (XIII)

R¹⁰—BX₂     (XIII);

with a protecting reagent. The protecting reagent may include N-methyliminodiacetic acid.

The following definitions are included to provide a clear and consistent understanding of the specification and claims.

The term "organoboronic acid" means a compound represented by formula (I):

R¹—B(OH)₂     (I), where R¹ is an organic group that is bonded to the boron through a boron-carbon bond.

The term "group" means a linked collection of atoms or a single atom within a molecular entity, where a molecular entity is any constitutionally or isotopically distinct atom, molecule, ion, ion pair, radical, radical ion, complex, conformer etc., identifiable as a separately distinguishable entity. The description of a group as being "formed by" a particular chemical transformation does not imply that this chemical transformation is involved in making the molecular entity that includes the group.

The term "organic group" means a group containing at least one carbon atom.

The term "protected organoboronic acid" means a chemical transform of an organoboronic acid, in which the boron has a lower chemical reactivity relative to the original organoboronic add.

The term "chemical transform" of a substance means a product of a chemical transformation of the substance, where the product has a chemical structure different from that of the substance.

The term "chemical transformation" means the conversion of a substance into a product, irrespective of reagents or mechanisms involved.

The term "sp³ hybridization" means that an atom is bonded and/or coordinated in a configuration having a tetrahedral character of at least 50%. For tetracoordinate boron atoms, the tetrahedral character of the boron atom is calculated by the method of Hopfl, H., *J. Organomet. Chem.* 581, 129-149, 1999. In this method, the tetrahedral character is defined as:

THC$_{DA}$[%]=100×[1−(Σ$_{n=1-6}$|109.5−θ$_n$|°/90°)]

where θ$_n$ is one of the six bond angles of the boron atom.

The term "protecting group" means an organic group bonded to at least one atom, where the atom has a lower chemical activity than when it is not bonded to the protecting group. For boron containing compounds, the term excludes non-organic groups used to lower the chemical activity of the boron, such as the F⁻ and OH⁻ ligands of —BF₃⁻ and —B(OH)₃⁻.

The term "conformationally rigid protecting group" means an organic protecting group that, when bonded to a boron atom, is determined to be conformationally rigid by the "conformational rigidity test".

The term "alkyl group" means a group formed by removing a hydrogen from a carbon of an alkane, where an alkane is an acyclic or cyclic compound consisting entirely of hydrogen atoms and saturated carbon atoms. An alkyl group may include one or more substituent groups.

The term "heteroalkyl group" means a group formed by removing a hydrogen from a carbon of a heteroalkane, where a heteroalkane is an acyclic or cyclic compound consisting entirely of hydrogen atoms, saturated carbon atoms, and one or more heteroatoms. A heteroalkyl group may include one or more substituent groups.

The term "alkenyl group" means a group formed by removing a hydrogen from a carbon of an alkene, where an alkene is an acyclic or cyclic compound consisting entirely of hydrogen atoms and carbon atoms, and including at least one carbon-carbon double bond. An alkenyl group may include one or more substituent groups.

The term "heteroalkenyl group" means a group formed by removing a hydrogen from a carbon of a heteroalkene, where a heteroalkene is an acyclic or cyclic compound consisting entirely of hydrogen atoms, carbon atoms and one or more heteroatoms, and including at least one carbon-carbon double bond. A heteroalkenyl group may include one or more substituent groups.

The term "alkynyl group" means a group formed by removing a hydrogen from a carbon of an alkyne, where an alkyne is an acyclic or cyclic compound consisting entirely of hydrogen atoms and carbon atoms, and including at least one carbon-carbon triple bond. An alkynyl group may include one or more substituent groups.

The term "heteroalkynyl group" means a group formed by removing a hydrogen from a carbon of a heteroalkyne, where a heteroalkyne is an acyclic or cyclic compound consisting entirely of hydrogen atoms, carbon atoms and one or more heteroatoms, and including at least one carbon-carbon triple bond. A heteroalkynyl group may include one or more substituent groups.

The term "aryl group" means a group formed by removing a hydrogen from a ring carbon atom of an aromatic hydrocarbon. An aryl group may by monocyclic or polycyclic and may include one or more substituent groups.

The term "heteroaryl group" means a group formed by replacing one or more methine (—C=) and/or vinylene (—CH=CH—) groups in an aryl group with a trivalent or divalent heteroatom, respectively. A heteroaryl group may by monocyclic or polycyclic and may include one or more substituent groups.

The term "substituent group" means a group that replaces one or more hydrogen atoms in a molecular entity.

The term "halogen group" means —F, —Cl, —Br or —I.

The term "organohalide" means an organic compound that includes at least one halogen group.

The term "haloorganoboronic acid" means an organoboronic acid in which the organic group bonded to the boron through a boron-carbon bond includes a halogen group or a pseudohalogen group.

The term "pseudohalogen group" means a group that has chemical reactivity similar to that of a halogen group. Examples of pseudohalogen groups include triflate (—O—S(=O)$_2$—CF$_3$), methanesulfonate (—O—S(=O)$_2$—CH$_3$), cyanate (—C≡N), azide (—N$_3$) thiocyanate (—N=C=S), thioether (—S—R), anhydride (—C(=O)—O—C(=O)—R), and phenyl selenide (—Se—C$_6$H$_5$).

The term "organo-pseudohalide" means an organic compound that includes at least one pseudohalogen group.

BRIEF DESCRIPTION OF THE DRAWINGS

The invention can be better understood with reference to the following drawings and description. The components in the figures are not necessarily to scale, emphasis instead being placed upon illustrating the principles of the invention.

DETAILED DESCRIPTION

The present invention makes use of the discovery that organoboronic acids can be protected from a variety of chemical reactions by transformation into a protected organoboronic acid that includes a boron having an sp$^3$ hybridization and a conformationally rigid protecting group bonded to the boron. A protected organoboronic acid including a boron having sp$^3$ hybridization and a conformationally rigid protecting group bonded to the boron may be protected from cross-coupling with an organohalide or an organopseudohalide through the Suzuki-Miyaura transformation. Moreover, the protected organoboronic acid may be deprotected under mild reaction conditions with high yields, to provide the free organoboronic acid.

A protected organoboronic acid includes a boron having an sp³ hybridization, a conformationally rigid protecting group bonded to the boron, and an organic group. The organic group is bonded to the boron through a boron-carbon (B—C) bond. The protecting group may be a trivalent group. Preferably, the organic group can undergo a chemical transformation without chemically transforming the boron.

Figure 1:
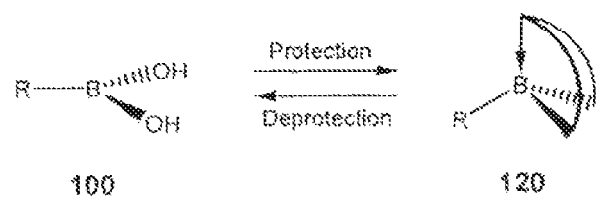
FIG. 1 represents a method of forming a protected organoboronic acid.

FIG. 1 represents a method of forming a protected organoboronic acid, where organoboronic acid 100, having an sp² hybridization, undergoes a protection transformation to form protected organoboronic acid 120, having an sp³ hybridization. As shown in FIG. 1, the protected organoboronic acid 120 can undergo a deprotection transformation to form organoboronic acid 100, which includes a free boronic acid group. In contrast to a protected organoboronic acid that includes a boron having an sp³ hybridization and a conformationally rigid protecting group bonded to the boron, conventional protected organoboronic acids include either a boron having an sp² hybridization, a boron present in an anionic compound, or a boron bonded to a protecting group that is not conformationally rigid.

In one example, a protected organoboronic acid may be represented by formula (II):

$$R^1-B-T \qquad (II),$$

where $R^1$ represents an organic group bonded to the boron through a B—C bond, B represents a boron having sp³ hybridization, and T represents a conformationally rigid protecting group. The $R^1$ group may be an alkyl group, a heteroalkyl group, an alkenyl group, a heteroalkenyl group, an alkynyl group, a heteroalkynyl group, an aryl group, a heteroaryl group, or a combination of at least two of these groups. Moreover, $R^1$ may include one or more substituent groups, which may include a heteroatom bonded to a carbon of the alkyl, heteroalkyl, alkenyl, heteroalkenyl, alkynyl, heteroalkynyl, aryl, and/or heteroaryl group.

The $R^1$ group may include one or more functional groups. Preferably, $R^1$ includes one or more other functional groups that can undergo a chemical transformation without chemically transforming the boron. Examples of functional groups that may be present as part of $R^1$ include halogen or pseudohalogen (—X), alcohol (—OH), aldehyde (—CH=O), ketone (>C(=O)), carboxylic acid (—C(=O)OH), thiol (—SH), sulfone, sulfoxide, amine, phosphine, phosphite, phosphate, and combinations of these. Moreover, examples of functional groups that may be present as part of $R^1$ include metal-containing groups, such as groups that contain metals such as tin (Sn), zinc (Zn), silicon (Si), boron, and combinations of these. Examples of organic groups that include functional groups and that may be present in a protected organoboronic acid are listed in Table 1:

TABLE 1

Organic groups containing other functional groups in selected protected organoboronic acids $R^1$ is an alkyl group

—(CH$_2$)$_5$—OH $R^1$ is an alkenyl group*

—CH=CH(CH$_2$)$_4$—OH —CH=CH—CH=CH—Cl
—CH=CH—Br —CH=CH—CH=C(CH$_3$)$_3$—Cl

TABLE 1-continued

Organic groups containing other functional groups in selected protected organoboronic acids —CH=C(CH)$_3$—Br —CH=CH—C(CH)$_3$=CH—Cl
—C(CH)$_3$=CH—Br —(CH=CH)$_3$—Cl
—C(CH)$_3$=C(CH)$_3$—Br —C(CH$_3$)=CH—(CH=CH)$_2$—Cl
—C(CH)$_3$=C(CH)$_3$—Cl —C(CH$_3$)=CH—CH=CH—C(CH$_3$)=CH—Cl $R^1$ is an aryl group —C$_6$H$_4$—F —C$_6$H$_4$—CH(=O)
—C$_6$H$_4$—Cl —C$_6$H$_4$—C(=O)OH
—C$_6$H$_4$—Br $R^1$ is a heteroaryl group

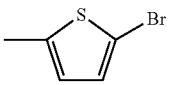

$R^1$ is a combination of an alkyl or alkenyl group, with an aryl or heteroaryl group

—C$_6$H$_4$—CH$_2$—OH
—C$_6$H$_4$—CH=CH—I*
—C$_6$H$_4$—CH$_2$—I

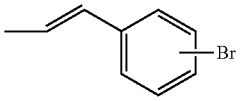

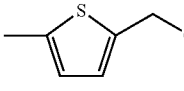

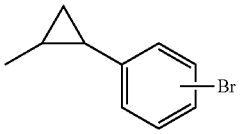

*May be cis- or trans- (or E- or Z-) isomer.
Additional examples of organic groups including functional groups that may be present in a protected organoboronic acid are illustrated or described throughout the present application.

Examples of functional groups that may be present as part of $R^1$ include protected alcohols, such as alcohols protected as silyl ethers, for example trimethylsilyl ether (TMS), t-butyldiphenylsilyl ether (TBDPS), t-butyldimethylsilyl ether (TBDMS), triisopropylsilyl ether (TIPS); alcohols protected as alkyl ethers, for example methoxymethyl ether (MOM), methoxyethoxymethyl ether (MEM), p-methoxybenzyl ether (PMB), tetrahydropyranyl ether (THP), methylthiomethyl ether; alcohols protected as carbonyl groups, such as acetate or pivaloylate. Examples of functional groups that may be present as part of $R^1$ include protected carboxylic acids, such as carboxylic acids protected as esters, for example methyl ester, t-butyl ester, benzyl ester and silyl ester. Examples of functional groups that may be present as part of $R^1$ include protected amines, such as amines protected as carbamates, for example N-(trimethylsilyl)ethoxycarbamate (Teoc), 9-fluorenylmethyl carbamate (FMOC), benzylcarbamate (CBZ), t-butoxycarbamate (t-BOC); and amines protected as benzylamines.

In another example, a protected organoboronic acid may be represented by formula (II), where the $R^1$ group is represented by formula (III):

$$Y-R^2-(R^3)_m- \qquad (III),$$

where Y represents a halogen group or a pseudohalogen group; $R^2$ represents an aryl group or a heteroaryl group; $R^3$ represents an alkyl group, a heteroalkyl group, an alkenyl group, a heteroalkenyl group, an alkynyl group, a heteroalkynyl group, an aryl group, a heteroaryl group, or a combination of at least two of these groups; and m is 0 or 1. $R^2$ may be, for example, a heteroaryl group. Moreover, $R^2$ and $R^3$ independently may include one or more substituent groups, which may include a heteroatom bonded to a carbon of the $R^2$ or $R^3$ group. The $R^2$ and $R^3$ groups independently also may include one or more functional groups, as described for $R^1$ above.

In this example, the protected organoboronic acid is a protected haloorganoboronic acid. The Y-group may undergo Suzuki-Miyaura cross-coupling with a compound that includes a free boronic acid, without reaction of the boron of the protected organoboronic acid. Deprotection of the boron provides the free boronic acid, which may then undergo Suzuki-Miyaura cross-coupling with a compound that includes a halogen group or a pseudohalogen group. These protected haloorganoboronic acids may thus be used as bifunctional building blocks for iterative synthesis through selective Suzuki-Miyaura transformations.

In one example, a protected organoboronic acid may include a boron having an $sp^3$ hybridization, a conformationally rigid protecting group bonded to the boron, and an organic group bonded to the boron through a boron-carbon (B—C) bond, where the organic group is not one of the groups listed in Table 2, below. The protecting group may be a trivalent group.

TABLE 2

Organic groups in selected protected organoboronic acids

| | |
|---|---|
| cyclopentyl; | —$C_2H_5$<br>—$C(CH_3)_2CH(CH_3)_2$ |
| norbornyl; | —$C_6H_5$<br>—$C_6H_4$—$CH_3$<br>—$C_6H_4$—$OCH_3$ |
| tetrahydropyranyl; | —$C_6H_4$—CHO<br>—$C_6H_4$—F |
| 2,4,4-trimethyl-bicyclo[3.1.1]heptanyl; | —$C_6H_4$—Cl<br>—$C_6H_4$—Br<br>—$C_6H_4$—$CF_3$<br>—$C_6H_4$—$NO_2$ |

In another example, a protected organoboronic acid may include a boron having an $sp^3$ hybridization, a conformationally rigid protecting group bonded to the boron, and an organic group bonded to the boron through a boron-carbon (B—C) bond, where the organic group is not one of the groups listed in Table 2 or in Table 3, below. The protecting group may be a trivalent group.

TABLE 3

Organic groups in selected protected organoboronic acids

| | |
|---|---|
| —$C_6H_4$—$C_6H_4$—$CH_3$ | -4-bromothiophenyl |
| -4-tolyl-thiophenyl | -cyclopropyl-$C_6H_4$—Br |

TABLE 3-continued

Organic groups in selected protected organoboronic acids

| | |
|---|---|
| -cyclopropyl-$C_6H_4$—$C_6H_4$—$CH_3$ | —CH=CH—$C_6H_4$—Br |
| —CH=CH—$C_6H_4$—$C_6H_4$—$CH_3$ | -5-bromo-2-benzofuranyl |
| -2-methoxymethoxy-4-methoxy-5-(5-(1-propenyl)-2-benzofuranyl)phenyl | -5-(1-propenyl)-2-benzofuranyl<br>-2-methoxymethoxy-4-methoxy-5-bromophenyl |

In this example, the protected organoboronic acid may be represented by formula (IV):

$$R^4—(R^5)_m—B-T \qquad (IV),$$

where $R^4$ and $R^5$ together represent the organic group, m is 0 or 1, T represents a conformationally rigid protecting group, and B represents the boron having $sp^3$ hybridization. The $R^4$ and $R^5$ groups independently may be an alkyl group, a heteroalkyl group, an alkenyl group, a heteroalkenyl group, an alkynyl group, a heteroalkynyl group, an aryl group, a heteroaryl group, or a combination of at least two of these groups. Preferably, in this example, $R^4$ is not an aryl group that includes a halogen substituent group or a pseudohalogen substituent group. For example, $R^4$ may be an alkyl group, a heteroalkyl group, an alkenyl group, a heteroalkenyl group, an alkynyl group, a heteroalkynyl group or a heteroaryl group, and may include a halogen substituent group or a pseudohalogen substituent group. For example, $R^4$ may be a group that does not contain a halogen or a pseudohalogen group, and may further be an aryl group.

In formulas (II) and (IV), the group T represents a conformationally rigid protecting group bonded to the boron. Conformational rigidity of an organic protecting group bonded to a boron atom is determined by the following "conformational rigidity test". A 10 milligram (mg) sample of a compound including a boron atom and an organic protecting group bonded to the boron is dissolved in dry $d_6$-DMSO and transferred to an NMR tube. The sample is then analyzed by $^1$H-NMR at temperatures ranging from 23° C. to 150° C. At each temperature, the sample shim is optimized, and a $^1$H-NMR spectrum obtained. If the protecting group is not conformationally rigid, then split peaks for a set of diastereotopic protons in the $^1$H-NMR spectrum obtained at 23° C. will coalesce into a single peak in the $^1$H-NMR spectrum obtained at 100° C. If the protecting group is conformationally rigid, then split peaks for a set of diastereotopic protons in the $^1$H-NMR spectrum obtained at 23° C. will remain split, and will not coalesce into a single peak in the $^1$H-NMR spectrum obtained at 90° C. An example of this test is provided in Example 10 below.

In one example of a protected organoboronic acid that includes a conformationally rigid protecting group bonded to the boron, a protected organoboronic acid may be represented by formula (X):

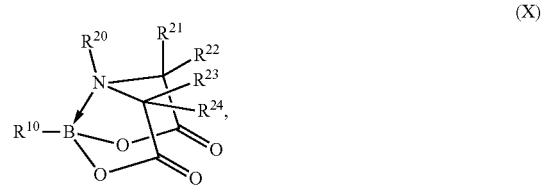

(X)

where $R^{10}$ represents an organic group, B represents a boron having $sp^3$ hybridization, and $R^{20}$, $R^{21}$, $R^{22}$, $R^{23}$ and $R^{24}$ independently are a hydrogen group or an organic group.

$R^{20}$, $R^{21}$, $R^{22}$, $R^{23}$ and $R^{24}$ independently may be an alkyl group, a heteroalkyl group, an alkenyl group, a heteroalkenyl group, an alkynyl group, a heteroalkynyl group, an aryl group, a heteroaryl group, or a combination of at least two of these groups. In one example, $R^{20}$ is methyl, and each of $R^{21}$, $R^{22}$, $R^{23}$ and $R^{24}$ is hydrogen. The protected organoboronic acid of this example may be represented by formula (XI):

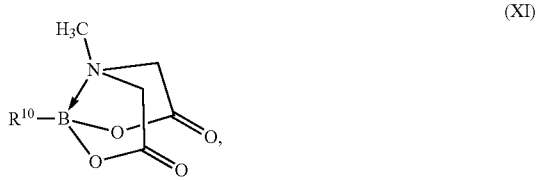

where $R^{10}$ represents the organic group, and B represents the boron having sp³ hybridization. The $R^{10}$ group may be an alkyl group, a heteroalkyl group, an alkenyl group, a heteroalkenyl group, an alkynyl group, a heteroalkynyl group, an aryl group, a heteroaryl group, or a combination of at least two of these groups, as described for $R^1$, above. The $R^{10}$ group may include one or more substituent groups, and/or one or more functional groups.

Protected organoboronic acids according to formula (X) may be prepared by reaction of an appropriate N-substituted imino-di-carboxylic acid with the corresponding unprotected boronic acid (XII), as illustrated in the following reaction scheme:

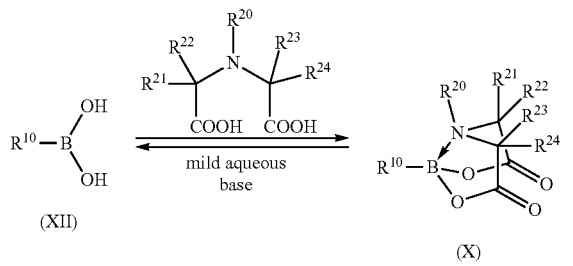

In a specific example, protected organoboronic acids according to formula (XI) may be prepared by reaction of N-methyliminodiacetic acid (MIDA) with the corresponding unprotected boronic acid (XII), as illustrated in the following reaction scheme:

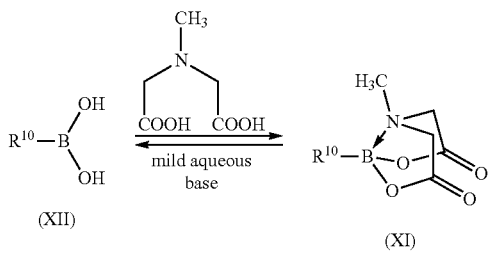

In each case, the protected organoboronic acid may be deprotected by contact with a mild aqueous base, to provide the free boronic acid (XII).

Figure 23:
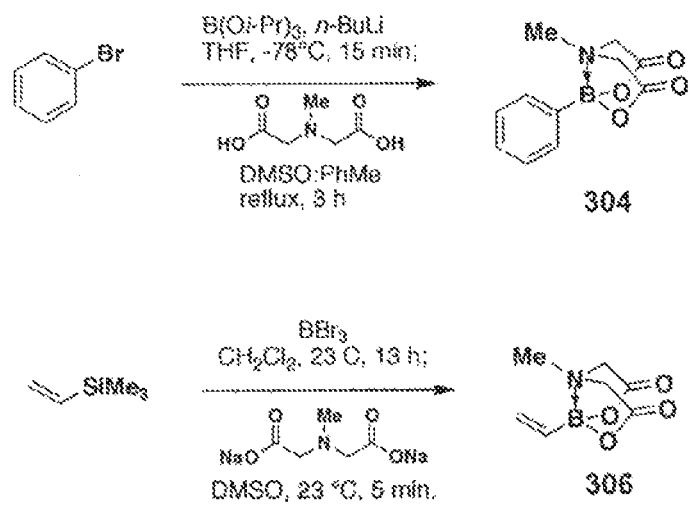
FIG. 23 represents structures and reaction schemes for the preparation of protected organoboronic acids without the formation of the corresponding free boronic acid.

Protected organoboronic acids according to formula (X) also may be prepared without using an isolated boronic acid as a reactant. The boronic acid may be formed in situ, just prior to its conversion to a protected organoboronic acid. Protected organoboronic acids also may be formed without ever forming the free boronic acid. FIG. 23 shows structures and reaction schemes for the preparation of protected organoboronic acids without the formation of the corresponding free boronic acid. Experimental details are provided in Example 20.

In one example, the boronic acid may be produced in situ, such as by hydrolysis of a boronate ester (i.e. $R^{10}$—B—(OR')(OR"), R' and R" are organic groups). The boronate ester may be formed, for example, by addition of HB(OR')(OR") across the C—C multiple bond of an alkene or an alkyne. (Brown, 1972) The boronate ester also may be formed, for example, by a Miyaura borylation (Miyaura, 1997; Miyaura, JOC, 1995.); by reaction of an organohalide with an organolithium reagent, followed by reaction with boronate triester (i.e. B(OR)₃); or by reaction of a boronate triester with an organometal reagent (i.e. R—Li, R—Mg, R—Zn; Brown, 1983). In another example, the boronic acid may be produced in situ, such as by treatment of a tri-substituted borane (i.e. $R^{10}$—BR'R") with acetaldehyde (R' and R" are organic groups). The tri-substituted borane may be formed, for example, by hydroborylation of an alkene or an alkyne with HBR'R", to add the HBR'R" across the C—C multiple bond.

In another example, a boronic halide (XIII) may be reacted with a diacid or its corresponding salt to provide protected organoboronic acid (X), as illustrated in the following reaction scheme:

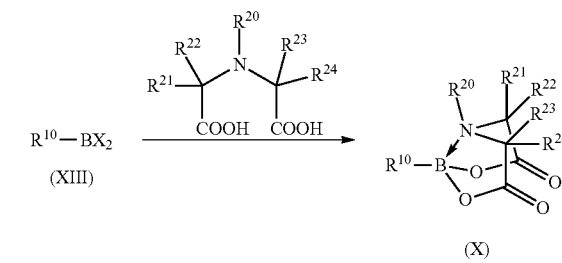

The boronic halide may be formed by hydroborylation of an alkene or an alkyne with HBX₂ (Brown, 1984; Brown, 1982) or with BX₃ (Soundararajan, 1990). The boronic halide also may be formed by treatment of a silane such as $R^{10}$—SiR₃ with BBr₃. (Qin, 2002; Qin, 2004)

Protected organoboronic acids including a MIDA boronate ester protecting group are readily purified by column chromatography. This is unusual for boronic acids, which are typically unstable to chromatographic techniques. These compounds also may be highly crystalline, which facilitates purification, utilization, and storage. These compounds are extremely stable to long term storage, including storage on the bench top under air. This is also unusual, as many boronic acids are unstable to long term storage.

Figure 25A:
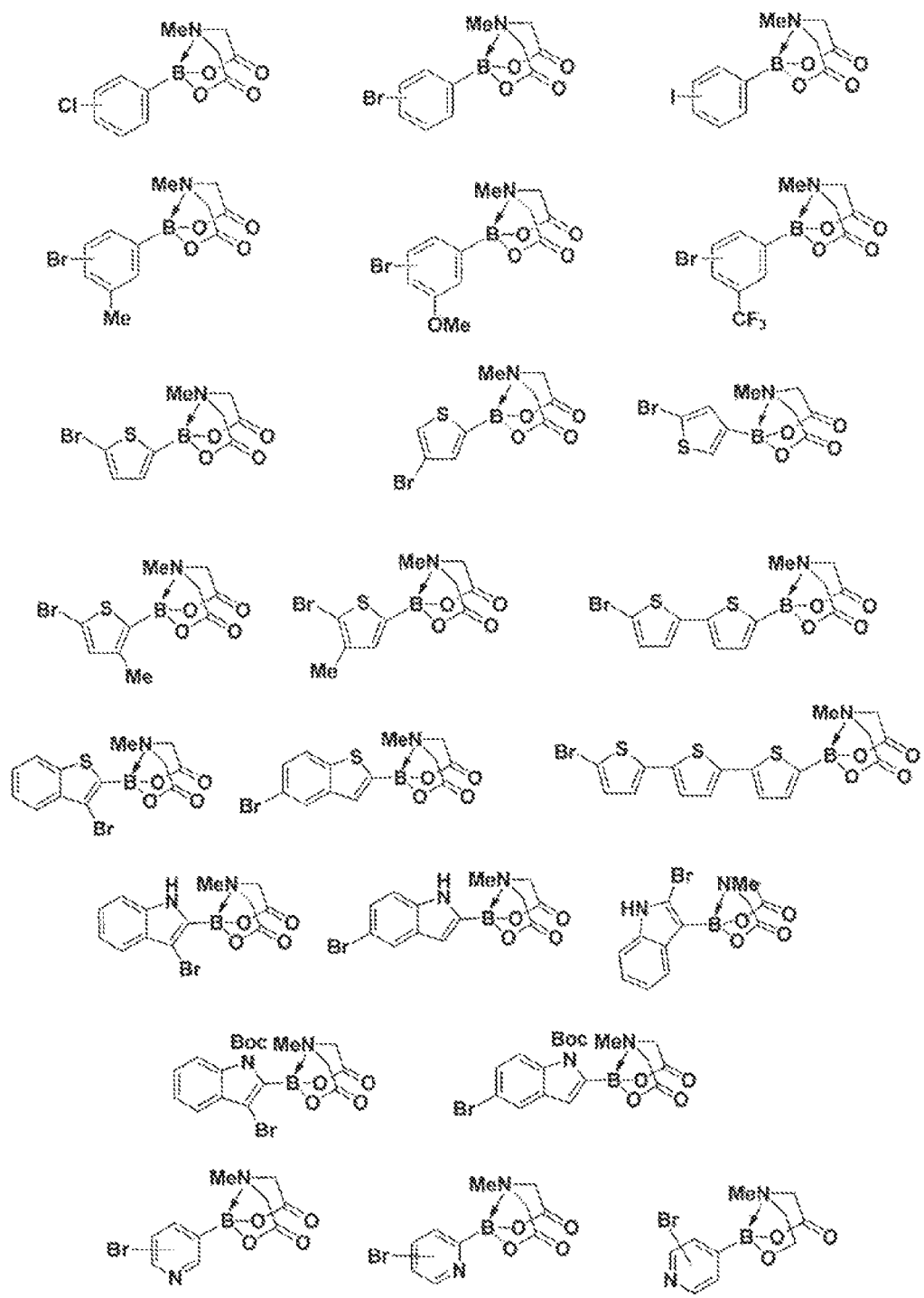
FIGS. 25A-B represent examples of protected haloorganoboronic acid building blocks.
Figure 25B:
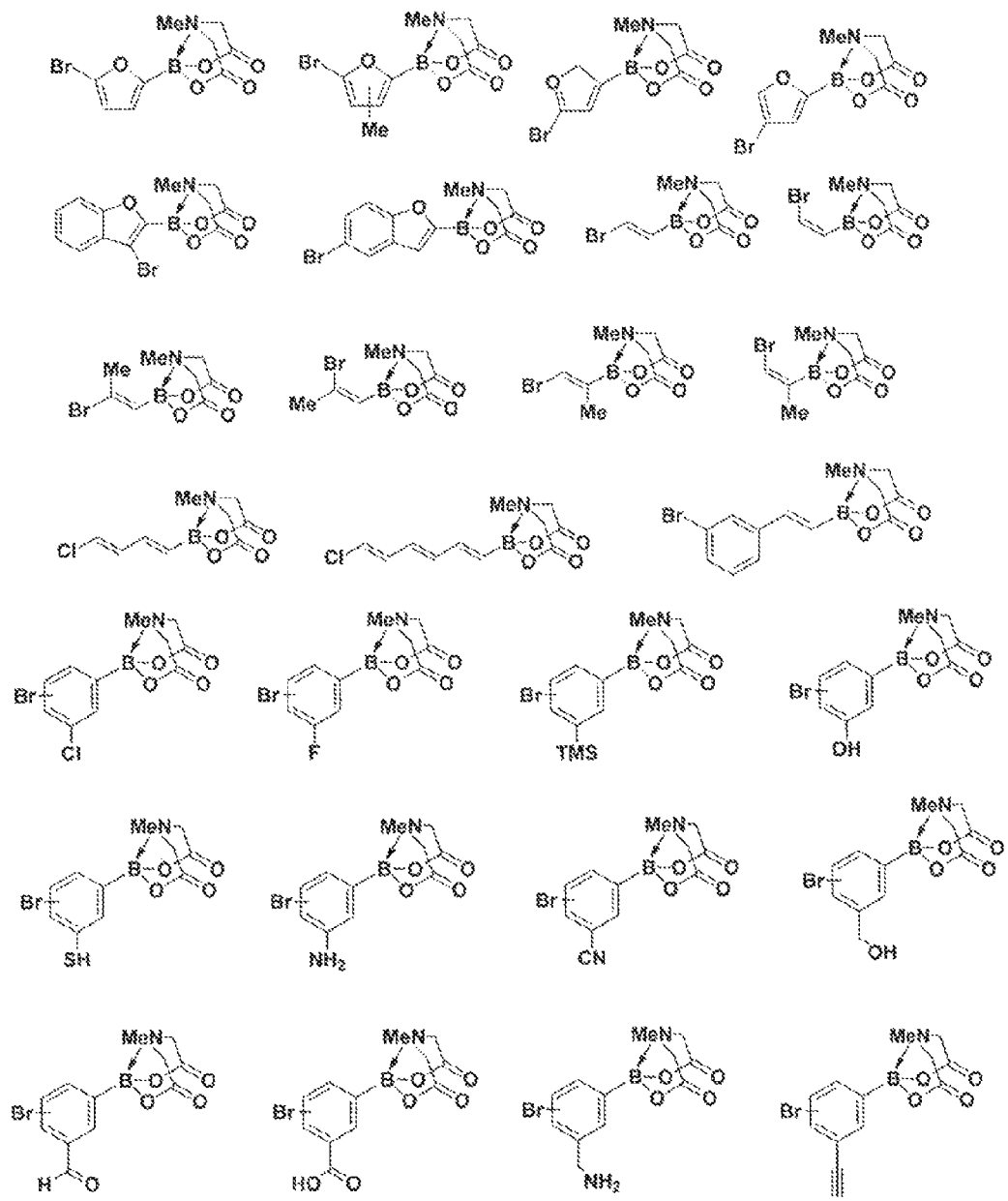
Figure 26:
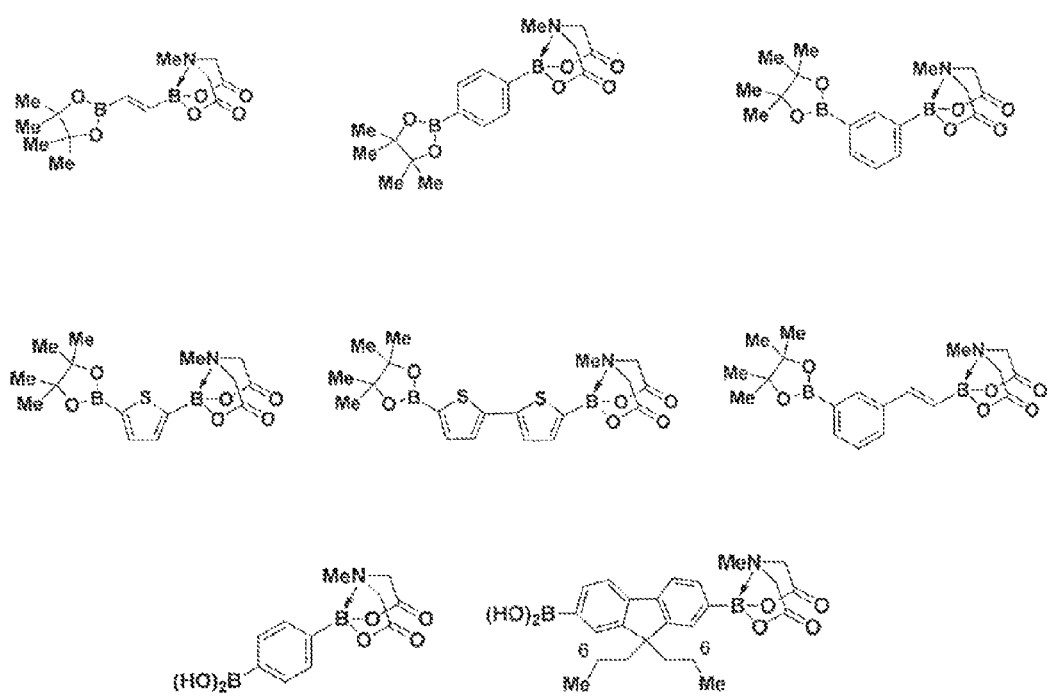
FIG. 26 represents examples of bis-boronate building blocks.
Figure 27A:
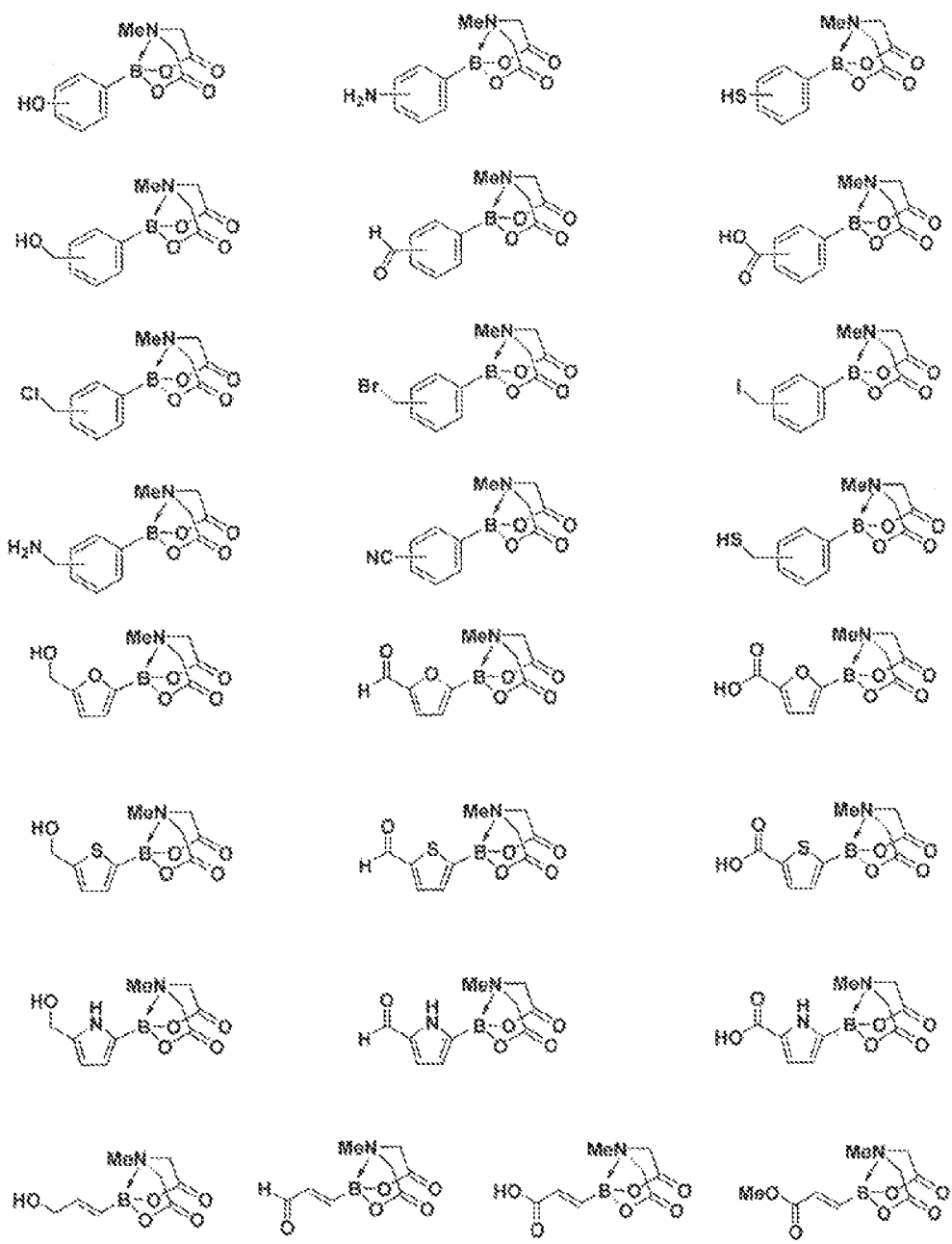
FIGS. 27A-B represent examples of protected organoboronic acid building blocks in which the organic group includes a functional group.
Figure 27B:
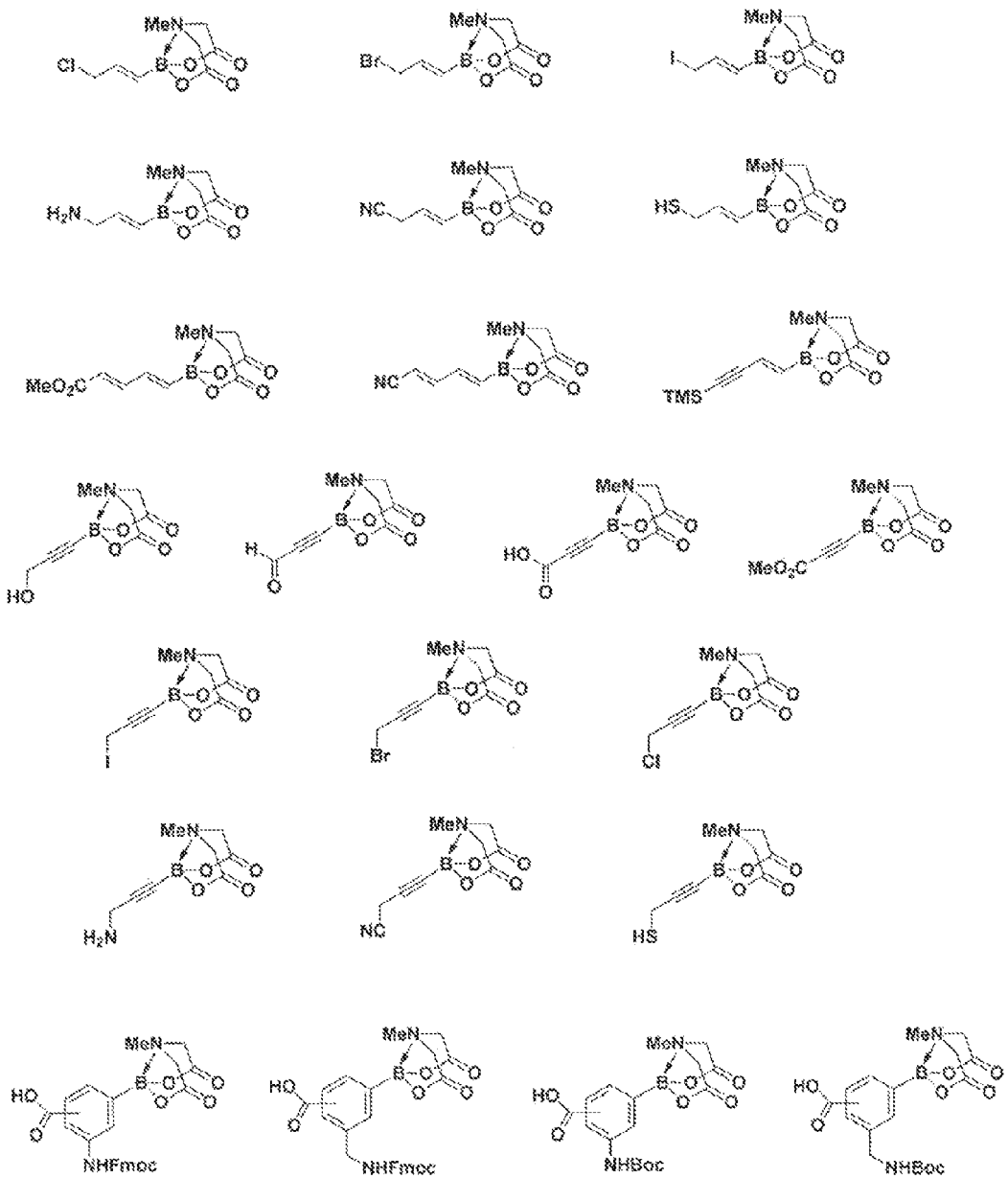
Figure 28:
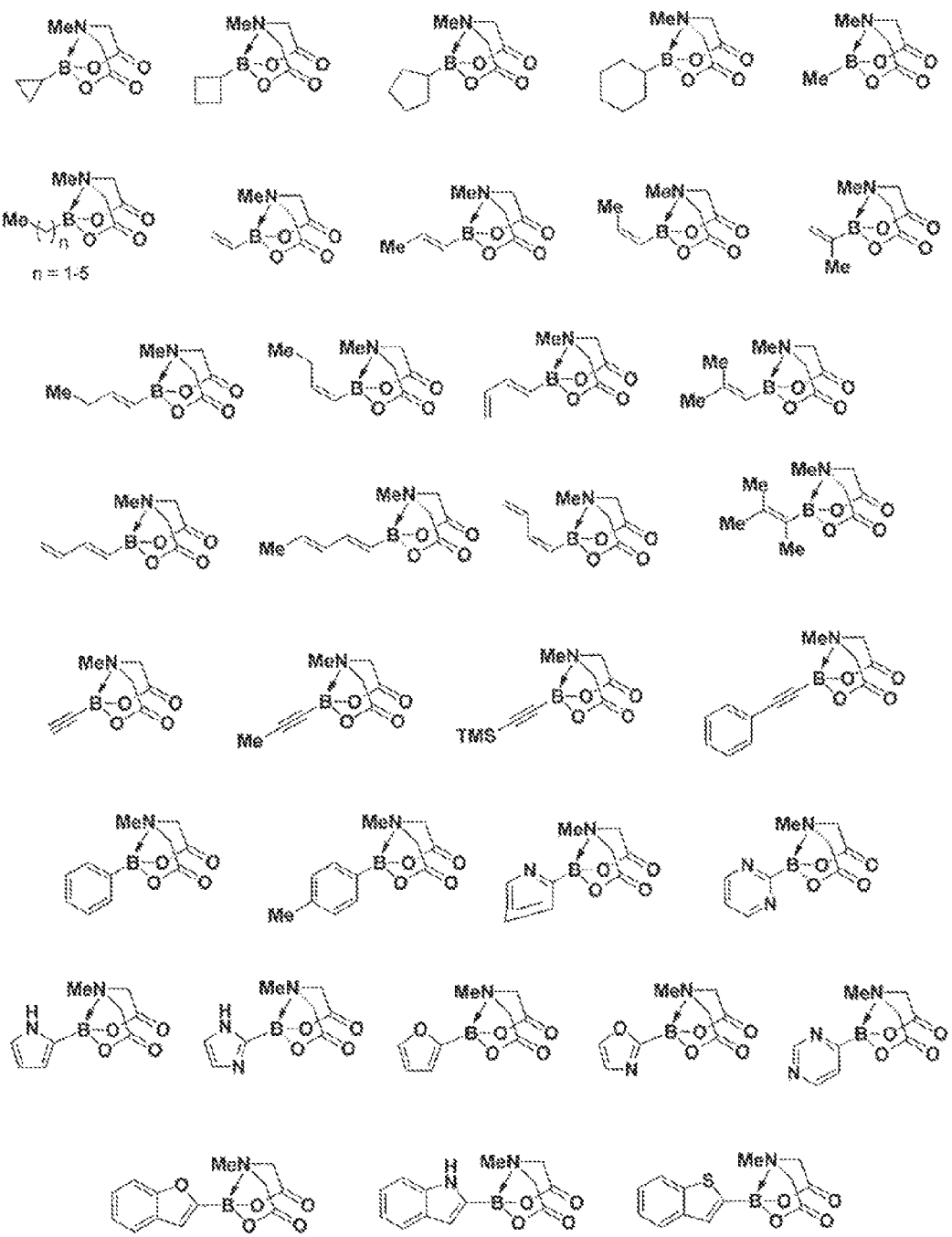
FIG. 28 represents examples of protected organoboronic acid building blocks.

Protected organoboronic acids including a boron having an sp³ hybridization, a conformationally rigid protecting group bonded to the boron, and an organic group may be useful as synthetic building blocks. Examples of building blocks include protected haloorganoboronic acids, such as those listed in FIG. 25. Examples of building blocks include bis-boronates having a first boron atom having an sp³ hybridization and a conformationally rigid protecting group bonded to the first boron atom, and a second boron atom that may be present as a boronic acid or as a different type of protected boron. Examples of bis-boronates include those listed in FIG. 26, and derivatives of these bis-boronates in which the second boron atom is present as a boronic acid, a boronic ester (including a pinacol ester), —$BF_3^-$ or —$B(OH)_3^-$. Examples of building blocks include protected organoboronic acids in which the organic group includes a functional group, such as those listed in FIG. 27. Examples of other miscellaneous building blocks are listed in FIG. 28. The protecting group in each of these building blocks is represented as the MIDA boronate ester. Protected organoboronic acid building blocks may also include compounds having one or more substitutent groups on the protecting group, and/or having a different group bonded to the nitrogen of the protecting group. For example, the protecting groups in these building blocks may be a protecting group as described for formula (X).

Protected organoboronic acids including a MIDA boronate ester protecting group have a number of advantageous properties. The MIDA group is typically effective in decreasing the reactivity of the boronic acid to which it is esterified. One possible explanation for this decrease in reactivity is that a vacant, Lewis acidic boron p-orbital is not available to react with other substances. For example, the protected boron no longer has a vacant, Lewis acidic p-orbital to complex with the palladium catalyst involved in the Suzuki-Miyaura transformation. Thus, this protection strategy should decrease the reactivity of any boronic acid, including its reactivity toward the Suzuki-Miyaura transformation. In addition, the MIDA boronate ester group seems to be stable to a wide variety of reaction conditions, besides cross-coupling. This stability may facilitate their utilization in the synthesis of complex synthetic building blocks that contain boronic acid functional groups.

Although these $sp^3$-hybridized boronate esters having a conformationally rigid protecting group bonded to the boron are protected from anhydrous Suzuki-Miyaura coupling even at 80° C. for 28 hours, deprotection can be readily achieved at 23° C. using extremely mild aqueous basic conditions. One example of deprotection conditions is treatment with 1 molar (M) aqueous sodium hydroxide (NaOH) in tetrahydrofuran (THF) for 10 minutes. Another example of deprotection conditions is treatment with saturated aqueous sodium bicarbonate ($NaHCO_3$) in methanol (MeOH) for 6 hours. These mild conditions are in contrast to typical protecting groups based on boronate esters, which can require harsh cleavage conditions.

Figure 2A:
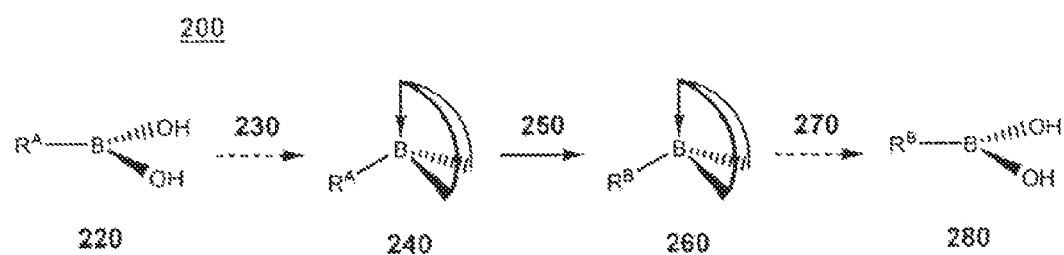
FIG. 2A represents a method of performing a chemical reaction.

FIG. 2A represents a method 200 of performing a chemical reaction, including contacting 220 a protected organoboronic acid 204 with a reagent, where the organic group is chemically transformed, and the boron is not chemically transformed. Protected organoboronic acid 206 is a chemical transform of protected organoboronic acid 204 in which $R^A$ has been transformed into $R^B$, but the boron has not been chemically transformed. The method optionally includes forming the protected organoboronic acid 204 by reacting 210 a boronic acid 202 with a protecting reagent. The protected organoboronic acid 204 may also be formed without forming and/or isolating the boronic acid 202. The method optionally includes deprotecting 230 the protected organoboronic acid 206 to form boronic acid 208.

Figure 2B:
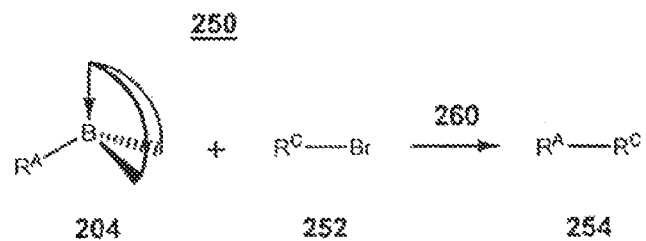
FIG. 2B represents a method of performing a chemical reaction.

FIG. 2B represents a method 250 of performing a chemical reaction, including reacting 260 the protected organoboronic acid 204 with an organohalide 252, to provide the cross-coupled product 254. The reacting 260 may include contacting the protected organoboronic acid 204 and organohalide 252 with a palladium catalyst in the presence of aqueous base. The protecting group may be cleaved in situ, providing the free boronic acid (i.e. 202 in FIG. 2A), which can then cross-couple with the organohalide 252. Thus, in addition to serving as protected building blocks during complex synthesis, the protected organoboronic acids can be useful as stable, pure derivatives of boronic acids.

The protected organoboronic acid 204 includes a boron having an $sp^3$ hybridization, a conformationally rigid protecting group, and an organic group $R^1$ bonded to the boron through a B—C bond. The protected organoboronic acid 204 may be any of the protected organoboronic acids disclosed above. Preferably the protected organoboronic acid 204 includes a trivalent protecting group bonded to the boron.

The protected organoboronic acid 204 may be, for example, represented by formula (II), as described above. For example, the protected organoboronic acid 204 may be represented by formula (II), where the $R^1$ group is represented by formula (III), as described above. The protected organoboronic acid 204 may be, for example, represented by formula (IV), as described above. The protected organoboronic acid 204 may be, for example, represented by formula (X) or (XI), as described above.

Figures 3, 4:
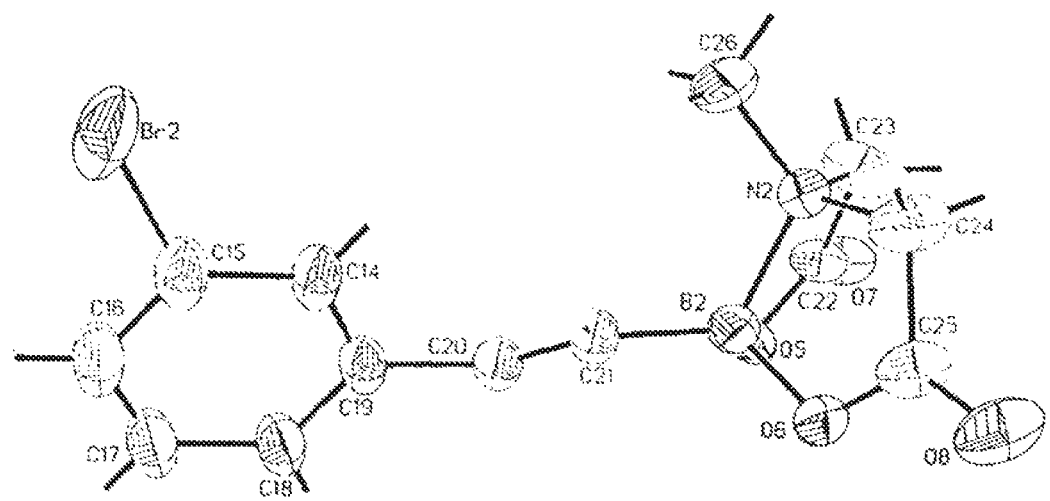
FIG. 3 represents an X-ray crystal structure of an example of a protected organoboronic acid.
FIG. 4 represents chemical structures, reaction schemes and product ratios for an example of a reaction of protected and unprotected organoboronic acids in a Suzuki-Miyaura transformation.

FIG. 3 is a representation of an X-ray crystal structure of an example of a protected organoboronic acid, (N→B)-tolyl-[N-methyliminodiacetate-O,O',N]borane 3a. In this structure, the boron (B2) is shown to be $sp^3$ hybridized, and is in a tetrahedral orientation.

FIG. 4 shows chemical structures, reaction schemes and product ratios for an example of a reaction of protected and unprotected organoboronic adds in a Suzuki-Miyaura transformation. Stoichiometric quantities of para-n-butylphenylboronic acid 2 and (N→B)-tolyl-[N-methyliminodiacetate-O,O',N]borane 3a were reacted with 0.8 equiv. of p-bromobenzaldehyde under Buchwald's anhydrous Suzuki-Miyaura conditions. (Barder, 2005) A 24:1 ratio of biaryls 5 and 6 was observed, consistent with strong preferential reactivity of the p-bromobenzaldehyde with the $sp^2$-hybridized boronic acid 2 (entry 1). In contrast, the control experiment with p-tolylboronic acid 3b yielded a 1:1 mixture of products (entry 2). Sterically bulky N-alkyl substitution on the protecting group was tolerated, but was not significantly advantageous (entry 3). The N-methyl diethanolamine adduct 3d, which is known to be significantly less conformationally rigid than its iminodiacetic acid counterpart, (Contreras, 1983) demonstrated no selectivity (entry 4). Experimental details for the preparation and use of these compounds are provided in Examples 1 and 2, respectively.

Figure 5:
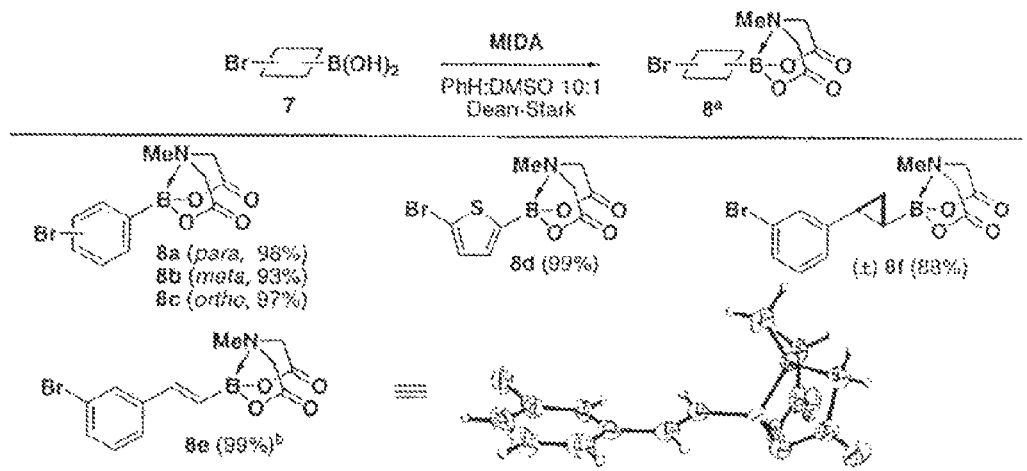
FIG. 5 represents chemical structures, reaction schemes and reaction yields for examples of the preparation of protected haloorganoboronic acids.

FIG. 5 shows chemical structures, reaction schemes and reaction yields for examples of the preparation of protected haloorganoboronic acids. A variety of haloboronic adds were complexed with MIDA to yield a series of B-protected bifunctional building blocks. All three positional isomers of bromophenylboronic acid, as well as the heteroaromatic 5-bromothiopheneboronic acid, reacted cleanly to generate 8a-d in excellent yields. The same complexation conditions yielded vinyl and alkyl boronate esters 8e and 8f. The pyramidalized nature of the (N→B)-vinyl-[N-methyliminodiacetate-O,O',N]borane 8e was confirmed via single crystal X-ray diffraction analysis. Remarkably, these pyramidalized boronate esters were stable to and readily purified by silica gel chromatography. All yields shown in FIG. 5 represent materials isolated as analytically-pure, colorless crystalline solids after a single chromatographic step. Moreover, in stark contrast to the corresponding boronic acids (Hall, 2005), all of these boronate esters were indefinitely bench stable under air. Experimental details are provided in Example 3.

Figure 6:
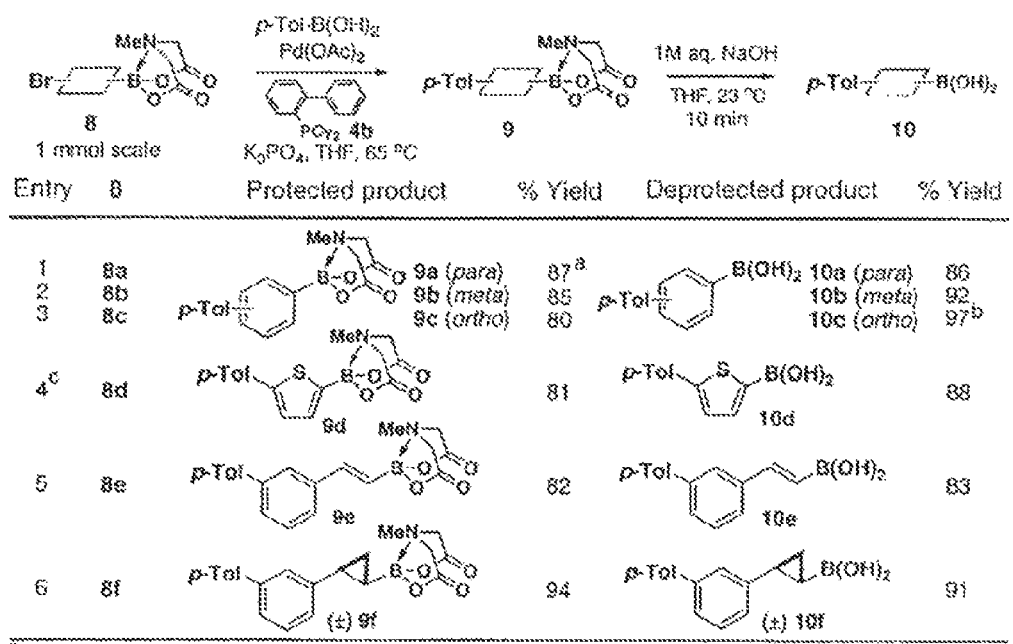
FIG. 6 represents chemical structures, reaction schemes and reaction yields for (a) the reaction of examples of protected organoboronic acids having halogen groups with unprotected boronic acids and (b) the deprotection of the coupled biaryl compounds.

FIG. 6 shows chemical structures, reaction schemes and reaction yields for (a) the reaction of protected organoboronic acids having halogen groups with unprotected boronic acids and (b) the deprotection of the coupled biaryl compounds to provide the free boronic acids. The potential of the MIDA ligand to enable selective cross-couplings was probed by reacting each of the B-protected bifunctional building blocks of Example 2 with p-tolylboronic acid. Although the reactivity of aryl, heteroaryl, vinyl, and alkylboronic acids can vary dramatically (Barder, 2005; Billingsley, 2007; Littke, 2000; Nicolaou, 2005), the same protecting group was effective with all four classes of nucleophiles, yielding selective cross-coupling products 9a-9f. All four classes of nucleophiles were also efficiently deprotected using a standard set of mild aqueous basic conditions of 1 molar (M) aqueous NaOH in THF, at 23° C., for 10 minutes. Saturated aqueous NaHCO₃ was also effective (entry 3). Experimental details are provided in Example 4.

Figure 7A:
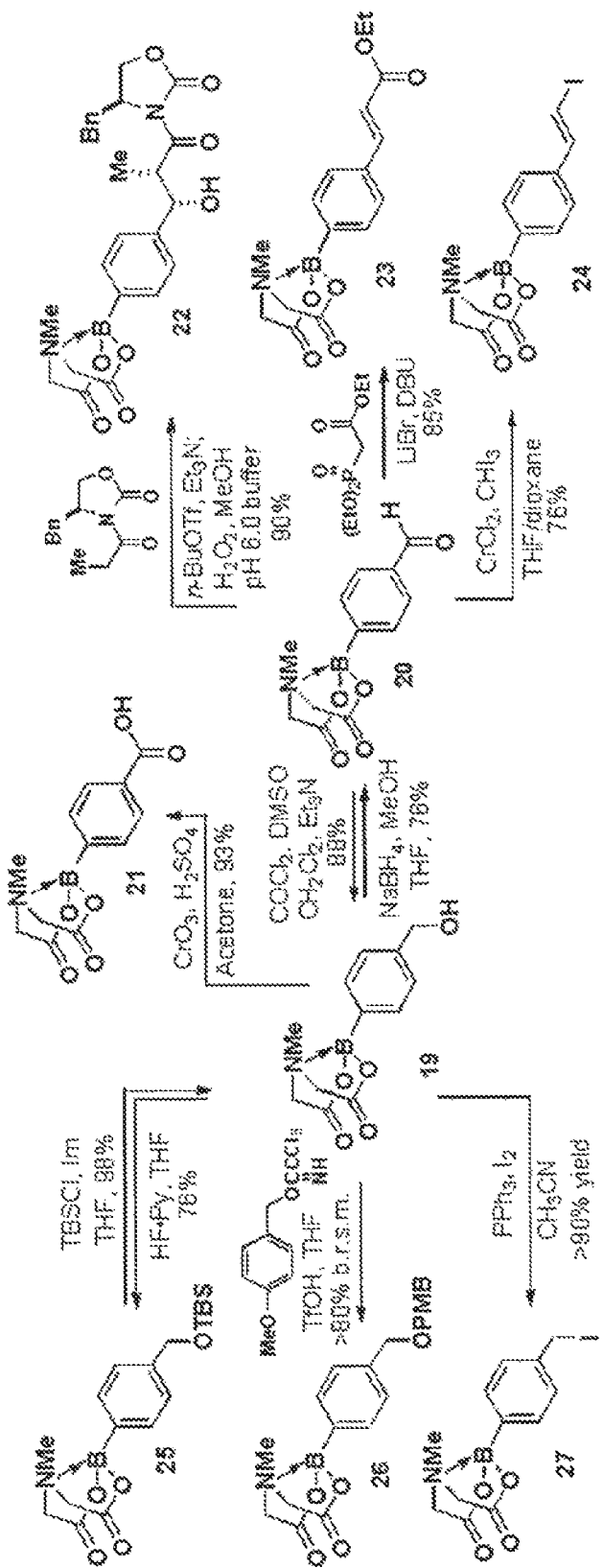
FIG. 7A represents a variety of chemical transformations of the organic group of protected organoboronic acids.

FIG. 7A shows chemical structures, reaction schemes and reaction yields for a variety of chemical transformations of protected organoboronic acids, where the organic group is chemically transformed, but the boron is not chemically transformed. The MIDA boronate esters were remarkably robust. In one example, protected organoboronic acid 19, MIDA-protected p-hydroxymethyl-phenyl-boronic acid, was smoothly transformed into the corresponding aldehyde 20 via a Swern oxidation, and the reverse transformation was achieved with sodium borohydride.

In another example, treatment of 19 with the very strongly oxidizing and acidic "Jones reagents" ($CrO_3$ and concentrated $H_2SO_4$) unexpectedly yielded benzoic acid derivative 21 without any observable decomposition of the protected organoboronic acid. This remarkable stability to extremely acidic conditions was very surprising, and contrasts sharply with the pronounced lability of MIDA-based protected organoboronic acid to very mild aqueous base, such as aqueous $NaHCO_3$. However, many non-aqueous bases seemed to be well-tolerated.

Figure 7B:
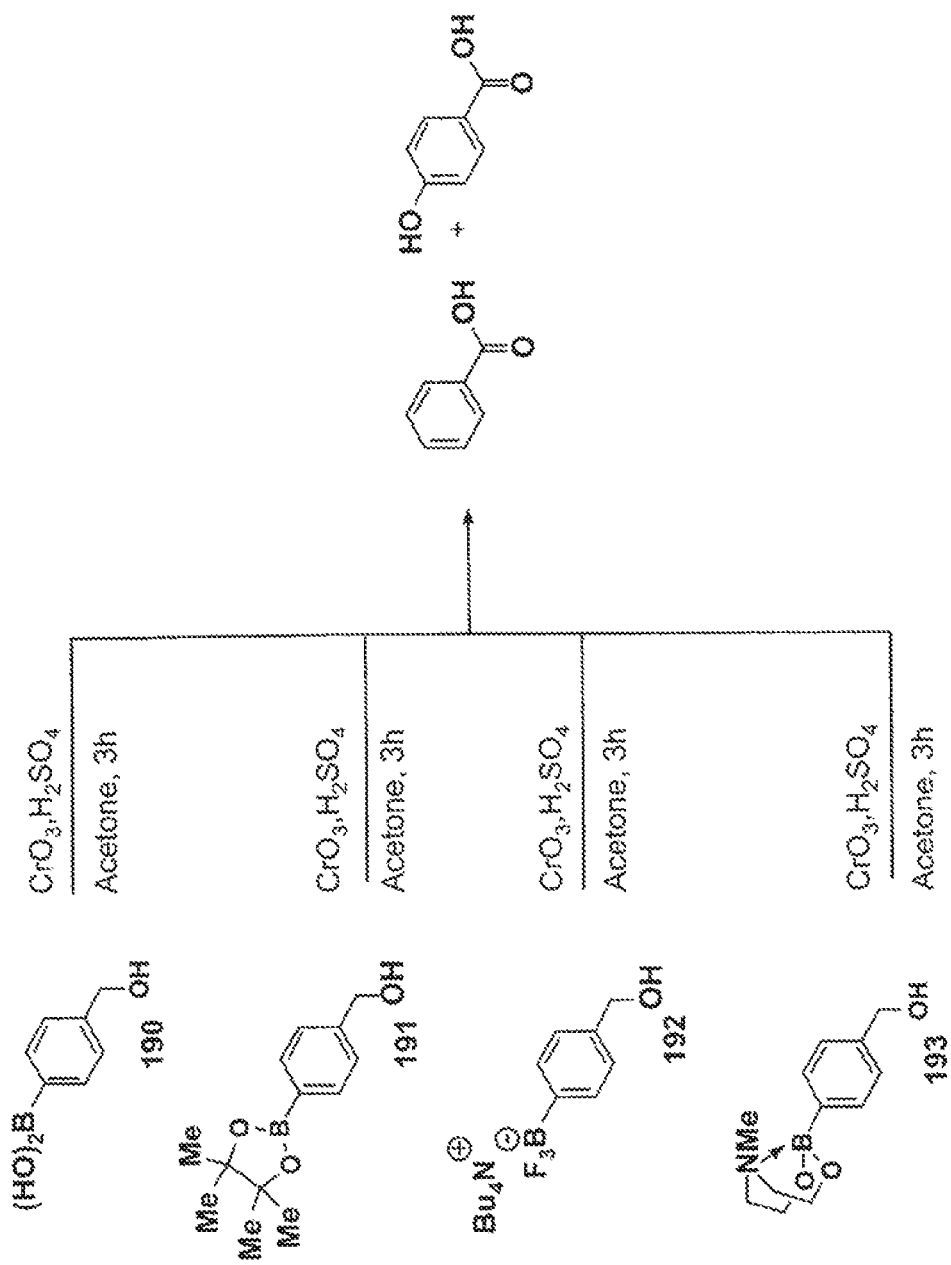
FIG. 7B represents chemical structures, reaction schemes and reaction yields for the treatment of a free boronic acid, and of a variety of its protected analogues, with "Jones reagents".

FIG. 7B shows chemical structures, reaction schemes and reaction yields for the treatment of a free boronic acid, and of a variety of its protected analogues, with "Jones reagents", using reaction conditions identical to those for the oxidation of 19 to 21. Reaction of the free boronic acid 190 provided a mixture of benzoic acid and p-hydroxybenzoic acid, with complete removal of the boron from the p-benzyl alcohol organic group. The protecting group for 191 was a pinacol ester group, where the boron was $sp^2$ hybridized. Protected analogue 192 included the boron as part of an anionic compound, specifically as an R—$BF_3^-$ anion. The protecting group for 193 was a N-methyldiethanolamine ester, which was not a conformationally rigid protecting group (see Example 10, below). The reactions of protected analogues 191, 192 and 193 each produced a mixture of benzoic acid and p-hydroxybenzoic acid, with complete removal of the boron from the p-benzyl alcohol organic group. Thus the boron of the protected organoboronic acid 19, which included a conformationally rigid protecting group bonded to an $sp^3$ hybridized boron and an organic group bonded to the boron through a boron-carbon bond, was surprisingly and unexpectedly inert to the oxidizing and acidic conditions of "Jones reagents".

Referring again to FIG. 7A, in another example, the protected organoboronic acid 19 was compatible with the carbanion-mediated Evans' aldol and HWE olefination reactions, yielding 22 and 23, respectively. The former also required a peroxide-mediated oxidative cleavage of the initially-formed boron-alkoxide aldol adduct, to which the MIDA complex was again surprisingly stable. In another example of a different carbon-carbon bond-forming reaction, the Takai olefination was also compatible with the protected organoboronic acid, providing a new way to access B-protected haloboronic acids such as 24.

In other examples, some common functional group transformations were also well-tolerated by the protected organoboronic acid. These transformations included alcohol silylation (25) and desilylation, p-methoxybenzylation with the extremely acidic catalyst TfOH (26), and iodination (27).

It has been demonstrated that a protected organoboronic acid, in which the organic group includes a boron that is not $sp^3$ hybridized, can undergo chemical transformation of the non-$sp^3$ hybridized boron without chemically transforming the boron having $sp^3$ hybridization. See, for example, FIG. 14. Thus, selective cross-coupling can be performed with a differentially-ligated bis-boronate reagent.

It has also been demonstrated that a protected organoboronic acid can undergo a transmetalation reaction with a compound containing two different types of metal atoms without chemically transforming the boron. See, for example, FIG. 15, which shows a Negishi cross-coupling between a protected haloorganoboronic acid and a bis-metallated vinyl compound including zinc and tin. Thus, a cross-coupling reaction can be performed, in which the transformation is triply-metal selective (B, Sn, Zn).

Figure 8:
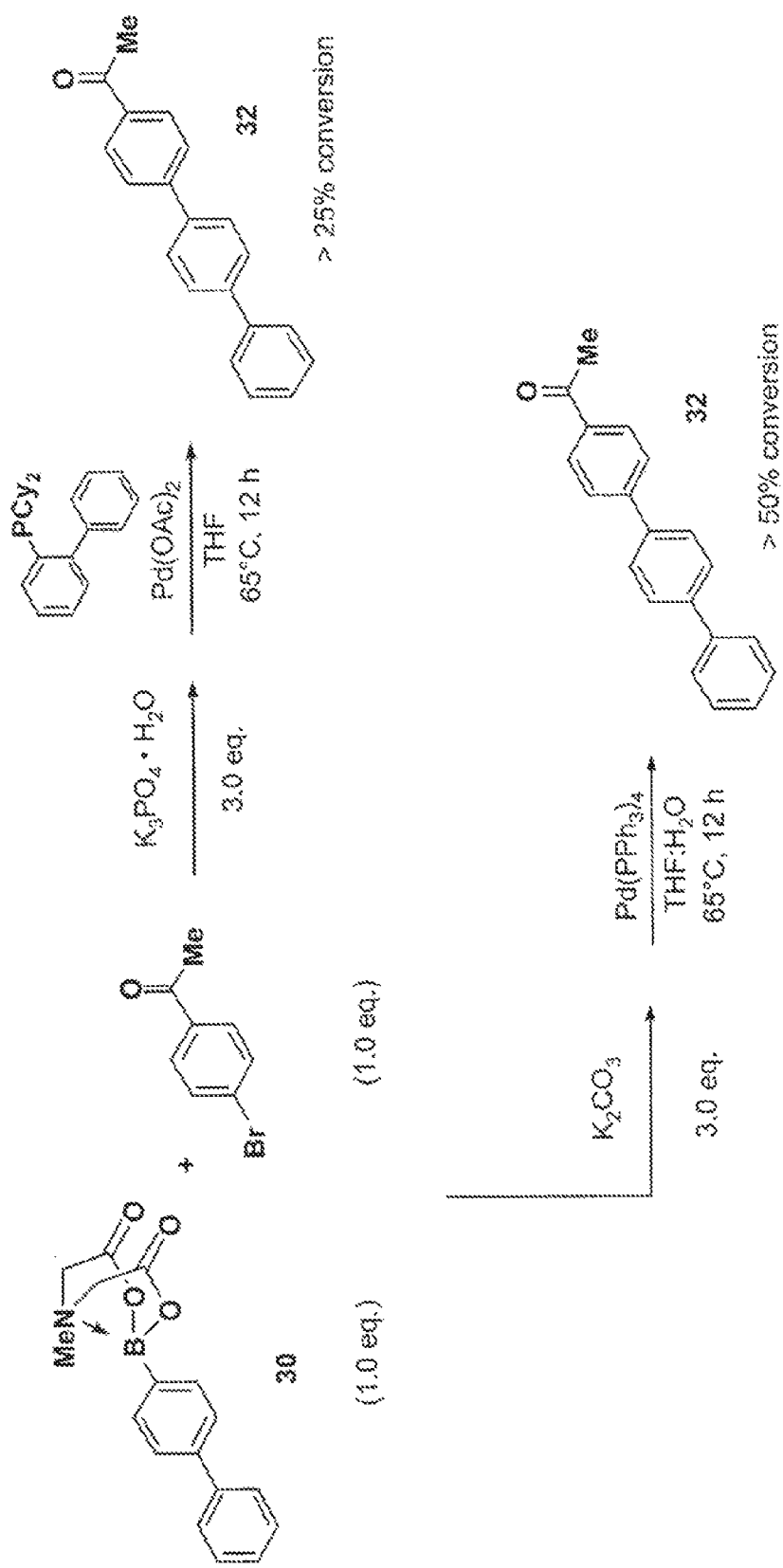
FIG. 8 represents an example of a reaction of a protected organoboronic acid in the Suzuki-Miyaura transformation under aqueous basic conditions.

FIG. 8 shows chemical structures, reaction schemes and reaction yields for the reaction of a protected organoboronic acid in the Suzuki-Miyaura transformation under aqueous basic conditions. Protected organoboronic acid 30 reacted with methyl p-bromophenyl ketone in the presence of a palladium catalyst, to provide the cross-coupled product 32. Since the reaction was performed in the presence of aqueous base, the MIDA boronate ester was cleaved in situ, providing the free boronic acid. Thus, in addition to serving as protected building blocks during complex synthesis, the protected organoboronic acids can be useful as stable, pure derivatives of boronic acids. As noted above, boronic acids can be difficult to purify and can be unstable during long-term storage. In contrast, protected organoboronic acids including a boron having $sp^3$ hybridization and having a conformationally rigid protecting group bonded to the boron can be purified by crystallization and/or chromatography, and can be stable for long periods of time, even in air.

These reactions demonstrate some of the possible applications of protected organoboronic acids that include a boron having an $sp^3$ hybridization and having a conformationally rigid protecting group bonded to the boron. These compounds may be used for simple, highly modular syntheses of molecules through iterative Suzuki-Miyaura cross-coupling transformations. These transformations may involve bifunctional building blocks, such as protected organoboronic acids that include a halogen or a psuedohalogen group. For a given synthesis, all the building blocks may be prepared having the required functional groups preinstalled in the correct oxidation state and with the desired stereochemical relationships. These building blocks may then be brought together by the recursive application of one mid reaction, such as the Suzuki-Miyaura reaction. In addition to being very simple, efficient, and potentially amenable to automation, this strategy is inherently modular and thus well-suited for making collections of structural derivatives.

This iterative cross-coupling strategy can dramatically simplify the process of small molecule synthesis. For example, the natural product ratanhine has been prepared using the mild Suzuki-Miyaura reaction iteratively to bring together a collection of easily synthesized, readily purified, and highly robust building blocks. The synthesis was short and highly modular, and thus a variety of derivatives should be readily accessible simply by substituting modified building blocks into the same pathway.

Figure 9:
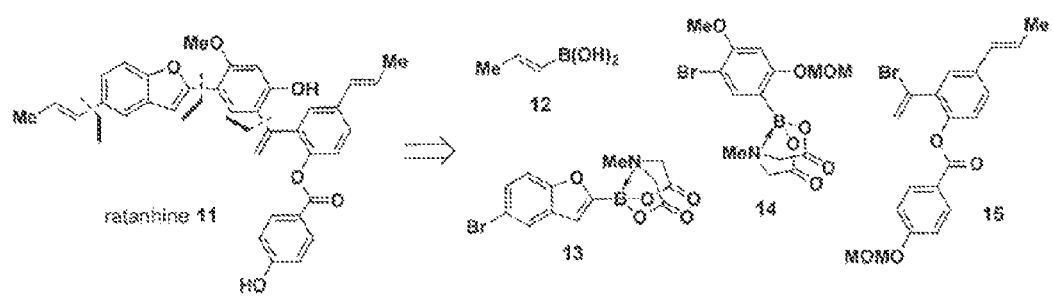
FIG. 9 represents an example scheme for the retrosynthetic fragmentation of ratanhine.

FIG. 9 shows a scheme for the retrosynthetic fragmentation of ratanhine 11 into four simpler building blocks 12-15 via recursive application of three Suzuki-Miyaura transforms. The natural product ratanhine is the most complex member of a large family of neolignans isolated from the medicinal plant *Ratanhiae radix*. (Arnone, 1990) There were several challenges associated with this plan that provided rigorous tests for the protected organoboronic acids. For example, cross-coupling of aryl boronic acids tends to be more facile than that of their vinyl counterparts (Barder, 2005), making the selective cross-coupling between vinyl boronic acid 12 and bromoarylboronate 13 unsecured. In addition, heteroaromatic boronic acids, such as the deprotected version of 13, can be very sensitive to decomposition. (Tyrell, 2003) Moreover, cross-coupling with the highly electron-rich and sterically-encumbered aryl bromide 14 was expected to require elevated temperatures and/or long reaction times that would test the limits of stability for the MIDA ligand.

Figure 10:
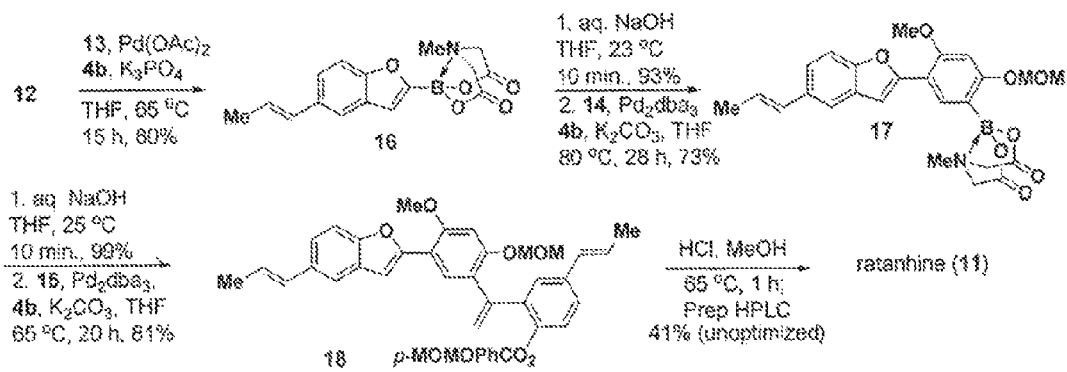
FIG. 10 represents the synthetic steps in an example of a total synthesis of ratanhine.

FIG. 10 shows chemical structures, reaction schemes and reaction yields for the synthetic steps in the total synthesis of ratanhine. Experimental details are provided in Examples 6-9. Once building blocks 13-15 were prepared (see Examples 6-8, respectively), the synthesis commenced with a successful selective cross-coupling between vinyl boronic acid 12 and bromoarylboronate 13 to yield intermediate 16. Strikingly, benzofuranylboronates 13 and 16 were bench stable under air for at least one month. In contrast, the 2-benzofuranylboronic add that resulted from deprotection of 16 rapidly decomposed over the course of a few days. This challenge was overcome simply by deprotecting 16 just prior to cross-coupling with 14. As expected, this electron-rich and sterically-bulky aryl bromide 14 required both an elevated temperature (80° C., sealed tube) and extended reaction time (28 hours). Remarkably, the MIDA protective group was found to be completely stable to these forcing conditions, yielding advanced intermediate 17. A final sequence of B-deprotection, cross-coupling with 15, and cleavage of the two MOM ethers completed the first total synthesis of ratanhine. This synthesis involved 7 steps in the longest linear sequence. All spectral data of the final product match that reported in Arnone (1990).

The class of small molecules collectively referred to as "polyene natural products" are remarkably diverse in origin, being synthesized by bacteria, fungi, slime-moulds, plants, a wide range of aquatic species, and even animals. These compounds also represent an extraordinary diversity of structures and functions, and may include a wide variety of double bonds, such as E- and Z-1,2-disubstituted, trisubstituted, and tetrasubstituted olefins. Activities of these compounds include antifungal, antibacterial, and antitumor properties, and many studies show that subtle modifications of these structures can have dramatic impacts on their activities. Undoubtedly, polyene natural products have substantial untapped potential for improving human health, and unfettered synthetic access to these compounds and their derivatives is paramount for realizing this potential. Protected organoboronic acids and their use in synthetic methods may provide a simple and modular assembly of a broad range of these targets through iterative cross-coupling.

The synthesis of polyenes is made challenging by the sensitivity of conjugated double bond frameworks to many common synthetic reagents. Controlling the geometry of each double bond is also a critical issue. Many valuable methods have been developed, but synthetic strategies based on palladium-mediated cross-coupling are particularly attractive due to the mild and stereospecific nature of these reactions. In this vein, a variety of methods based on bis-metallated (Lhermitte, 1996; Lipshutz 1997; Pihko, 1999; Babudri, 1998; Murakami, 2004; Denmark, 2005; Lipshutz, 2005; Coleman, 2005; Coleman, 2007) or bis-halogenated (Organ, 2000; Antunes, 2003; Organ, 2004) lynchpin reagents have been reported. In these approaches, three fragments are brought together using two cross-coupling reactions to engage the orthogonally-reactive termini of the lynchpin. An important advantage of the iterative cross-coupling strategy using protected organoboronic acids including a boron having $sp^3$ hybridization and having a conformationally rigid protecting group bonded to the boron is the inherent potential for limitless iteration. That is, all of the required building blocks can in theory be brought together via the recursive application of a single, mild reaction. This may dramatically simplify the synthesis process, and may readily enable analog preparation. The use of only one reaction also can help to minimize the potential for incompatibilities between the functional groups appended to the building blocks and the reaction conditions used to couple them. In addition, the use of bifunctional haloorganoboronic acids can avoid toxic metals such as organostannes, which are frequently employed in bis-metallated lynchpin-type reagents. Finally, the protected haloorganoboronic acids tend to be free-flowing crystalline solids that can be readily purified by silica gel chromatography and/or recrystallization and stored indefinitely on the benchtop under air.

Figure 11:
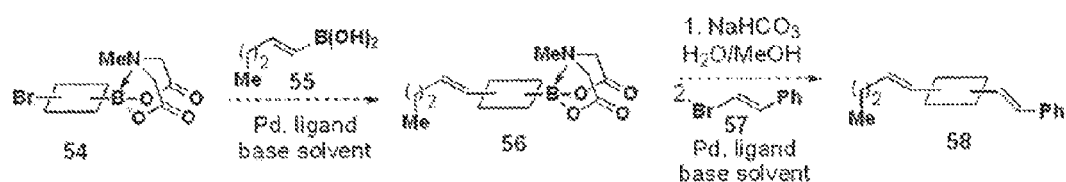
FIG. 11 represents a scheme for an example of the synthesis of polyenes.

FIG. 11 shows a scheme for an example of the general application of the iterative cross-coupling strategy to the synthesis of polyenes, including polyene natural products. A polyene is a compound that includes at least two alternating carbon-carbon double bonds. Cross-coupling of protected haloorganoboronic acid 54 with boronic acid 55 through the Suzuki-Miyaura reaction provides protected organoboronic acid 56. Deprotection of 56 provides the free boronic acid, which can be cross-coupled with an organohalide or organopseudohalide. If the organohalide or organopseudohalide includes a protected organoboronic acid, the polyene chain can be iteratively lengthened. In the example of FIG. 11, addition of organohalide 57 after the deprotection provides polyene product 58.

Figure 12:
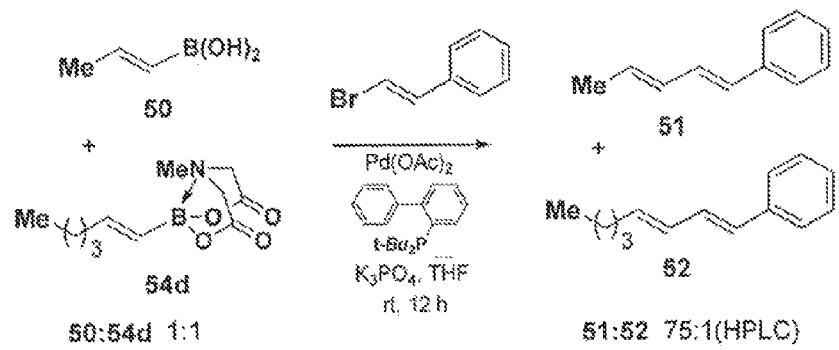
FIG. 12 represents an example of a reaction of protected and unprotected alkenyl organoboronic acids in a Suzuki-Miyaura transformation.

FIG. 12 shows chemical structures, reaction schemes and product ratios for an example of a reaction of protected and unprotected alkenylboronic acids in a Suzuki-Miyaura transformation. N-Methyliminodiacetic acid was complexed with 1-hexenyl boronic acid to generate previously unknown (N→B)-(1-hexenyl)-[N-methyliminodiacetate-O,N]borane 54*d*. This protected organoboronic acid was studied by temperature dependent $^1$H NMR (Mancilla, 2005), and the N→B bond was found to be stable up to at least 110° C. Stoichiometric quantities of 1-propylene boronic acid 50 and (N→B)-(1-hexenyl)-[N-methyliminodiacetate-O,O',N]borane 54*d* were reacted with 0.8 equiv. of β-bromostyrene under Suzuki-Miyaura cross-coupling conditions. A 75:1 mixture of products 51 and 52 was observed, consistent with a very high selectivity for coupling of the unprotected vinyl boronic acid 50.

Figure 13:
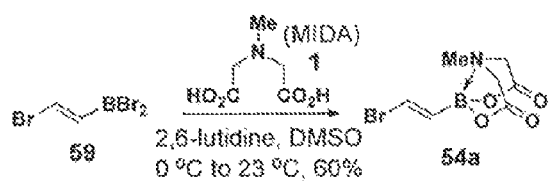
FIG. 13 represents an example of the formation of a protected haloorganoboronic acid.

FIGS. 13-18 shows chemical structures, reaction schemes and reaction yields for the preparation of protected haloorganoboronic acids 54*a*, 54*b* and 54*c*, and for subsequent reactions with 54*a* and 54*c*. Referring to FIG. 13, complexation of (E)-dibromo(2-bromovinyl)borane 59 with MIDA efficiently generated bifunctional olefin 54*a*. This reaction was reproduced on a 75 mmol scale to yield 12 g of 54a as a free-flowing crystalline solid that is stable to storage indefinitely under air. Experimental details are provided in Example 11.

Figure 14:
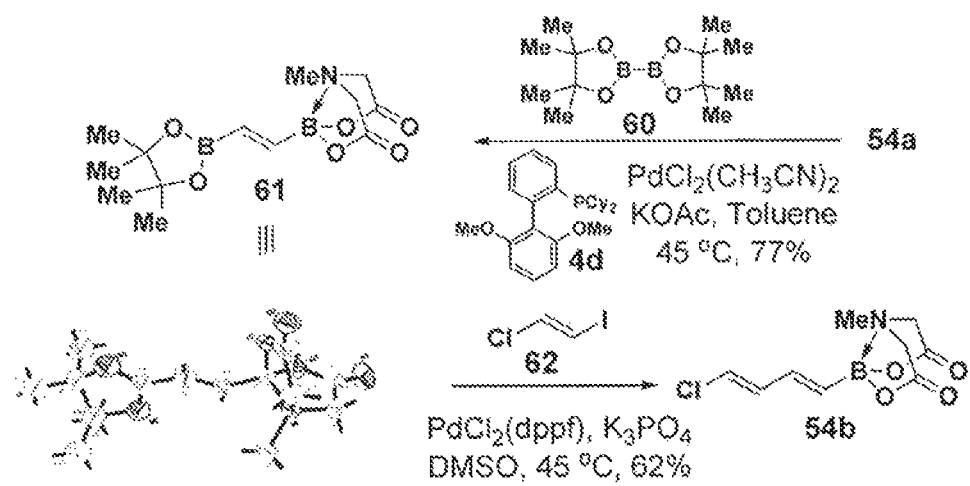
FIG. 14 represents an example of the formation of a protected haloorganoboronic acid.

Although Miyaura borylations with 1,2-disubstituted-vinyl halides are rare, 54a was converted smoothly into the novel bis-borylated olefin 61 (FIG. 14). An X-ray structure of 61 unambiguously confirmed the $sp^2$- and $sp^3$-hybridizations of the pinacol and MIDA boronate ester protecting groups, respectively. A subsequent doubly-selective (metal and halogen) Suzuki-Miyaura cross-coupling between 61 and (E)-1-iodo-2-chloroethylene 62 yielded the targeted diene 54b. This reaction demonstrated a selective cross-coupling with a differentially-ligated bis-boronate reagent. Experimental details are provided in Example 12.

Figure 15:
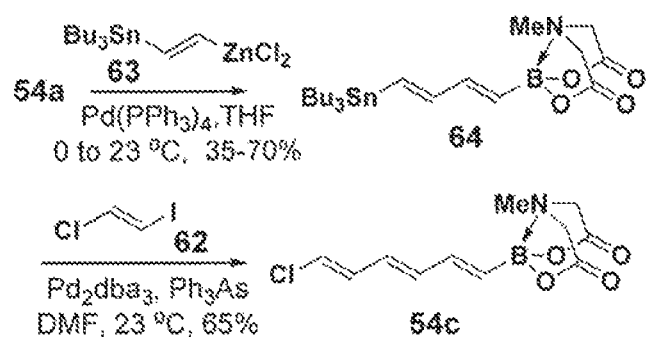
FIG. 15 represents an example of an iterative polyene synthesis using protected haloorganoboronic acids.
Figure 16:
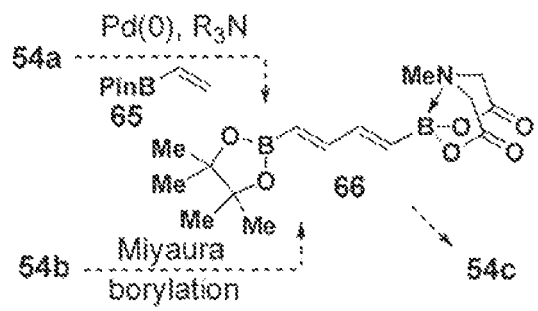
FIG. 16 represents an example of the formation of a protected haloorganoboronic acid.

Referring to FIG. 15, Negishi cross-coupling between 54a and the bis-metallated vinyl zinc 63 yielded the boronyl/stannyl diene 64. This reaction demonstrated a triply-metal selective (B, Sn, Zn) cross-coupling reaction. The targeted B-protected halotrienyl boronic acid 54c was prepared by a subsequent metal and halogen selective cross-coupling between 64 and 62. Experimental details are provided in Example 13.

Although this route was effective, organostannanes are toxic and it would be preferable to prepare 54c without the use of tin-containing intermediates. Thus, referring to FIG. 16, bis-borylated diene 66 will be synthesized as an alternative, tin-free intermediate for trienylchloride building block synthesis through Heck-type coupling between 54a and vinylpinacolboronic ester 65 or through Miyaura borylation of 54b.

Figure 17:
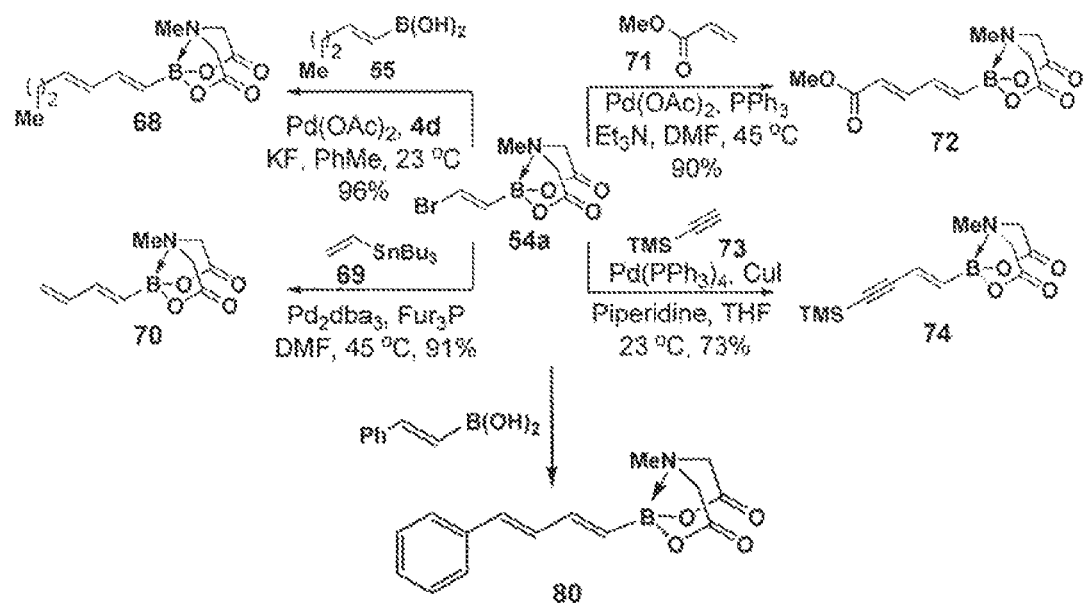
FIG. 17 represents a variety of chemical transformations of the organic group of an example of a protected haloorganoboronic acid.

Referring to FIG. 17, protected haloalkenylboronic acid 54a has undergone selective Suzuki-Miyaura, Stille, Heck, and Sonogashira couplings to generate products 68, 70, 72, and 74, respectively. Protected organoboronic acid 80 was the product of Suzuki-Miyaura cross-coupling. Experimental details are provided in Example 14.

Figure 18:
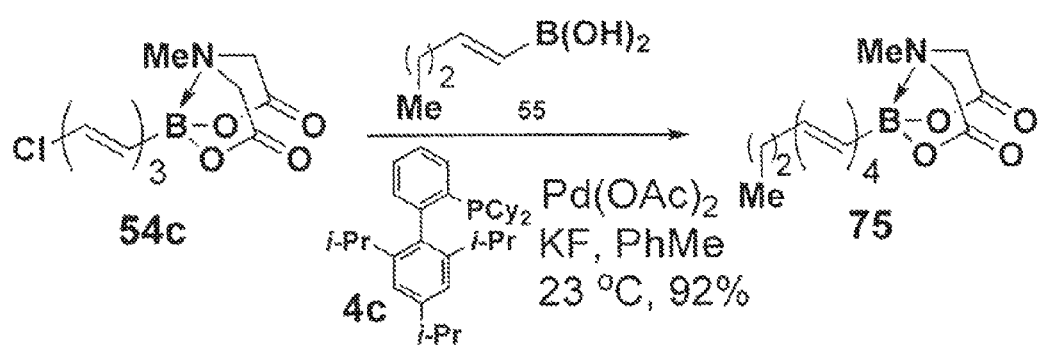
FIG. 18 represents an example of polyene synthesis using a protected haloorganoboronic acid.

Referring to FIG. 18, although cross-couplings with vinyl chlorides are relatively rare, using Buchwald's electron-rich and sterically bulky phosphine ligand 4c has provided a very efficient coupling between trienylchloride 54c and vinylboronic acid 55. Experimental details are provided in Example 15.

Figure 19:
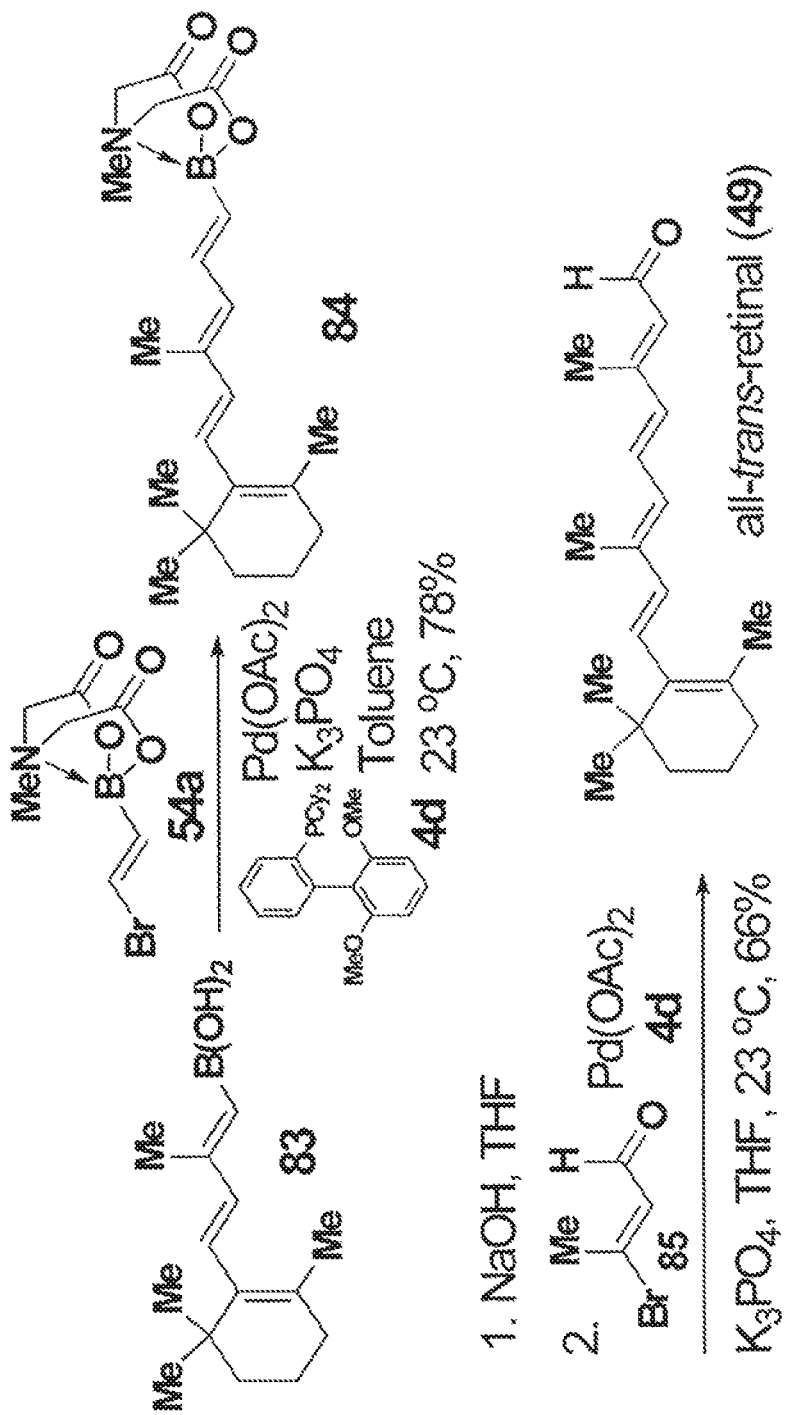
FIG. 19 represents chemical structures, reaction schemes and reaction yields for the synthetic steps in an example of the total synthesis of all-trans-retinal.

FIG. 19 shows chemical structures, reaction schemes and reaction yields for the synthetic steps in the total synthesis of all-trans-retinal. The known thienylboronic acid 83 (Uenishi, 2003) was selectively coupled with bifunctional building block 54a to yield tetraenylboronate ester 84. Surprisingly, although boronic acid 83 is unstable to concentration and storage, the more advanced MIDA boronate 84 was isolated as a crystalline solid via silica gel chromatography and was very stable to storage. A final sequence of boronic acid deprotection and cross-coupling with aldehyde 85 (Romo, 1998) yielded the natural product. Experimental details are provided in Example 16.

In contrast to most antibiotics which function via inhibition of mutable macromolecular targets and are thus very susceptible to microbial resistance, the antimycotic agent amphotericin B (AmB) operates via self-assembly with ergosterol in fungal lipid membranes to form permeabilizing ion channels. Because of this lack of a mutable protein target, resistance to this broad-spectrum antifungal agent is extremely rare despite more than four decades of widespread clinical use. However, due to competitive self-assembly with cholesterol to form related channels in human cells, AmB is also very toxic which often limits its clinical efficacy. The first, and at present only, reported total synthesis of AmB was accomplished by K. C. Nicolaou and coworkers in 1986. (Nicolaou, 1987; Nicolaou, 1988) This synthesis required 59 steps in the longest linear sequence, and some of the late-stage transformations proceeded in very low yield. In addition to these shortcomings, a lack of sufficient modularity and flexibility preclude the use of this synthesis for the practical preparation of structural derivatives of AmB.

Figure 20:
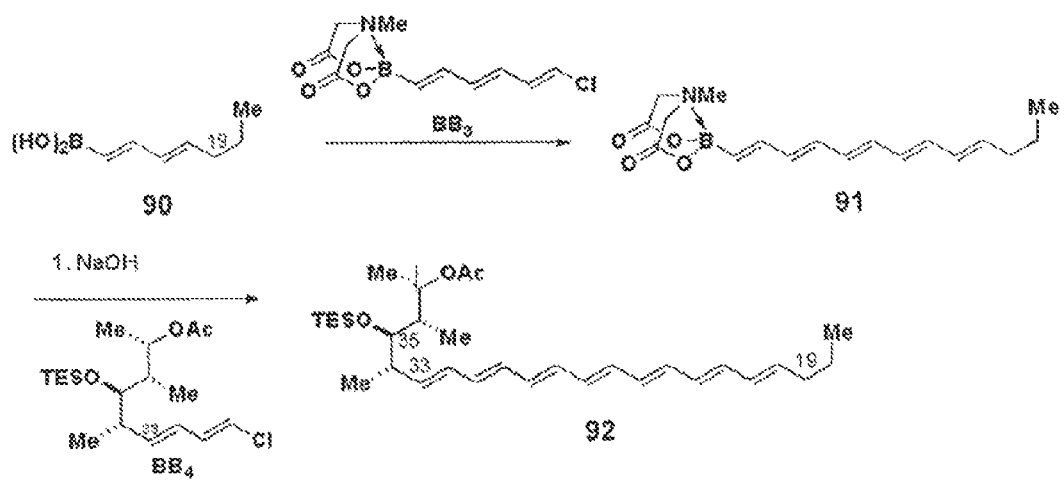
FIG. 20 represents structures and reaction schemes for the synthesis of half of the AmB skeleton.

FIG. 20 shows structures and reaction schemes for the synthesis of half of the AmB skeleton. Reaction of 1,3-hept-2-ene boronic acid 90 with $BB_3$ yielded protected organoboronic acid 91, in which the organic group is a polyene. Deprotection of 91 with sodium hydroxide produces the free boronic acid, which is reacted with $BB_4$ through a Suzuki-Miyaura cross-coupling reaction, yielding polyene 92. This product corresponds to half of the skeleton of AmB. Experimental details are provided in Example 17.

Another interesting polyene, β-parinaric acid 96, has been used for more than three decades as a fluorescent probe for membrane properties. In addition, related tetraenoic acids demonstrate remarkable aggregation behaviors including the formation of antipodal chiral aggregates from a single enantiomer. The utility of 96 and/or its analogs would benefit from more efficient and modular synthetic access to this class of compounds.

Figure 21:
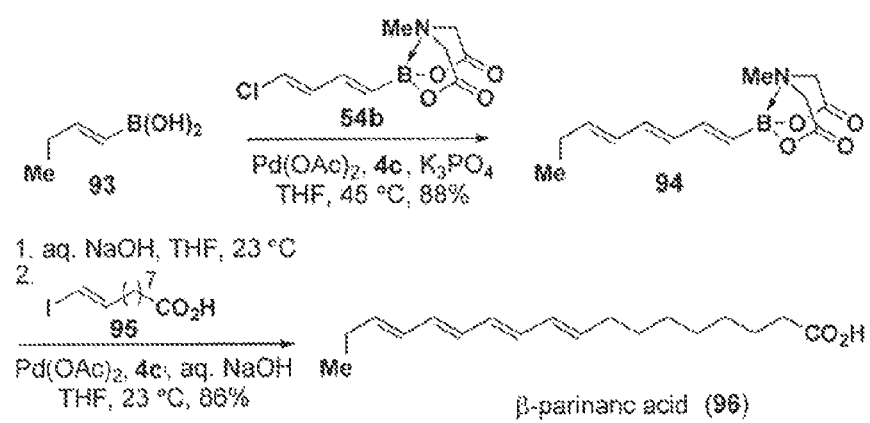
FIG. 21 represents structures and reaction schemes for the synthesis of β-parinaric acid.

FIG. 21 shows structures and reaction schemes for the synthesis of β-parinaric acid 96. The protected chlorodienylboronic acid 54b was employed in a modular, three-step synthesis of β-parinaic acid from readily-available starting materials. Specifically, using a modification of the newly identified conditions for polyenylchloride cross-coupling, a selective pairing between the bifunctional dienylchloride 54b and (E)-1-butenylboronic acid 93 yielded the all-trans trienyl boronate 94. This protected organoboronic acid was stable to purification by column chromatography. Deprotection of 94 was achieved under mild aqueous basic conditions, and subsequent cross-coupling with vinyl iodide 95 yielded β-parinaric acid 96 as a fluorescent solid. Experimental details are provided in Example 18.

Figure 22:
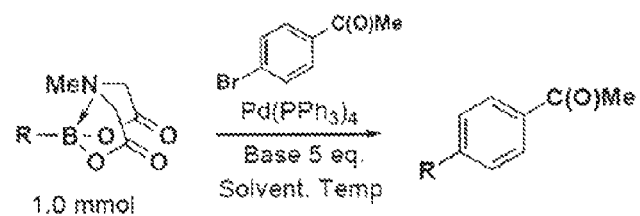
FIG. 22 represents chemical structures, reaction schemes and reaction yields for the in situ cross-coupling of protected organoboronic acids with an aryl halide.
Figure 22:
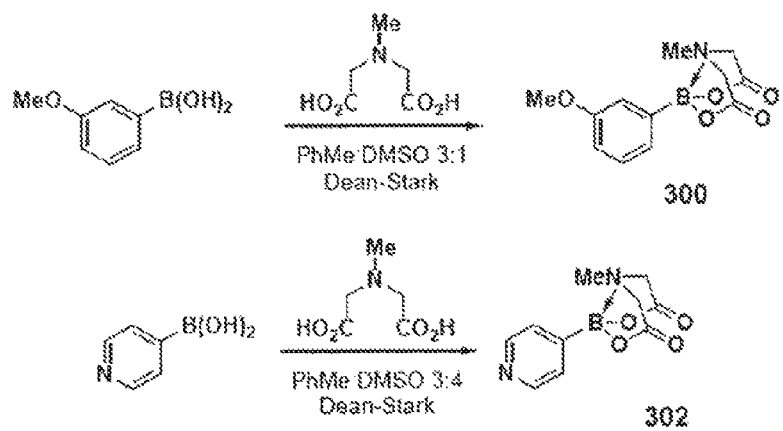

FIG. 22 shows chemical structures, reaction schemes and reaction yields for the in situ cross-coupling of protected organoboronic acids with an aryl halide. In this example, the protected organoboronic acids function as surrogates for the corresponding boronic acids. The corresponding boronic acid are difficult to purify. Experimental details are provided in Example 19.

The following examples are provided to illustrate one or more preferred embodiments of the invention. Numerous variations may be made to the following examples that lie within the scope of the invention.

EXAMPLES

General Methods

Commercial reagents were purchased from Sigma-Aldrich (St. Louis, Mo.), Fisher Scientific (Waltham, Mass.), Alfa Aesar/Lancaster Synthesis (Ward Hill, Mass.), or Frontier Scientific (Logan, Utah), and were used without further purification unless otherwise noted. N-Bromosuccinimide and 4-butylphenylboronic acid were recrystallized from hot water prior to use. Solvents were purified via passage through packed columns as described by Pangborn and coworkers (Pangborn, 1996) (THF, $Et_2O$, $CH_3CN$, $CH_2Cl_2$: dry neutral alumina; hexane, benzene, and toluene, dry neutral alumina and Q5 reactant; DMSO, DMF: activated molecular sieves). Water was double distilled. Triethylamine, diisopropylamine, diethylamine, pyridine, and 2,6-lutidine were freshly distilled under an atmosphere of nitrogen from $CaH_2$. Solutions of n-butyllithium were titrated according to the method of Hoye and coworkers (Hoye, T. R., 2004).

The following compounds were prepared according to literature precedent: N-isopropyliminodiacetic acid (Stein, A., 1995; Dubé, C. E., 2005), (E)-3-bromostyrylboronic acid (Perner, R. J., 2005), 5-bromo-2-benzofuranylboronic acid (Friedman, M. R., 2001), 2-bromo-5-methoxyphenol (Albert, J. S., 2002), 4-(methoxymethoxy)benzoic acid (Lampe, J. W., 2002), (E)-(2-bromoethenyl)dibromoborane (59) (Hyuga, S., 1987), (E)-1-chloro-2-iodoethylene (62) (Negishi, E. I., 1984; Organ, M. G., 2004), (1E,3E)-2-methyl-4-(2,6,6-trimethylcyclohex-1-enyl)buta-1,3-dienylboronic acid (83) (Uenishi, 2003), (E)-3-bromobut-2-enal (85) (Romo, 1998), (E)-2-(tributylstannyl)vinylzinc chloride (63) (Pihko, 1999), (E)-methyl 10-iododec-9-enoate (Zhang, 2006), diol $CH_3$—CH(OH)—CH($CH_3$)—CH(OH)—CH($CH_3$)—$CH_2$—O—$CH_2$—$C_6H_5$(Paterson, 2001), and dichloromethylpinacolboronic ester (Wuts, 1982; Raheem, 2004).

Suzuki-Miyaura cross-coupling reactions were typically performed under an atmosphere of argon in oven- or flame-dried I-Chem or Wheaton vials sealed with poly(tetrafluoroethylene)-lined plastic caps. All other reactions were performed in oven- or flame-dried round-bottom or modified Schlenk flasks fitted with rubber septa under a positive pressure of argon or nitrogen unless otherwise indicated. Organic solutions were concentrated via rotary evaporation under reduced pressure. Reactions were monitored by analytical thin layer chromatography (TLC) performed using the indicated solvent on E. Merck silica gel 60 F254 plates (0.25 mm). Compounds were visualized by exposure to a UV lamp ($\lambda$=254 nm), a glass chamber containing iodine, and/or a solution of $KMnO_4$, an acidic solution of p-anisaldehyde, or a solution of ceric ammonium molybdate (CAM) followed by brief heating using a Varitemp heat gun. Flash column chromatography was performed as described by Still and coworkers (Still, W. C., 1978) using EM Merck silica gel 60 (230-400 mesh).

$^1$H NMR spectra were recorded at 23° C. on one of the following instruments: Varian Unity 400, Varian Unity 500, Varian Unity Inova 500NB. Chemical shifts ($\delta$) are reported in parts per million (ppm) downfield from tetramethylsilane and referenced to residual protium in the NMR solvent ($CHCl_3$, $\delta$=7.26; $CD_2HCN$, $\delta$=1.93, center line) or to added tetramethylsilane ($\delta$=0.00). Data are reported as follows: chemical shift, multiplicity (s=singlet, d=doublet, t=triplet, q=quartet, sept=septet, m=multiplet, b=broad, app=apparent), coupling constant (J) in Hertz (Hz), and integration.

$^{13}$C NMR spectra were recorded at 23° C. on one of the following instruments: Varian Unity 500 or Varian Unity Inova 500NB. Chemical shifts ($\delta$) are reported in ppm downfield from tetramethylsilane and referenced to carbon resonances in the NMR solvent ($CDCl_3$, $\delta$=77.0, center line; $CD_3CN$, $\delta$=1.30, center line) or to added tetramethylsilane ($\delta$=0.00). Carbons bearing boron substituents were not observed (quadrupolar relaxation).

$^{11}$B NMR were recorded using a General Electric GN300WB instrument and referenced to an external standard of ($BF_3.Et_2O$). High resolution mass spectra (HRMS) were performed by Furong Sun and Dr. Steve Mullen at the University of Illinois School of Chemical Sciences Mass Spectrometry Laboratory. Infrared spectra were collected from a thin film on NaCl plates on a Mattson Galaxy Series FTIR 5000 spectrometer with internal referencing. Absorption maxima ($v_{max}$) are reported in wavenumbers ($cm^{-1}$). X-ray crystallographic analysis was carried out by Dr. Scott Wilson at the University of Illinois George L. Clark X-Ray facility.

Example 1: Preparation of Protected Organoboronic Acids Having Trivalent Groups

To form protected organoboronic acid 3a, a 500 mL flask was charged with p-tolylboronic acid (3.00 g, 22.1 mmol, 1 equiv.), N-methyliminodiacetic acid (3.25 g, 22.1 mmol, 1 equiv.), benzene (360 mL) and DMSO (40 mL). The flask was fitted with a Dean-Stark trap and a reflux condenser, and the mixture was refluxed with stirring for 16 h followed by concentration in vacuo. The resulting crude product was adsorbed onto Florisil gel from a MeCN solution. The resulting powder was dry-loaded on top of a silica gel column slurry-packed with EtOAc. The product was eluted using a gradient (EtOAc→EtOAc:MeCN 2:1) to yield boronate ester 3a as a colorless, crystalline solid (5.05 g, 93%). An x-ray structure of 3a is shown in FIG. 3.

To form protected organoboronic acid 3c, a 250 mL roundbottom flask was charged with p-tolylboronic acid (7.36 mmol, 1.00 g), N-isopropyliminodiacetic acid (7.36 mmol, 1.29 g), benzene (150 mL) and DMSO (15 mL). The flask was fitted with a Dean-Stark trap and a reflux condenser, and the mixture was refluxed with stirring for 14 h and then concentrated in vacuo. Purification by flash chromatography ($Et_2O$→$Et_2O$:MeCN 1:2) yielded boronate ester 3c as a colorless, crystalline solid (747 mg, 37%).

To form protected organoboronic acid 3d, a 100 mL roundbottom flask was charged with p-tolylboronic acid (3.68 mmol, 500 mg), N-methyldiethanolamine (3.68 mmol, 422 µL) and toluene (70 mL). The flask was fitted with a Dean-Stark trap and a reflux condenser, and the solution was refluxed with stirring for 8 h and then allowed to cool to 23° C. $CaCl_2$ (app. 200 mg, a fine powder) and $NaHCO_3$ (app. 200 mg) were then added, and the resulting mixture was stirred for 15 min. and then was filtered. The filtrate was concentrated in vacuo and residual solvent was removed via co-evaporation with $CH_2Cl_2$ to yield boronate ester 3d as a colorless, crystalline solid (399 mg, 50%).

Example 2: Reactivity Studies of Unprotected Organoboronic Acids and Protected Organoboronic Acids Having Trivalent Groups The reactivity studies of the compounds of Example 1 were carried out as follows. In a glove box, to a vial equipped with a small stir bar and containing the 2-(di-tert-butylphosphino)biphenyl ligand was added a 0.02 M solution of Pd(OAc)$_2$ in THF in a volume sufficient to yield a 0.04 M solution with respect to the phosphine ligand. The vial was sealed with a PTFE-lined cap, removed from the glove box, and maintained at 65° C. with stirring for 30 min to provide the catalyst stock solution.

In a glove box, a glass vial equipped with a small stir bar was charged with boronate ester 3 (0.06 mmol) and anhydrous $K_3PO_4$ as a finely ground powder (32 mg, 0.15 mmol). To this vial was then added a 250 µL of a THF solution of 4-butylphenylboronic acid (0.24 M, 0.06 mmol), 4-bromobenzaldehyde (0.20 M, 0.05 mmol) and biphenyl (0.08 M, internal std, for HPLC analysis). Finally, to this same vial was added 50 µL of the catalyst stock solution described above. The vial was then sealed with a PTFE-lined cap, removed from the glove box, and maintained in a 65° C. oil bath with stirring for 12 h. The reaction solution was then allowed to cool to 23° C. and filtered through a plug of silica gel, eluting with MeCN:THF 1:1. The filtrate was then analyzed by HPLC. For The ratio of products 5 and 6 was determined using an HPLC system (Agilent Technologies) fitted with a Waters SunFire Prep $C_{18}$ 5 µm column (10×250 mm, Lot No. 156-160331) with a flow rate of 4 mL/min and a gradient of MeCN:$H_2O$ 5:95→95:5 over 23 min., with UV detection at 268 nm (4-bromobenzaldehyde, $t_R$=14.66 min.; biphenyl, $t_R$=21.80 min.) and 293 nm (5, $t_R$=25.79 min.; 6, $t_R$=20.50 min.; it was determined that the absorption coefficients for 5 and 6 at 293 nm were identical within the limits of experimental error).

The reaction and characterization were carried out for protected organoboronic acids 3a, 3b, 3c and 3d. For each species, the starting concentration of the protected organoboronic acid was 0.06 mmol. The reaction was carried out 3 times, and the product ratios were averaged. The reaction of 3a yielded a 24:1.0 ratio of 5:6 The reaction of 3b yielded a 1.0:1.0 ratio of 5:6. The reaction of 3c yielded a 26:1.0 ratio of 5:6. The reaction of 3d yielded a 1.0:1.0 ratio of 5:6. These results are listed in FIG. 4.

Example 3: Preparation of Halogen-Functionalized Protected Organoboronic Acids

The general method for synthesizing protected haloorganoboronic acids was as follows. A roundbottom flask equipped with a stir bar was charged with haloboronic acid (1 equiv.), N-methyliminodiacetic acid (1-1.5 equiv.), and benzene:DMSO (10:1). The flask was fitted with a Dean-Stark trap and a reflux condenser, and the mixture was refluxed with stirring for 12-18 hours. The reaction solution was allowed to cool to 23° C. and the solvent was removed in vacuo. The resulting crude solid was absorbed onto Florisil gel from a MeCN solution. The resulting powder was dry-loaded on top of a silica gel column slurry-packed with $Et_2O$. The column was flushed with a copious volume of $Et_2O$; the product was then eluted with a mixture of $Et_2O$:MeCN. All products thus obtained were analytically pure, colorless, crystalline solids that were indefinitely bench stable at 23° C. under air. Yields are given below and in FIG. 5.

For protected haloorganoboronic acid 8a, the general procedure was followed using 4-bromophenylboronic acid (1.00 g, 4.98 mmol, 1 equiv.), N-methyliminodiacetic acid (733 mg, 4.98 mmol), benzene (150 mL) and DMSO (15 mL). The mixture was refluxed for 12 h. The product was eluted using a gradient; $Et_2O$→$Et_2O$:$CH_3CN$ 1:1. Compound 8a was isolated as an analytically pure, colorless, crystalline solid (1.53 g, 98%).

For protected haloorganoboronic acid 8b, the general procedure was followed using 3-bromophenylboronic acid (2.00 g, 9.96 mmol), N-methyliminodiacetic acid (1.47 g, 9.96 mmol), benzene (300 mL) and DMSO (30 mL). The mixture was refluxed for 18 h. The product was eluted with $Et_2O$:$CH_3CN$ 1.1. Compound 8b was isolated as an analytically pure, colorless, crystalline solid (2.89 g, 93%).

For protected haloorganoboronic acid 8c, the general procedure was followed using 2-bromophenylboronic acid (2.00 g, 9.96 mmol), N-methyliminodiacetic acid (1.47 g, 9.96 mmol), benzene (300 mL) and DMSO (30 mL). The mixture was refluxed for 13 h. The product was eluted with $Et_2O$:MeCN 1:1. Compound 8c was isolated as an analytically pure, colorless, crystalline solid (3.01 g, 97%).

For protected haloorganoboronic acid 8d, the general procedure was followed using 4-bromothiophene-2-boronic acid (281 mg, 1.36 mmol). N-methyliminodiacetic acid (240 mg, 1.63 mmol), benzene (50 mL) and DMSO (5 mL). The mixture was refluxed for 13 h. The product was eluted with $Et_2O$:MeCN 3:1. Compound 8d was isolated as an analytically pure, colorless, crystalline solid (429 mg, 99%).

For protected haloorganoboronic acid 8e, the general procedure was followed using 2-(3-bromophenyl)ethenylboronic acid (227 mg, 1.0 mmol), N-methyliminodiacetic acid (147 mg, 1.0 mmol), benzene (50 mL) and DMSO (5 mL). The mixture was refluxed for 11 h. The product was eluted with $Et_2O$:MeCN 5:1. Compound 8e was isolated as an analytically pure, colorless, crystalline solid (334 mg, 99%).

For protected haloorganoboronic acid 8f, the initial unprotected boronic acid, 2-(3-bromophenyl)cyclopropylboronic acid, was formed from compound 8e. To a stirred solution of 8e (1.21 g, 3.59 mmol) and Pd(OAc)$_2$ (0.0239 g, 0.11 mmol) in THF (24 mL) at 0° C. in a 250 mL Schlenk flask was added a freshly prepared ethereal solution of diazomethane (35 mL of a 0.25 M solution, 8.8 mmol) dropwise over 20 minutes. Additional Pd(OAc)$_2$ was then added (0.0239 g, 0.11 mmol) as a solution in THF (1 mL) followed by the dropwise addition over 20 min of an additional 35 mL of 0.25 M ethereal diazomethane (8.8 mmol). The reaction was then allowed to warm to 23° C. and the excess diazomethane was removed under a stream of $N_2$. The crude reaction mixture was then poured into 120 mL of 0.5 M pH 7 sodium phosphate buffer and extracted with THF:$Et_2O$ 1:1 (3×120 mL). The combined organic fractions were then washed with brine, dried over $Na_2SO_4$, and concentrated in vacuo. Purification by flash chromatography (SiO$_2$, $Et_2O$→$Et_2O$: $CH_3CN$ 1:1) yielded 8f (1.21 g, 96%). To a stirred solution of 8f (0.513 g, 1.46 mmol) in THF (20 mL) was added 1M aq. NaOH (4.37 mL, 4.37 mmol) and the resulting mixture was stirred at 23° C. for 20 minutes. The reaction was then quenched with the addition of 0.5 M pH 7 phosphate buffer (20 mL) and diluted with $Et_2O$ (20 mL). The layers were separated and the aqueous layer was extracted with THF: $Et_2O$ 1:1 (40 mL). The combined organic fractions were dried over MgSO$_4$ and concentrated in vacuo to yield the desired 2-(3-bromophenyl) cyclopropylboronic acid as a colorless solid (0.339 g, 97%).

Although 8f was formed as an intermediate to 2-(3-bromophenyl) cyclopropylboronic acid, the compound could also be formed by reaction of 2-(3-bromophenyl) cyclopropylboronic acid with N-methyliminodiacetic acid. In this case, the general procedure was followed using 2-(3-bromophenyl) cyclopropylboronic acid (316 mg, 1.31 mmol), N-methyliminodiacetic acid (232 mg, 1.58 mmol), benzene (50 mL) and DMSO (5 mL). The mixture was refluxed for 6 h. The product was eluted with MeCN:$Et_2O$ 5:1. Compound 8f was isolated as an analytically pure, colorless solid (408 mg, 88%).

Example 4: Reaction of Protected Organoboronic Acids Containing Halogen Groups in the Suzuki-Miyaura Reaction The reactivity studies of the compounds of Example 3 were carried out as follows. In a glove box, to a vial equipped with a stir bar was added the phosphine ligand. To the vial was then added a 0.02 M solution of Pd(OAc)$_2$ in THF in a volume sufficient to yield a 0.04 M solution with respect to the phosphine ligand. The vial was sealed with a PTFE-lined cap, removed from the glove box, and maintained at 65° C. with stirring for 30 min to provide the catalyst stock solution.

To a 40 mL vial equipped with a stir bar was added the haloboronate ester of Example 3 (1.0 mmol) and the boronic acid (typically 1.2-1.5 mmol). The vial was brought into the glove box. To the vial was added $K_3PO_4$ (3.0 mmol, 636.8 mg, a finely ground powder). THF (9.0 mL), and then the catalyst stock solution (1.0 mL). The vial was capped with a PTFE-lined cap, removed from the glove box, and placed in a 65° C. oil bath with stirring for 12 h. The reaction mixture was allowed to cool to 23° C. and then filtered through a very thin pad of silica gel topped with sand and then celite, eluting with a copious volume of MeCN. To the resulting solution was added Florisil gel (app. 25 mg/mL of solution), and then solvent was removed in vacuo. The resulting powder was dry-loaded on top of a silica gel column slurry-packed with $Et_2O$. The column was flushed with a copious volume of $Et_2O$; the product was then eluted with $Et_2O$:MeCN. Reaction yields are listed in FIG. 6.

For protected organoboronic acid 9a, the general procedure was followed using 8a (312 mg, 1.00 mmol), tolylboronic acid (163 mg, 1.20 mmol), and 2-(dicyclohexylphosphino)biphenyl. The product was eluted with $Et_2O$:MeCN 1:1. Compound 9a was isolated as a colorless solid (280 mg, 87%). This same reaction was also set up using standard Schlenk techniques without the use of a glove box. A flame-dried 25 mL Schlenk flask equipped with a stir bar was evacuated and purged with argon 3 times. This flask was charged with 2-(dicyclohexylphosphino)-biphenyl (14.1 mg, 0.04 mmol) $Pd(OAc)_2$ (4.4 mg, 0.02 mmol), and THF (10 mL). The flask was then fitted with a reflux condenser and the yellow solution was heated to reflux for 5 minutes resulting in discoloration. A separate flame-dried 25 mL Schlenk flask equipped with a stir bar was evacuated and purged with argon 3 times. This flask was charged with haloboronate ester 8a (312.1 mg, 1.00 mmol), tolylboronic acid (163.2 mg, 1.20 mmol), and freshly ground anhydrous $K_3PO_4$ (637.2 mg, 3.00 mmol). This flask was then fitted with a reflux condenser. The catalyst solution was then transferred via cannula into the flask containing the coupling partners and base. The resulting mixture was heated at reflux for 12 hours. The reaction was worked-up as described in the general procedure above. The product was eluted with $Et_2O$:MeCN 3:1→1:1. Compound 9a was isolated as a nearly colorless solid (279.6 mg, 87%).

For protected organoboronic acid 9b, the general procedure was followed using 8b (312 mg, 1.00 mmol), tolylboronic acid (163 mg, 1.20 mmol), and 2-(dicyclohexylphosphino)biphenyl. The product was eluted with $Et_2O$:MeCN 1:1. Compound 9b was isolated as a colorless, crystalline solid (276 mg, 85%).

For protected organoboronic acid 9c, the general procedure was followed using 8c (312 mg, 1.00 mmol), tolylboronic acid (172 mg, 2.00 mmol) and 2-(dicyclohexylphosphino)biphenyl. The product was eluted with a gradient of $Et_2O$:MeCN 5:1→1:1. Compound 9c was isolated as a pale yellow solid (257 mg, 80%).

For protected organoboronic acid 9d, the general procedure was followed using 8d (318 mg, 1.00 mmol), tolylboronic acid (204 mg, 1.50 mmol), $K_2CO_3$ (415 mg, 3.00 mmol,) and 2-(dicyclohexylphosphino)-2',4',6'-tri-isopropyl-1,1'-biphenyl. The product was eluted using a gradient of $Et_2O$:MeCN 5:1→3:1. Compound 9d was isolated as a pale yellow solid (266 mg, 81%).

For protected organoboronic acid 9e, the general procedure was followed using 8e (338 mg, 1.00 mmol), tolylboronic acid (163 mg, 1.20 mmol), and 2-(dicyclohexylphosphino)biphenyl. The product was eluted with $Et_2O$:MeCN 5:1. Compound 9e was isolated as an off-white solid (282 mg, 82%).

For protected organoboronic acid 9f, the general procedure was followed using 8f (237 mg, 0.674 mmol), tolylboronic acid (109 mg, 0.808 mmol), $K_3PO_4$ (429 mg, 2.02 mmol), catalyst stock solution containing 2-(dicyclohexylphosphino) biphenyl (674 µL), and THF 6.06 mL. The product was eluted with $Et_2O$:MeCN (1:1). Compound 9f was isolated as an off-white crystalline solid (229 mg, 94%).

Example 5: Deprotection of Protected Organoboronic Acids

The general method for deprotecting the protected organoboronic acids of Example 4 was as follows. A round bottom flask equipped with a stir bar was charged with the boronate ester (1 equiv.), THF (10 mL), and 1M aq. NaOH (3 equiv.) and the resulting mixture was vigorously stirred at 23° C. for 10 minutes. The reaction mixture was then diluted with aq. sodium phosphate buffer (0.5 M, pH 7.0, 10 mL) and $Et_2O$ (10 mL), the layers were separated, and the aq. phase was extracted once with THF:$Et_2O$ 1:1 (20 mL). (On some occasions phosphate salts precipitated and during the extraction process and were redissolved by the addition of water. The combined organic fractions were then dried over $MgSO_4$ and concentrated in vacuo. Residual solvent was co-evaporated with MeCN. Reaction yields are listed in FIG. 6

For organoboronic acid 10a, the general procedure was followed using 9a (261 mg, 0.806 mmol) and 1 M aq. NaOH (2.42 mL, 2.42 mmol). Compound 10a was isolated as a white solid (147.4 mg, 86%).

For organoboronic acid 10b, the general procedure was followed using 9b (268 mg, 0.830 mmol) and 1 M aq. NaOH (2.49 mL, 2.49 mmol). Compound 10b was isolated as a white solid (161 mg, 92%).

For organoboronic acid 10c, the general procedure was followed using 9c (236 mg, 0.729 mmol) and 1M aq. NaOH (2.19 mL, 2.19 mmol). Compound 10c was isolated as a white solid (150 mg, 97%). In another approach, hydrolysis was performed with $NaHCO_3$ instead of NaOH. This deprotection was carried out as follows. To a 40 mL I-Chem vial equipped with a stir bar and containing 8c (0.672 mmol, 217 mg) was added MeOH (7 mL) and sat. aq. $NaHCO_3$ (3.5 mL). The mixture was vigorously stirred for 6 h at 23° C. The mixture was then diluted with saturated aq. $NH_4Cl$ (7 mL) and $Et_2O$ (14 mL), and the phases were separated. The aqueous phase was twice extracted with $Et_2O$ (14 mL), and the combined organics were dried over $MgSO_4$ and concentrated in vacuo. The residue was twice suspended in MeCN followed by concentration in vacuo and then dissolved in $CH_2Cl_2$ and concentrated in vacuo to yield 10c as a colorless, crystalline solid (121 mg, 85%).

For organoboronic acid 10d, the general procedure was followed using 9d (226 mg, 0.686 mmol) and 1 M aq. NaOH (2.06 mL, 2.06 mmol). Compound 10d was isolated as a pale green solid (131 mg, 88%).

For organoboronic acid 10e, the general procedure was followed using 9d (243 mg, 0.696 mmol) and 1 M aq. NaOH (2.09 mL, 2.09 mmol). Compound 10e was isolated as an off-white solid (138 mg, 83%).

For organoboronic acid 10f, the general procedure was followed using 9f (202 mg, 0.56 mmol) and 1M aq NaOH (1.67 mL, 1.67 mmol). Compound 10f was isolated as an off-white solid (127 mg, 91%).

Example 6: Preparation of Protected Organoboronic Acid for Use in Total Synthesis of Ratanhine Protected haloorganoboronic acid 13 was synthesized by the general procedure of Example 3, using 5-bromo-2-benzofuranylboronic acid (Friedman, M. R., 2001) (1.33 g, 5.50 mmol), N-methyliminodiacetic acid (970 mg, 6.60 mmol), benzene (80 mL) and DMSO (8 mL). The mixture was refluxed for 13 h. The product was eluted using a gradient of $Et_2O$:MeCN 1:1→1:2. Compound 13 was isolated as an analytically pure, off-white, crystalline solid (1.73 g, 90%).

Example 7: Preparation of Protected Organoboronic Acid for Use in Total Synthesis of Ratanhine Protected haloorganoboronic acid 14 was synthesized by a multi-step process. To a stirred mixture of 2-bromo-5-methoxyphenol (Albert, 2002) (2.19 g, 10.8 mmol) and $K_2CO_3$ (4:46 g, 32.3 mmol) in acetone (55 mL) was added chloromethyl methyl ether (1.63 mL, 21.5 mmol). The mixture was refluxed for 3 h and then allowed to cool to 23° C. The mixture was filtered and the filtrate was concentrated in vacuo. The crude product was then purified by flash chromatography ($SiO_2$, hexanes:EtOAc 95:5) to provide 2-bromo-5-methoxy-1-methoxymethoxybenzene as a colorless liquid (2.43 g, 92%):

To a stirred solution of 2-bromo-5-methoxy-1-methoxymethoxybenzene (1.04 g, 4.23 mmol) in THF (13 mL) at −95° C. (hexanes/$N_2$) was added n-BuLi (1.6 M in hexanes, 2.91 mL, 4.65 mmol) and the resulting solution was stirred for 5 min. To this solution was then added by syringe a solution of $I_2$ (1.28 g, 5.07 mmol) in THF (8.5 mL) until a yellow color persisted. The solution was then permitted to warm to 23° C. and concentrated in vacuo. The residue was purified by flash chromatography ($SiO_2$, petroleum ether:$Et_2O$ 8:1) to provide 2-iodo-5-methoxy-1-methoxymethoxybenzene as a pale-orange oil (1.04 g, 84%). See also Tsukayama, M., 1997.

To a stirred solution of 2-iodo-5-methoxy-1-methoxymethoxybenzene (5.24 g, 17.8 mmol) in MeCN (55 mL) was added silica gel (1.32 g), 2,6-di-tert-butyl-4-hydroxytoluene (60 mg), and then N-bromosuccinimide (3.17 g, 17.8 mmol). The mixture was stirred at 23° C. for 1 hour and then filtered. The filtrate was concentrated in vacuo and the residue was dissolved in $CH_2Cl_2$ (100 mL). To this solution was added water (100 mL) and the resulting mixture was vigorously stirred for 5 min. The layers were then separated and the aq. phase was extracted with $CH_2Cl_2$ (2×100 mL). The combined organics were dried over $MgSO_4$ and concentrated in vacuo. The residue was purified by flash-column chromatography ($SiO_2$, petroleum ether: $Et_2O$ 8:1) to provide 2-iodo-4-bromo-5-methoxy-1-methoxymethoxybenzene as a yellow oil (5.05 g, 76%).

In a glove box, to a 40 mL I-Chem vial equipped with a stir bar and containing 2-iodo-4-bromo-5-methoxy-1-methoxymethoxybenzene (500 mg, 1.34 mmol) was added potassium acetate (395 mg, 4.02 mmol), bis(neopentylglycolato)diboron (363 mg, 1.61 mmol) and $PdCl_2$(dppf) (33 mg, 0.040 mmol). The vial was sealed with a septum cap and then removed from the glove box. To the vial was then added DMSO (11 mL) and the resulting mixture was sealed under an atmosphere of argon and stirred at 80° C. for 13 h. The mixture was then allowed to cool to 23° C. and 1 M aq. NaOH was added (0.9 mL, 0.9 mmol). The mixture was stirred at 23° C. for 10 minutes and then diluted with saturated aq. $NH_4Cl$ (50 mL), water (50 mL), and $Et_2O$ (100 mL). The layers were separated and the organic phase was washed with water (3×100 mL), dried over $MgSO_4$, and concentrated in vacuo. The residue was thrice dissolved in MeCN and concentrated in vacuo to afford a crude sample of 2-methoxymethoxy-4-methoxy-5-bromophenyl boronic acid as a light brown solid (343 mg): TLC (EtOAc) $R_f$=0.50, stained by $KMnO_4$; $^1$H-NMR (400 MHz, $CDCl_3$) δ 7.97 (s, 1H), 6.75 (s, 1H), 5.97 (s, 2H), 5.29 (s, 2H), 3.91 (s, 3H), 3.52 (s, 3H). To this crude boronic acid dissolved in benzene:DMSO (10:1) was added N-methyliminodiacetic acid (210 mg, 1.43 mmol). The flask was fitted with a Dean-Stark trap and a reflux condenser and the mixture was refluxed with stirring for 11 h followed by concentration in vacuo. The resulting crude product was adsorbed onto Florisil gel from a MeCN solution. The resulting powder was dry-loaded on top of a silica gel column slurry-packed with $Et_2O$. The column was flushed with a copious volume of $Et_2O$ and then the product was eluted with $Et_2O$:MeCN 1:1 to yield building block 14 as an off-white solid (365 mg, 68% yield over two steps).

Example 8: Preparation of Haloorganic Compound for Use in Total Synthesis of Ratanhine Haloorganic compound 15 was synthesized by a multi-step process. To a mixture of methyltriphenylphosphonium bromide (14.08 g, 39.4 mmol) in toluene at 23° C. was added a solution of potassium tert-butoxide (4.47 g, 39.8 mmol) in THF (60 mL) dropwise via cannula, and the resulting mixture was allowed to stir at 23° C. for 4 hours. The resulting yellow mixture was cooled to −78° C. and a solution of 4-iodo-salicylaldehyde (4.35 g, 17.5 mmol) in toluene (40 mL) was added dropwise via cannula. The resulting mixture was allowed to slowly warm to 23° C. and was stirred at that temperature for 12 hours. The reaction was then quenched with the addition of saturated aq. ammonium chloride (100 mL). The resulting mixture was then diluted with water (200 mL) and extracted with $Et_2O$ (3×100 mL). The combined organic fractions were then washed with brine (100 mL), dried over magnesium sulfate, and concentrated in vacuo. Purification by flash chromatography ($SiO_2$, hexanes:ethyl acetate 7:1→1:1) yielded 2-hydroxy-5-iodostyrene as a colorless solid (4.0 g, 98%). See also Gligorich, K. M., 2006.

To a stirred solution of 2-hydroxy-5-iodostyrene, 4-(methoxymethoxy)benzoic add, and DCC in methylene chloride at 23° C. was added DMAP, and the resulting mixture was stirred at 23° C. for 21 hours. The reaction mixture was then filtered over celite and concentrated in vacuo. Purification by flash chromatography ($SiO_2$, hexanes: ethyl acetate 5:1) yielded (2-vinyl-4-iodophenyl)-4-methoxymethoxybenzoate as a colorless solid (4.6 g, 79%).

To a stirred solution of (2-vinyl-4-iodophenyl)-4-methoxymethoxybenzoate (azeotropically dried with 2×50 mL benzene) in methylene chloride at 0° C. was added bromine dropwise via syringe over 5 minutes. The resulting solution was stirred at 0° C. for an additional 5 minutes and then concentrated in vacuo at 0° C. over 30 min. Residual bromine was removed via co-evaporation with 3×15 mL of methylene chloride at 0° C. The resulting crude product mixture was then purified by flash chromatography ($SiO_2$, hexanes:ethyl acetate 5:1→2:1) to yield (2-(1,2-dibromoethyl)-4-iodophenyl)-4-methoxymethoxybenzoate as a colorless solid (3.7 g, 59%).

To a stirred solution of (2-(1,2-dibromoethyl)-4-iodophenyl)-4-methoxymethoxybenzoate (3.61 g, 6.33 mmol, azeotropically dried with acetonitrile) in acetonitrile (75 mL) at 23° C. was added DBU (1.928 g, 12.7 mmol, 2.0 eq.) dropwise via syringe over 2 minutes. The resulting mixture was stirred at 23° C. for 25 min. The reaction was then quenched with the addition of 1 M aq. HCl (200 mL) and the resulting mixture was extracted with ethyl acetate (1×200 mL and 2×125 mL). The combined organic fractions were washed with brine (100 mL), dried over magnesium sulfate, and concentrated in vacuo. Flash chromatography (SiO$_2$, petroleum ether:Et$_2$O 3:1) yielded (2-(1-bromoethenyl)-4-iodophenyl)-4-methoxymethoxybenzoate as a colorless oil (3.01 g, 97%).

In a glove box, to a 40 mL I-Chem vial equipped with a stir bar and containing (2-(1-bromoethenyl)-4-iodophenyl)-4-methoxymethoxybenzoate (0.8695 g, 1.78 mmol; azeotropically-dried with 3×5 mL benzene) was added K$_3$PO$_4$ (0.7548 g, 3.56 mmol), propenylboronic acid (0.183 g, 2.13 mmol) as a solution in THF (3.6 mL), and PdCl$_2$dppf (72.6 mg, 0.09 mmol) as a solid. An additional 6.8 mL of THF was added and the resulting mixture was sealed with a PTFE-lined cap and maintained at 65° C. with stirring for 15 hours. The reaction mixture was then allowed to cool to 23° C., quenched with the addition of 1 M pH 7 phosphate buffer (60 mL), and extracted with diethyl ether (3×60 mL). The combined organic fractions were then washed with water (20 mL) and brine (40 mL), dried over MgSO$_4$, and concentrated in vacuo. Flash chromatography (SiO$_2$, toluene) yielded haloorganic compound 15 as a colorless oil (0.4994 g, 1.24 mmol, 70%).

Example 9: Total Synthesis of Ratanhine Using Iterative Suzuki-Miyaura Reactions Suzuki-Miyaura coupling reactions were performed with 15 and with protected haloorganoboronic acids 13 and 14, using the general procedure of Example 4. The reaction scheme and yields are given in FIG. 10. In the first step, the reactants were 13 (352 mg, 1.00 mmol) and (E)-1-propenylboronic acid (144 mg, 2.00 mmol). The product was eluted using a gradient of Et$_2$O:MeCN 10:1→1:1. The desired product 16 was isolated as a colorless crystalline solid (251 mg, 80%).

The general procedure for deprotection of boronate esters of Example 5 was followed using 16 (313 mg, 1.00 mmol), and 1 M eq. NaOH (3.0 mL, 3.0 mmol) to afford the free boronic acid as an off-white solid (188 mg, 93%); TLC: (EtOAc) R$_f$=0.2, visualized by UV; HRMS (EI+): Calculated for C$_{11}$H$_{11}$O$_{13}$B (M)$^+$ 202.0801. Found 202.0805. The free boronic acid was found to be very sensitive to decomposition upon storage and was therefore used immediately in the next reaction. In a glove box, to a 40 mL I-Chem vial containing 14 (141 mg, 0.351 mmol) was added the free boronic acid (106 mg, 0.526 mmol) as a solution in THF (3.15 mL) followed by solid K$_2$CO$_3$ (145 mg, 1.05 mmol). To the vial was then added 350 µL of a THF catalyst stock solution containing 2-(dicyclohexylphosphino) biphenyl (0.04 M) and Pd$_2$dba$_3$ (0.01 M), which was preincubated at 65° C. for 30 min. with stirring. The vial was sealed with a PTFE-lined cap, removed from the glove box, and maintained at 80° C. with stirring for 28 h. The reaction mixture was allowed to cool to 23° C., and was then passed through a thin pad of silica get topped with Celite, eluting with a copious volume of Et$_2$O. The filtrate was concentrated in vacuo and the resulting crude product was adsorbed onto Florisil gel from a MeCN solution. The resulting powder was dry-loaded on top of a silica gel column slurry-packed with Et$_2$O. The column was flushed with a copious volume of Et$_2$O: the product was then eluted with Et$_2$O:MeCN 3:1 to yield protected organoboronic acid 17 as an off-white solid (123 mg, 73%).

A 6 mL vial equipped with a stir bar was charged with protected organoboronic acid 17 (51 mg, 0.106 mmol), THF (1.0 mL), and 1 M aq. NaOH (0.32 mL, 0.32 mmol). The resulting mixture was vigorously stirred for 10 min., then diluted with 0.5 M pH 7 phosphate buffer (2.0 mL) and Et$_2$O (1.0 mL). The phases were separated and the aqueous phase was extracted once with THF:Et$_2$O 1:1 (2.0 mL). The combined organics were dried over MgSO$_4$, filtered, and then concentrated in vacuo. Residual solvent was removed via coevaporation with PhMe, followed by MeCN (2×), and then CH$_2$Cl$_2$ (2×) (bath temperature maintained at <30° C.) to yield the free boronic acid as an off-white solid (39.2 mg, 99%): TLC (EtOAc) R$_f$=0.53, visualized by UV; $^1$H NMR (400 MHz, CDCl$_3$) δ 8.49 (s, 1H), 7.49 (s, 1H), 7.42 (d, J=8 Hz, 1H), 7.26 (m, 1H), 7.17 (s, 1H), 6.84 (s, 1H), 6.49 (d, J=16 Hz, 1H), 6.20 (dq, J=16, 6.4 Hz, 1H), 5.77 (s, 2H), 5.35 (s, 2H), 4.03 (s, 3H), 3.55 (s, 3H), 1.90 (d, J=6.4 Hz, 3H); HRMS (TOF ES+): Calculated for C$_{20}$H$_{22}$O$_6$B (M+H)$^+$ 369.1509. Found 369.1515.

This free boronic acid was then quantitatively transferred as a solution in THF to a 6 mL vial containing 15 (28.5 mg, 0.071 mmol), and the solvent was removed in vacuo. In the glove box, to this vial was added solid K$_2$CO$_3$ (39.2 mg, 0.28 mmol), and a freshly-prepared THF solution (1.06 mL) of 2-(dicyclohexylphosphino)biphenyl (0.008 M) and Pd$_2$dba$_3$ (0.002 M). A stir bar was added and the vial was sealed with a PTFE-lined cap, removed from the glove box, and maintained at 65° C. with stirring for 20 h. The reaction mixture was then allowed to cool to 23° C. and passed through a thin pad of silica gel topped with Celite, eluting with a copious volume of EtOAc. The filtrate was concentrated in vacuo, and the resulting crude product was adsorbed onto Florisil gel from a CH$_2$Cl$_2$ solution. The resulting powder was dry-loaded on top of a silica gel column slurry-packed with hexanes:EtOAc 10:1. The column was eluted with hexanes: EtOAc 10:1→3:1 to yield protected ratanhine 18 as a viscous yellow oil (37.0 mg, 81%).

In an unoptimized procedure, a 6 mL vial equipped with a stir bar was charged with 18 (27 mg, 0.042 mmol), THF (0.3 mL), MeOH (0.6 mL), and concentrated HCl (12 µL). The vial was sealed with a PTFE-lined cap and maintained at 65° C. with stirring for 1 h. The solution was then allowed to cool to 23° C. and diluted with H$_2$O (1 mL), THF (1 mL) and Et$_2$O (2 mL). The phases were separated and the aq. phase was extracted repeatedly with EtOAc. The combined organics were concentrated in vacuo and the resulting crude product was purified by preparative HPLC (Waters SunFire Prep C$_{18}$ OBD 30×150 mm column, Lot #168I161701, 25 mL/min., H$_2$O:MeCN 95:5→5:95 over 20 min., then H$_2$O: MeCN 5:95 for 15 min.; t$_R$=24.84 min with UV detection at 325 and 218 nm) to yield 11 (9.6 mg, 41%) [$^1$H NMR analysis demonstrated that this sample contained a small amount (~5-10%) of an unidentified impurity.] An optimized preparative HPLC method was subsequently developed (Waters SunFire Prep C$_{15}$ OBD 30×150 mm column, Lot #168I161701, 33 mL/min., isochratic H$_2$O:MeCN 20:80: t$_R$=21.72 min with UV detection at 325 and 218 nm) that yielded the pure natural product. $^1$H NMR, $^{13}$C NMR, HRMS, and IR analysis of synthetic 11 were fully consistent with the data reported for the isolated natural product ratanhine, thus confirming the original structure proposed by Arnone and coworkers (Arnone, 1990).

Example 10: Determination of Conformational Rigidity of Protecting Groups

Conformational rigidity of the organic protecting groups of compounds 19 and 193 were determined by the "conformational rigidity test". A sample of 193 (approximately 10 mg) was dissolved in dry de-DMSO and was transferred to a 5 mm NMR tube. The sample was analyzed on a Varian Unity 500 MHz NMR spectrometer. First, a $^1$H-NMR was obtained at 23° C. The sample temperature was then increased incrementally to 30° C., 35° C., 40° C., 45° C., 50° C., 55° C., 60° C. and 70° C. At each temperature the sample shim was optimized, and a $^1$H-NMR spectrum was obtained. Upon cooling to 23° C., a $^1$H-NMR spectrum was obtained which was identical to that previously obtained at this temperature. A sample of 19 (approximately 10 mg) was dissolved in dry ds-DMSO and was transferred to a 5 mm NMR tube. This sample was analyzed in the same way, except that $^1$H-NMR spectra were obtained at 23° C., 60° C., 80° C., 110° C., 150° C. and then again at 23° C.

For 193, twelve peaks in the $^1$H-NMR spectrum corresponding to diastereotopic methylene protons were present from 3.833 to 3.932 at 23° C. As the temperature was raised, these peaks began to coalesce at temperatures as low as 40° C. The peaks had completely coalesced into a single peak at 3.921 by 70° C. Thus, the protecting group of 193 was not conformationally rigid.

For 19, four peaks in the $^1$H-NMR spectrum corresponding to diastereotopic methylene protons were present from 3.992 to 4.236 at 23° C. As the temperature was raised, these peaks remained split into four distinct peaks. No coalescence was observed, even in the spectrum obtained at 150° C. Thus, the protecting group of 19 was conformationally rigid.

Example 11: Synthesis of Protected Haloalkenylboronic Acid 54a (E)-(2-bromoethenyl)dibromoborane (59) was synthesized according to a literature procedure (Hyuga, S., 1987). A subsequent reaction with 59 was conducted in a subdued light environment in an oven-dried 500 mL three-neck round bottom flask equipped with a magnetic stir bar. To a stirred mixture of N-methyliminodiacetic acid (MIDA, 1) (16.93 g, 113.9 mmol, 1.50 eq.) and 2,6-lutidine (17.69 mL, 151.86 mmol, 2.0 eq.) in DMSO (250 mL) at 0° C. under nitrogen was added freshly distilled 59 (21.00 g, 75.93 mmol) dropwise via syringe over 15 min. The reaction mixture was allowed to warm to 23° C. and then stirred at 23° C. for 48 h. The resulting yellow mixture was treated with water (300 mL) and extracted with THF:diethyl ether 1:1 (3×500 mL). The combined organic phases were washed with brine (3×350 mL), dried over anhydrous magnesium sulfate, and concentrated in vacuo to provide a light yellow solid. The crude product was purified by flash chromatography on silica gel (EtOAc:petroleum ether 1:1→EtOAc→EtOAc:MeCN 9:1) to give 54a as a colorless crystalline solid (11.98 g, 45.75 mmol, 60%). Crystals suitable for X-ray crystallography analysis were grown by slow evaporation from ethyl acetate at 23° C. This material was stored under air at 23° C. for one year and six months without decomposition.

Example 12: Synthesis of Bis-Borylated Olefin, and its Use in Selective Cross-Coupling Synthesis of (E)-(2-pinacolethenyl)boronate ester (61)

A solution of the catalyst was prepared as follows: A 20 mL Wheaton vial equipped with a magnetic stir bar was charged with PdCl$_2$(CH$_3$CN)$_2$ (7.9 mg, 0.030 mmol, 1.0 eq.) and 2-dicyclohexylphosphino-2',6'-dimethoxy-1,1'-biphenyl (4d) (38.0 mg, 0.090 mmol, 3.0 eq.). Toluene (3.00 mL) was added and the vial was sealed with a PTFE-lined plastic cap. The resulting mixture was stirred at 23° C. for 30 min yielding a clear yellow Pd/4d catalyst solution.

This catalyst solution was then utilized in the following procedure: A 30 mL Wheaton vial equipped with a magnetic stir bar was charged with 54a (0.262 g, 1.00 mmol, 1.0 eq.), bis(pinacolato)diboron (60) (0.324 g, 1.25 mmol, 1.25 eq.), potassium acetate (0.297 g, 3.00 mmol, 3.0 eq.), toluene (5.0 mL), and catalyst solution (3.0 mL, 3.0 mol % Pd). The vial was sealed with a PTFE-lined plastic cap, and the reaction mixture was stirred for 36 h at 45° C. The resulting heterogeneous mixture was diluted with ethyl acetate (5.0 mL) and filtered through short pad of Celite. Concentration of the filtrate in vacuo provided a light yellow solid. This crude product was purified by flash chromatography on silica gel (EtOAc:Petroleum ether 1:1→EtOAc→EtOAc:MeCN 15:1) to give (E)-(2-pinacolethenyl)boronate ester 61 as a colorless crystalline solid (0.219 g, 0.710 mmol, 71%). Crystals suitable for X-ray crystallography analysis were grown by slow evaporation from EtOAc at 23° C. This material was stored under air at 23° C. for one year and six months without decomposition.

Synthesis of (E,E)-1,3-butadienyl-(4-chloro)boronate (54b)

To a 20 mL I-Chem vial equipped with a stir bar was added 61 (320 mg, 1.05 mmol, 1.0 eq.), finely ground anhydrous K$_3$PO$_4$ (669 mg, 3.15 mmol, 3.0 eq.), PdCl$_2$dppf.CH$_2$Cl$_2$ (26 mg, 0.32 mmol, 3 mol %), and (E)-1-chloro-2-iodoethylene (62) (396 mg, 2.10 mmol, 2.0 eq.). The vial was sealed with a PTFE-lined cap and DMSO (8.4 mL) was added via syringe. The resulting mixture was stirred at 23° C. for 9 h. The reaction was quenched with the addition of 0.5 M pH 7 phosphate buffer (8 mL) and the resulting mixture was extracted with THF:Et$_2$O 1:1 (4×15 mL). The combined organic extracts were washed with brine (25 mL), dried over Na$_2$SO$_4$, and concentrated in vacuo. The resulting residue was diluted with acetone (15 mL) and concentrated onto Florisil®. The resulting powder was dry-loaded on top of a silica gel column and flash chromatography was performed (hexanes:EtOAc 1:1→EtOAc→EtOAc:MeCN 9:1) to yield 54b as a colorless crystalline solid (139 mg, 0.571 mmol, 54%).

Example 13: Synthesis of Bis-Metallated Olefin, and its Use in Selective Cross-Coupling (E,E)-1,3-butadienyl-4-(tributylstannyl)boronate ester (64)

A solution of the catalyst was prepared as follows: To a 4 mL vial equipped with a magnetic stir bar and containing 2-dicyclohexylphosphino-2',6'-dimethoxy-1,1'-biphenyl (4d) (15.2 mg, 0.037 mmol, 2.0 eq.) was added a solution of Pd(OAc)$_2$ in THF (0.095 M, 0.19 mL, 0.018 mmol, 1.0 eq.). The vial was sealed with a PTFE-lined cap and maintained at 23° C. with stirring for 15 min. yielding a clear yellow Pd/4d catalyst solution.

This catalyst solution was then utilized in the following procedure: (E)-2-(tributylstannyl)vinylzinc chloride (63) was prepared according to literature precedent (Pihko, 1999). During the formation of the Negishi reagent 63, to a slurry of 54a (50 mg, 0.191 mmol, 1.0 eq.) in THF (0.2 mL)

at 23° C. was added the catalyst stock solution described above (0.10 mL, 0.0095 mmol Pd, 5 mol % Pd), and the resulting slurry was stirred for 30 min before cooling to 0° C. Negishi reagent 63 was then cannulated into the 54a solution over 5 min. After 2 h at 0° C. the reaction was diluted with EtOAc (10 mL) and then concentrated in vacuo. The resulting red oil was dissolved in EtOAc and filtered through a short pad of silica gel with a copious amount of EtOAc, and the filtrate was concentrated in vacuo. The resulting crude product was purified by flash chromatography on silica gel (EtOAc:hexanes 1:1→EtOAc) to yield 64 as a pale yellow foam (62.2 mg, 0.125 mmol, 66%).

(E,E,E)-(6-chloro)-1,3,5-hexatrienylboronate ester (54c)

A 30 mL Wheaton vial equipped with a magnetic stir bar was charged with $Pd_2(dba)_3$ (0.021 g, 0.023 mmol, 1.5 mol %), $Ph_3As$ (0.014 g, 0.046 mmol, 3.0 mol %), 64 (0.760 g, 1.53 mmol, 1.0 eq.) as a solution in DMF (5.0 mL), and finally (E)-1-chloro-2-iodoethylene (0.575 g, 3.05 mmol, 2.0 eq.). The vial was sealed with a PTFE-lined plastic cap, and the reaction mixture was stirred at 23° C. for 3.5 h. To the resulting deep reddish mixture was then added saturated aqueous $Na_2S_2O_3$ (50 mL) and the resulting mixture was extracted with EtOAc (3×85 mL). The combined organic extracts were washed with brine (3×50 mL), dried over anhydrous magnesium sulfate, and concentrated in vacuo to provide an orange solid. This crude product was purified by flash chromatography on Florisil® (petroleum ether:EtOAc 1:1→EtOAc→EtOAc:MeCN 9:1) to give 54c as a light yellow solid (0.297 g, 1.10 mmol, 72%).

Example 14: Selective Couplings Using Protected Haloalkenylboronic Acid 54a

Suzuki-Miyaura Coupling—Synthesis of (E,E)-1,3-heptadienylboronate ester (68)

A solution of the catalyst was prepared as follows: An oven-dried Wheaton vial equipped with a magnetic stir bar was charged with $Pd(OAc)_2$ (5.60 mg, 0.025 mmol, 1.0 eq.) and 2-dicyclohexylphosphino-2',6'-dimethoxy-1,1'-biphenyl (4d) (20.5 mg, 0.050 mmol, 2.0 eq.). Toluene (3.00 mL) was added and the vial was sealed with a PTFE-lined plastic cap. The resulting mixture was stirred at 23° C. for 45 min. resulting in a yellow Pd/4d catalyst solution (0.00833 N Pd in toluene).

This catalyst solution was then utilized in the following procedure: An oven-dried Wheaton vial equipped with a magnetic stir bar was charged with 54a (0.262 g, 1.00 mmol, 1.0 eq.), (E)-1-pentenylboronic acid 55 (0.171 g, 1.50 mmol, 1.5 eq.), KF (0.116 g, 2.00 mmol, 2.0 eq.), toluene (7.0 mL) and the catalyst solution (1.20 mL, 0.01 mmol, 1.0 mol % Pd). The vial was then sealed with PTFE-lined plastic cap, and the reaction mixture was stirred at 23° C. for 36 h. The resulting heterogeneous light yellow mixture was diluted with acetonitrile (10.0 mL) and filtered through a short pad of Celite. The filtrate was concentrated in vacuo. The crude product was then purified by flash chromatography on silica gel (petroleum ether:EtOAc 1:1→EtOAc→EtOAc:MeCN 9:1) to give 68 as a colorless crystalline solid (0.241 g, 0.959 mmol, 96%).

Suzuki-Miyaura Coupling—Synthesis of (E,E)-1,3-butadienyl-(4-phenyl)boronate ester (80)

A solution of the catalyst was prepared as follows: A 20 mL Wheaton vial equipped with a magnetic stir bar was charged with $Pd(OAc)_2$ (5.60 mg, 0.025 mmol, 1.0 eq.) and 2-dicyclohexylphosphino-2',6'-dimethoxy-1,1'-biphenyl (4d) (20.5 mg, 0.050 mmol, 2.0 eq.). Toluene (3.00 mL) was added and the vial was sealed with a PTFE-lined plastic cap. The resulting mixture was stirred at 23° C. for 45 min. resulting in a yellow Pd/4d catalyst solution (0.00833 N Pd in toluene).

This catalyst solution was then utilized in the following procedure: A 30 mL Wheaton vial equipped with a magnetic stir bar was charged with 54a (0.262 g, 1.00 mmol, 1.0 eq.), trans-2-phenylvinylboronic acid (0.229 g, 1.50 mmol, 1.5 eq.), KF (0.116 g, 2.00 mmol, 2.0 eq.; based on 54a), toluene (7.0 mL), and the catalyst solution (1.20 mL, 0.01 mmol, 1.0 mol % Pd). The vial was then sealed with a PTFE-lined plastic cap, and the reaction mixture was stirred for 24 hr at 23° C. The resulting heterogeneous yellow mixture was diluted with acetonitrile (10.0 mL), filtered through short pad Celite using acetonitrile (100 mL), and concentrated in vacuo. The crude product was purified by flash chromatography on silica gel (EtOAc:Petroleum ether 1:1→EtOAc→EtOAc:MeCN 2:1) to give 80 as a colorless crystalline solid (0.263 g, 0.922 mmol, 92%).

Stille Coupling—Synthesis of (E,E)-1,3-butadienyl-boronate ester (70)

A 30 mL Wheaton vial equipped with a magnetic stir bar was charged with 54a (0.262 g, 1.00 mmol, 1.0 eq.), $Pd_2dba_3$ (0.037 g, 0.040 mmol, 4.0 mol % Pd), $Fur_3P$ (0.021 g, 0.090 mmol, 9.0 mol %), DMF (8.0 mL) and tributyl(vinyl)tin (69) (0.346 mL, 1.15 mmol, 1.15 eq.). The vial was then sealed with a PTFE-lined plastic cap, and the reaction mixture was stirred for 12 h at 45° C. The resulting reddish mixture was diluted with brine (50 mL) and then extracted with ethyl acetate (3×100 mL). The combined organic fractions were dried over anhydrous magnesium sulfate and concentrated in vacuo. The crude product was purified by flash chromatography on silica gel (EtOAc:Petroleum ether 1:1→EtOAc→EtOAc:MeCN 15:1) to give 70 as a colorless crystalline solid (0.190 g, 0.909 mmol, 91%).

Heck Coupling—Synthesis of (E,E)-1,3-butadienyl-(4-methylester)boronate ester (72)

A 30 mL Wheaton vial equipped with a magnetic stir bar was charged with 54a (0.262 g, 1.00 mmol, 1.0 eq.), $PPh_3$ (0.0159 g, 0.060 mmol, 6.0 mol %), $Pd(OAc)_2$ (0.0067 g, 0.030 mmol, 3.0 mol % Pd), $Et_3N$ (0.279 mL, 2.00 mmol, 2.0 eq.; based on 54a), methyl acrylate (71) (0.136 mL, 1.50 mmol, 1.5 eq.), and DMF (7.0 mL). The vial was sealed with a PTFE-lined plastic cap, and the reaction mixture was stirred at 45° C. for 12 h. The resulting mixture was diluted with brine (50 mL) and extracted with ethyl acetate (3×100 mL). The combined organic layers were dried over anhydrous magnesium sulfate and concentrated in vacuo. The crude product was purified by flash chromatography on silica gel (EtOAc:Petroleum ether 1:1→EtOAc→EtOAc:MeCN 15:1) to give 72 as a light yellow solid (0.240 g, 0.898 mmol, 90%).

Sonogashira Coupling—Synthesis of (E)-2-trimethylsilylethyleneboronate ester (74)

A 30 mL Wheaton vial equipped with a magnetic stir bar was charged with 54a (0.262 g, 1.00 mmol, 1.0 eq.), $Pd(PPh_3)_4$ (0.058 g, 0.050 mmol, 5.0 mol %), CuI (0.019 g, 0.100 mmol, 10.0 mol %), piperidine (0.227 mL, 2.30 mmol, 3.0 eq.), THF (5.0 mL), and trimethylsilylacetylene (73) (0.166 mL, 1.15 mmol, 1.5 eq.). The vial was then sealed with a PTFE-lined plastic cap, and the reaction mixture was stirred at 23° C. for 3 h. The resulting mixture was diluted with EtOAc (5.0 mL) and filtered through a short pad of silica gel using EtOAc (100 mL). The filtrate was concentrated in vacuo, and the resulting crude product was purified by flash chromatography on silica gel (EtOAc:Petroleum ether 1:1→EtOAc) to give 74 as a colorless crystalline solid (0.203 g, 0.728 mmol, 73%).

Example 15: Cross-Coupling Between a Trienylchloride and a Vinylboronic Acid A solution of the palladium catalyst was prepared as follows: To a 4 mL vial equipped with a stir bar and containing 2-dicyclohexylphosphino-2',4',6'-tri-iso-propyl-1,1'-biphenyl (4c) (3.0 mg, 0.0063 mmol, 2.0 eq.) in THF (0.577 mL) was added a solution of $Pd(OAc)_2$ in THF (0.00547 M, 0.577 mL, 0.0032 mmol, 1.0 eq.). The vial was sealed with a PTFE-lined cap and stirred at 23° C. for 15 min.

This catalyst solution was then utilized in the following procedure: To a 7 mL vial equipped with a magnetic stir bar and containing 54c (11.0 mg, 0.0408 mmol, 1.0 eq.) was added (E)-1-penten-1-ylboronic acid (55) (7.0 mg, 0.0612 mmol, 1.5 eq.), $Cs_2CO_3$ (39.9 mg, 0.122 mmol, 3.0 eq.), THF (0.835 mL) and the catalyst solution (0.298 mL, 2 mol % Pd). The resulting mixture was then sealed with a PTFE-lined plastic cap and stirred at 45° C. for 24 h. (54c and product 75 were best separated on TLC plates by eluting twice with EtOAc). The resulting heterogeneous mixture was diluted with ethyl acetate (~1.0 mL) and filtered through a thin pad of Florisil® with copious amounts of EtOAc. The crude product was purified by flash chromatography on Florisil® (petroleum ether:EtOAc 1:1→EtOAc→EtOAc:MeCN 15:1) to give (E,E,E,E)-1,3,5,7-undecatetraenylboronate ester 75 as a yellow solid (7.9 mg, 0.0261 mmol, 64%).

Example 16: Total Synthesis of all-Trans-Retinal Using Iterative Suzuki-Miyaura Reactions

First Coupling—Synthesis of tetraenylboronate ester (84)

A solution of the catalyst was prepared as follows: To a 4 mL vial equipped with a stir bar and containing 2-dicyclohexylphosphino-2',6'-dimethoxy-1,1'-biphenyl (4d) (23.1 mg, 0.056 mmol, 2.0 eq.) was added a solution of $Pd(OAc)_2$ in toluene (0.038 M, 0.740 mL, 0.028 mmol, 1.0 eq.). The vial was sealed with a PTFE-lined cap and maintained at 65° C. with stirring for 15 min.

This catalyst solution was then utilized in the following procedure: To a 40 mL I-Chem vial equipped with a magnetic stir bar and containing a solution of 83 in toluene (estimated 0.17 M, 11.5 mL, 1.96 mmol, 1.5 eq.) was added anhydrous $K_3PO_4$ as a finely ground powder (0.833 g, 3.92 mmol, 3.0 eq.), 54a (0.342 g, 1.30 mmol, 1.0 eq.), and the catalyst solution (0.688 mL, 0.026 mmol Pd, 2 mol % Pd). The resulting mixture was sealed with a PTFE-lined cap and stirred at 23° C. for 60 h. The mixture was then filtered through a pad of silica gel with copious amounts of acetonitrile. To the resulting solution was added Florisil® and the solvent was removed in vacuo. The resulting powder was dry-loaded on top of a silica gel column and flash chromatography was performed (hexanes:EtOAc 1:1→EtOAc→EtOAC:MeCN 9:1) to yield protected tetraenylboronate ester 84 as a yellow powder (0.377 g, 1.02 mmol, 78%).

Second Coupling—Synthesis of all-Trans-Retinal (49)

MIDA boronate 84 was converted to its corresponding boronic acid via the following procedure. In a 7 mL Wheaton vial, to a stirred solution of 84 (35.9 mg, 0.101 mmol, 1.0 eq.) in THF (1.44 mL) at 23° C. was added 1 M aq. NaOH (0.30 mL, 0.30 mmol, 3.0 eq.) and the resulting mixture was stirred for 15 min. The reaction was then quenched with the addition of 0.5 M pH 7 phosphate buffer (1.5 mL) and diluted with $Et_2O$ (1.5 mL). The layers were separated and the aqueous layer was extracted with THF:$Et_2O$ 1:1 (3×3 mL). The combined organic layers were dried over $MgSO_4$ and concentrated in vacuo until a small amount of THF (~1 mL) remained, yielding a solution of the boronic acid; TLC: (EtOAc) $R_f$=0.70, visualized by $KMnO_4$.

A solution of the palladium catalyst was prepared as follows: To a 1.5 mL vial equipped with a magnetic stir bar and containing 2-dicyclohexylphosphino-2',6'-dimethoxy-1,1'-biphenyl (4d) (3.6 mg, 0.0088 mmol, 2.0 eq.) was added a solution of $Pd(OAc)_2$ in toluene (0.038 M, 0.115 mL, 0.0044 mmol, 1.0 eq.). The vial was sealed with a PTFE-lined cap and maintained at 65° C. with stirring for 15 min.

This catalyst solution was then utilized in the following procedure: To a 4 mL vial equipped with a magnetic stir bar and containing enal 85 (10 mg, 0.067 mmol, 1.0 eq.) was added the boronic acid (corresponding to boronate 84; see above) as a solution in THF (estimated 0.101 M, 1 mL, 0.101 mmol, 1.5 eq.), anhydrous $K_3PO_4$ as a finely ground powder (42.6 mg, 0.201 mmol, 3.0 eq.), and the catalyst stock solution described above (0.035 mL, 0.0013 mmol Pd, 2 mol % Pd). The resulting mixture was sealed with a PTFE-lined cap and stirred at 23° C. for 5 h. The reaction was then quenched with the addition of saturated aqueous $NaHCO_3$ (2 ml). The layers were separated and the aqueous layer was extracted with $Et_2O$ (3×5 mL). The combined organic layers were dried over $Na_2SO_4$ and concentrated in vacuo. The crude material was purified by flash chromatography (hexanes:EtOAc 32:1) to yield all-trans-retinal (49) as a bright yellow solid (12.6 mg, 0.044 mmol, 66%). $^1$H NMR, $^{13}$C NMR, HRMS, and IR analysis of synthetic 49 were fully consistent with the data reported for the isolated natural product.

Example 17: Synthesis of Half Skeleton of Amphotericin B Macrolide

Synthesis of $BB_4$

A 200 mL recovery flask was charged with diol $CH_3$—CH(OH)—CH($CH_3$)—CH(OH)—CH($CH_3$)—$CH_2$—O—$CH_2$—$C_6H_5$ (Paterson, 2001) (1.18 g, 4.69 mmol, 1.0 eq.), Lipase PS (295 mg, 0.25 mass eq), and hexanes (115 mL) and the resulting slurry was stirred at 50° C. for 15 min. Vinyl acetate (4.33 mL, 47.0 mmol, 10.0 eq) was then added and the reaction mixture was stirred at 50° C. for 40 h. The resulting mixture was cooled to 23° C. and filtered, and the residual enzyme was washed copiously with $Et_2O$. The filtrate was then concentrated in vacuo and the resulting viscous, light yellow oil was purified by flash column chromatography (hexanes:EtOAc 15:1→1:1) to yield monoacetate $CH_3$—CH(OAc)—CH($CH_3$)—CH(OH)—CH($CH_3$)—$CH_2$—O—$CH_2C_6H_5$ as a pale yellow oil (1.05 g, 3.57 mmol, 76%).

To a stirred solution of this monoacetate (5.98 g, 20.31 mmol, 1.0 eq.) in CH$_2$Cl$_2$ (230 mL) at 0° C. was added 2,6-lutidine (7.84 mL, 67.35 mmol, 3.3 eq.) and the resulting solution was cooled to −78° C. Triethylsilyl trifluoromethanesulfonate (7.11 mL, 31.43 mmol, 1.5 eq.) was then added dropwise and the resulting solution was stirred at −78° C. for 1 h. The reaction was then quenched with the addition of saturated aqueous NaHCO$_3$ (115 mL) and allowed to warm to 23° C. The layers were separated and the aqueous layer was extracted with Et$_2$O (3×200 mL). The combined organic extracts were dried over MgSO$_4$ and concentrated in vacuo to give a yellow oil. Purification by flash chromatography (hexanes:EtOAc 7:1→1:1) provided the triethyl silyl ether CH$_3$—CH(OAc)—CH(CH$_3$)—CH(O TES)—CH(CH$_3$)—CH—O—CH$_2$—C$_6$H$_5$ as a yellow oil (7.34 g, 17.96 mmol, 88%).

To a 25 mL three-neck round-bottomed flask equipped with a magnetic stir bar was added palladium black (17.3 mg, 0.163 mmol, 0.6 eq.). Caution: paladium black is pyrophoric and should be maintained under inert atmosphere at all times. For this reaction, EtOH and EtOAc were freshly distilled over activated 4 Å molecular sieves. To this flask was then added via cannula a solution of the triethyl silyl ether (see above; 111.0 mg, 0.271 mmol, 1.0 eq.) in EtOH: EtOAc 2:1 (4.65 mL). The reaction flask was purged with H$_2$ (balloon) and stirred at 23° C. for 25 h under a positive pressure of H$_2$ (balloon). The resulting mixture was then filtered under N$_2$ pressure through a short column of Celite, flushing with copious amounts of EtOH (Pd residue kept under solvent at all times). Purification by flash chromatography (hexanes:EtOAc 12:1→4:1) yielded primary alcohol CH$_3$—CH(OAc)—CH(CH$_3$)—CH(OTES)—CH(CH$_3$)—CH$_2$—OH as a pale yellow oil (79.1 mg, 0.248 mmol, 91%).

To a stirred solution of oxalyl chloride (3.44 mL, 40.1 mmol, 5.0 eq.) in CH$_2$Cl$_2$ (20 mL) at −78° C. was added dropwise DMSO (5.70 mL, 80.2 mmol, 10.0 eq.) and the resulting solution was stirred at −78° C. for 30 min. To the reaction was then added via cannula a solution of the primary alcohol (see above; 2.56 g, 8.02 mmol, 1.0 eq.) in CH$_2$Cl$_2$ (55.7 mL) and the resulting solution was stirred at −78° C. for 1.5 h. Triethylamine (28 mL, 201 mmol, 25.0 eq.) was then added and the resulting mixture was allowed to warm to −15° C. over 40 min. The reaction was then quenched with the addition of saturated aqueous NH$_4$Cl (50 mL). The layers were separated and the aqueous phase was extracted with CH$_2$Cl$_2$ (3×50 mL). The combined organic layers were washed with brine (50 mL), dried over MgSO$_4$, and concentrated in vacuo to yield aldehyde CH$_3$—CH (OAc)—CH(CH$_3$)—CH(OTES)—CH(CH$_3$)—CH=O as a yellow oil (2.36 g, 7.46 mmol, 93%).

To a stirred slurry of CrCl$_2$ (0.204 g, 1.66 mmol, 18.0 eq.) in THF (2 mL) at 23° C. was added a solution of this aldehyde (29.2 mg, 0.0923 mmol, 1.0 eq.) and dichlomethylpinacolboronic ester (Wuts, 1982; Raheem, 2004; 0.117 g, 0.554 mmol, 6.0 eq.) in THF (0.18 mL). A solution of UI (0.149 g, 1.11 mmol, 12.0 eq.) in THF (0.3 mL) was then added and the resulting slurry was stirred at 23° C. for 7 h. The reaction was then poured into ice water (2 mL) and extracted with Et$_2$O (2×5 mL). The combined organic extracts were dried over MgSO$_4$, filtered through Celite, and concentrated in vacuo. The crude material was purified by flash chromatography on Florisil® (hexanes:EtOAc 35:1→3:1) to provide the pinacolboronic ester shown below as a pale yellow oil (25.7 mg, 0.58 mmol, 63%).

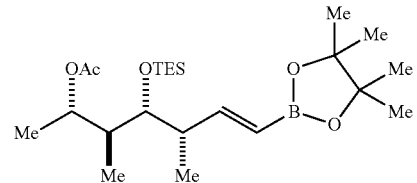

A 15 mL round-bottomed flask equipped with a stir bar was charged with this pinacol boronic ester (126.9 mg, 0.288 mmol, 1.5 eq.). To this flask was then added a solution of (E)-1-chloro-2-iodoethylene (62) (36.2 mg, 0.192 mmol, 1.0 eq.) and Pd(PPh$_3$)$_4$ (16.6 mg, 0.0144 mmol, 5 mol %) as a solution in THF (4.5 mL) followed by 3 M aqueous NaOH (0.192 mL, 0.576 mmol, 2.0 eq.). The resulting mixture was stirred at 23° C. for 17 h and then the reaction was quenched with saturated aqueous NH$_4$Cl (5 mL). The resulting mixture was diluted with diethyl ether (5 mL) and the layers were separated. The aqueous layer was extracted with diethyl ether (3×5 mL) and the combined organic layers were dried over MgSO$_4$ and concentrated in vacuo. Purification of the resulting residue by flash chromatography (hexanes:EtOAc 35:1→5:1 with 1% Et$_3$N (v/v) added to all eluents) provided dienylchloride BB$_4$ as a yellow oil (51.0 mg, 0.136 mmol, 71%).

(E,E,E,E,E)-1,3,5,7,9-decapentenyl-(10-propyl) boronate ester (91)

MIDA boronate 68 (see Example 14) was converted to (E,E)-1,3-heptadienyl boronic acid 90 via the following procedure: To a stirred mixture of 68 (25.6 mg, 0.102 mmol, 1.0 eq.) in THF (1.0 mL) at 23° C. was added 1N NaOH (aq.) (0.306 mL, 0.306 mmol, 3.0 eq.) via syringe. The reaction mixture was stirred at 23° C. for 15 min. The resulting mixture was treated with 1.0 N phosphate buffer solution (pH 7, 0.5 mL) and diluted with Et$_2$O (1.0 mL). The organic layer was separated and aqueous layer was extracted with THF:Et$_2$O 1:1 (3×1.50 mL). The combined organic layers were dried over anhydrous magnesium sulfate. After filtration, the resulting colorless solution was concentrated to ~0.50 mL volume of THF in vacuo. THF (5.0 mL) was added and concentrated again to ~0.25 mL volume of THF in vacuo. The isolated yield of boronic acid 90 was assumed to be 90% based on 68, and a 0.1836 N solution of boronic acid 90 in THF (0.0918 mmol/0.50 mL of THF) was prepared using a 1.0 mL (v/v) volumetric vial. This solution was immediately used in the next reaction without further purification. TLC (EtOAc) R$_f$=0.88, visualized by UV lamp (λ=254 nm) or with KMnO$_4$.

A solution of the catalyst was prepared as follows: A 20 mL Wheaton vial equipped with a magnetic stir bar was charged with Pd(OAc)$_2$ (5.60 mg, 0.025 mmol, 1.0 eq.) and 2-dicyclohexylphosphino-2',4',6'-tri-iso-propyl-1,1'-biphenyl (4c) (24.5 mg, 0.050 mmol, 2.0 eq.). Toluene (3.0 mL) was added and the vial was sealed with a PTFE-lined plastic cap. The resulting mixture was stirred at 23° C. for 1 h to yield a reddish Pd/4c catalyst solution (0.00833 N Pd in toluene).

This catalyst solution was then utilized in the following procedure: A 10 mL Wheaton vial equipped with a magnetic stir bar was charged with BB$_3$ (16.5 mg, 0.0612 mmol, 1.0 eq.), Cs$_2$CO$_3$ (40.0 mg, 0.1224 mmol, 2.0 eq.), the 0.1836 N boronic acid in THF solution (0.0918 mmol, 0.50 mL), and the catalyst solution (0.110 mL, 1.5 mol % Pd). Toluene (1.64 mL) was then added and the vial was sealed with a PTFE-lined plastic cap and stirred for 18 h at 45° C. The resulting deep orange mixture was diluted with EtOAc (5.0 mL) and filtered through a short pad of Florisil®. The filtrate was concentrated in vacuo to provide an orange solid. The crude product was purified by flash chromatography on Florisil® (petroleum ether:EtOAc 1:1→EtOAc→EtOAc: MeCN 9:1) to give 91 as a light yellow solid (8.40 mg, 0.0255 mmol, 42%).

½ of the Amphotericin B Macrolide (92)

A solution of the catalyst was prepared as follows: An oven-dried Wheaton vial equipped with a magnetic stir bar was charged with Pd(OAc)$_2$ (5.60 mg, 0.025 mmol, 1.0 eq.) and 2-dicyclohexylphosphino-2',4',6'-tri-iso-propyl-1,1'-biphenyl (4c) (24.5 mg, 0.050 mmol, 2.0 eq.). Toluene (3.0 mL) was added and the vial was sealed with a PTFE-lined plastic cap. The resulting mixture was stirred at 23° C. for 1 h to yield a reddish Pd/4c catalyst solution (0.00833 N Pd in toluene).

This catalyst solution was then utilized in the following procedure: An oven-dried Wheaton vial equipped with a magnetic stir bar was charged with BB$_4$ (7.0 mg, 0.0187 mmol, 1.0 eq.), 91 (14.0 mg, 0.0421 mmol, 2.25 eq.), the catalyst solution (0.034 mL, 1.5 mol % Pd), and THF (1.50 mL), and the vial was sealed with a PTFE-lined plastic cap. Degassed 1N NaOH (aq.) (0.211 mL, 0.211 mmol, 5.00 eq. based on 91) was added into the vial via syringe. The yellow reaction mixture was stirred for 15 min at 23° C. and then stirred at 45° C. for 16 hr. The resulting heterogeneous deep reddish mixture was diluted with ethyl acetate (5.0 mL) and dried over anhydrous magnesium sulfate. The orange solution was filtered through short pad Florisil® and the filtrate was concentrated in vacuo to provide an orange solid. The crude product was purified by flash chromatography on Florisil® (petroleum ether:EtOAc 60:1) to give 92 as a yellow solid (4.60 mg, 0.0090 mmol, 48%).

Example 18: Synthesis of β-Parinaric Acid (E)-1-Butenylboronic acid (23)

A 150 mL bomb flask equipped with a magnetic stir bar was charged with BH$_3$.SMe$_2$ (1.8 mL, 19.4 mmol, 1.0 eq.) and THF (11 mL). The solution was cooled to 0° C. and (+)-α-pinene (6.3 mL, 39.7 mmol, 2.0 eq.) was added dropwise. The solution was stirred at 0° C. for 10 min then allowed to warm to 23° C. and stirred at 23° C. for 2 h, during which time a white precipitate formed. The solution was then recooled to 0° C. and an excess of 1-butyne was condensed into the reaction via a balloon resulting in a clear, colorless solution. The flask was then sealed with a Teflon screw cap and was stirred at 0° C. for 30 min, warmed to 23° C., and stirred at 23° C. for 1.5 h. The solution was recooled to 0° C. and acetaldehyde (10.4 mL, 185 mmol, 9.5 eq.) was added. The bomb flask was resealed with the Teflon screw cap and the reaction was stirred at 40° C. for 14 h. The reaction was allowed to cool to 23° C. and water (5 mL) was added. After stirring for 3 h at 23° C., the solution was diluted with EtOAc (50 mL), dried over MgSO$_4$, and concentrated in vacuo. The resulting residue was taken up in hexanes (50 mL) and the resulting mixture was extracted with 10% aqueous NaOH (2×10 mL). The combined aqueous extractions were washed with hexanes (2×20 mL) and then acidified to pH 2-3 with concentrated hydrochloric acid. The acidified aqueous layer was then extracted with EtOAc (3×30 mL), and the combined organic extracts were washed with saturated aq. NaHCO$_3$ (50 mL), dried over MgSO$_4$, and concentrated in vacuo to yield the title compound 93 as a colorless solid (0.928 g, 9.3 mmol, 48%).

(E,E,E)-1,3,5-Octatrienylboronate ester (94)

A solution of the palladium catalyst was prepared as follows: To a 4 mL vial equipped with a magnetic stir bar and containing 2-dicyclohexylphosphino-2',4',6'-tri-so-propyl-1,1'-biphenyl (4c) (17.3 mg, 0.036 mmol, 2.0 eq.) was added a solution of Pd(OAc)$_2$ in THF (0.0109 M, 1.664 mL, 0.018 mmol, 1.0 eq.). The vial was sealed with a PTFE-fined cap and stirred at 23° C. for 30 min.

This catalyst solution was then utilized in the following procedure: To a 20 mL I-Chem vial equipped with a stir bar and containing (E)-1-butenylboronic acid (93) (113 mg, 1.13 mmol, 2.0 eq.) was added 54b (138 mg, 0.521 mmol, 1.0 eq.), anhydrous K$_3$PO$_4$ as a finely ground powder (301 mg, 1.42 mmol, 2.5 eq.), THF (7.9 mL), and the catalyst solution (0.780 mL, 0.0085 mmol Pd, 1.5 mol % Pd). The resulting mixture was sealed with a PTFE-lined cap and stirred at 45° C. for 23 h. (54b and product 94 were best separated on TLC plates by eluting three times with hexanes:EtOAc 2:3). The mixture was then filtered through a pad of silica gel with copious amounts of acetonitrile. To the resulting solution was added Florisil® gel and then the solvent was removed in vacuo. The resulting powder was dry-loaded on top of a silica gel column and flash chromatography was performed (Et$_2$O→Et$_2$O:MeCN 4:1) to yield 94 as a yellow powder (120 mg, 0.456 mmol, 88%).

10-iodo-9-decenoic acid (95)

To a suspension of CrCl$_2$ (454 mg, 3.75 mmol, 7.0 eq.) in THF (1.5 mL) at 23° C. was added dropwise a solution of (E)-methyl 10-iododec-9-enoate (100 mg, 0.537 mmol, 1.0 eq.) and iodoform (422 mg, 1.07 mmol, 2.0 eq.) in dioxane (9.2 mL). After stirring for 12 h, the reaction mixture was diluted with Et$_2$O (10 mL) and poured into water (10 mL). The layers were separated and the aqueous layer was extracted with Et$_2$O (3×15 mL). The combined organic extracts were washed with brine (10 mL), dried over MgSO$_4$, and concentrated in vacuo. Purification of the crude product by flash chromatography (hexanes→hexanes: EtOAc 9:1) provided 10-iodo-9-decenoate methyl ester as a yellow oil (105 mg, 0.337 mmol, 63%). $^1$H NMR indicated an E:Z ratio of 10:1.

To a stirred solution of this 10-iodo-9-decenoate methyl ester (51.0 mg, 0.164 mmol, 1.0 eq.) in THF:H$_2$O 3:1 (3.3 mL) was added LiOH (69.0 mg, 1.64 mmol, 10.0 eq.). The reaction was stirred at 50° C. for 4 h before diluting with Et$_2$O (5 mL) and pouring into 1 M aqueous HCl (5 mL). The layers were separated and the aqueous layer was extracted with Et$_2$O (3×5 mL). The combined organic layers were washed with brine (5 mL), dried over Na$_2$SO$_4$, and concentrated in vacuo. Purification of the crude product by flash chromatography (hexanes:EtOAc 5:1→EtOAc) provided 95 as a pale yellow solid (44.0 mg, 0.149 mmol, 91%). $^1$H NMR indicated an E:Z ratio of 10:1.

β-Parinaric Acid (96)

MIDA boronate 94 was converted to its corresponding boronic acid via the following procedure: To a stirred solution of 94 (24.7 mg, 0.094 mmol, 1.0 eq.) in THF (1.34 mL) at 23° C. was added 1 M aq. NaOH (0.28 mL, 0.28 mmol, 3.0 eq.) and the resulting mixture was stirred at 23° C. for 15 min. The reaction was then quenched with the addition of 0.5 M pH 7 phosphate buffer (1.5 mL) and diluted with $Et_2O$ (1.5 mL). The layers were separated and the aqueous layer was extracted with $THF:Et_2O$ 1:1 (3×3 mL). The combined organic layers were dried over $MgSO_4$ and concentrated in vacuo until a small amount of THF (~3.7 mL) remained, yielding a solution of the boronic acid; TLC (EtOAc): $R_f$=0.63, visualized with $KMnO_4$.

A solution of the palladium catalyst was prepared as follows: To a 4 mL vial equipped with a magnetic stir bar and containing 2-dicyclohexylphosphino-2',4',6'-tri-iso-propyl-1,1'-biphenyl ligand (4c) (2.1 mg, 0.0044 mmol, 2.0 eq.) was added a solution of $Pd(OAc)_2$ in THF (0.004 M, 0.545 mL, 0.0022 mmol, 1.0 eq.). The vial was sealed with a PTFE-lined cap and stirred at 23° C. for 30 min.

This catalyst solution was then utilized in the following procedure: To a 20-mL I-Chem vial equipped with a magnetic stir bar and containing 95 (18.5 mg, 0.062 mmol, 1.0 eq.; E:Z 7:1 by $^1H$ NMR) was added the boronic acid corresponding to boronate 94 (see above; 3.7 mL, estimated 0.094 mmol, 1.5 eq.) and the catalyst solution described above (0.31 mL, 0.0013 mmol Pd, 2 mol % Pd). The resulting mixture was sealed with a teflon-lined septum cap and 1 M aqueous NaOH (0.19 mL, 0.190 mmol, 3.0 eq.) was added. The reaction was stirred at 23° C. for 40 min and was then quenched with the addition of saturated aqueous $NH_4Cl$ (3 mL). The layers were separated and the aqueous layer was extracted with $Et_2O$ (3×5 mL). The combined organic extracts were dried over $Na_2SO_4$ and concentrated in vacuo. The resulting crude product was purified by flash chromatography (hexanes:$Et_2O$ 4:1→$Et_2O$) to yield β-parinaric acid 96 as a fluorescent solid (14.8 mg, 0.054 mmol, 86%). $^1H$ NMR indicated a 7:1 mixture of βparinaric acid:9-(Z) parinaric acid (arising from 7:1 E:Z mixture of starting material 95). $^1H$ NMR and $^{13}C$ NMR analysis of synthetic 96 were fully consistent with the data previously reported for β-parinaric acid.

Example 19: In Situ Cross-Coupling of Protected Organoboronic Acids with an Aryl Halide Reaction of 3-methoxyphenyl MIDA-boronate (300)

To a 50 mL round-bottom flask equipped with a stir bar was added 3-methoxyphenylboronic acid (6.591 mmol, 1.002 g) and N-methyliminodiacetic acid (6.27 mmol, 922 mg). To the flask was added toluene (6 mL) and DMSO (2 mL). The flask was fitted with a Dean-Stark trap filled with toluene. The mixture was refluxed for 2.5 h. The solution was concentrated in vacuo (1 Torr, 90-100° C.). The resulting viscous yellow oil was frozen at −78° C., then was placed on a lyopholizer for 12 h. The nearly solid yellow oil was suspended in acetone (3 mL). To the mixture was added $Et_2O$ (6 mL). The mixture was gently agitated. The yellow solution was decanted away from the off-white solid. The solid was placed under vacuum (1 Torr) with heating (app. 80° C.) for 30 min. to afford the desired product as a free-flowing, off-white solid, 1.562 g (95%).

To a 20 mL vial equipped with a teflon-coated stirbar was added 4-bromoacetophenone (0.200 g, 1.005 mmol), 3-methoxyphenyl MIDA-boronate (0.397 g, 1.509 mmol), and sodium hydroxide (0.302 g, 7.550 mmol). The vial was promptly brought into a glove box, and to it was added tetrakis(triphenylphosphine)-palladium(0) (0.023 g, 0.020 mmol) and THF (10 mL). The vial was sealed with a septum cap and taken out of the glove box. H2O (2 mL), degassed for 20 min by sparging with argon, was added to the vial by syringe. The reaction was maintained at 60° C. with vigorous stirring for 24 h. After cooling to room temperature, the reaction was poured into 10 mL 1M aqueous NaOH. The aqueous layer was separated and extracted with ether 3×10 mL. The combined organic fractions were washed with 10 mL saturated aqueous NaHCO3 and 10 mL brine and dried over MgSO4. Solvent was removed in vacuo (~20 Torr and 30° C.) to afford the crude product as a yellow oil. The crude product was purified by column chromatography (50:45:5 hexane/CH2Cl2/EtOAc) to yield a clear colorless liquid which crystallized under vacuum (0.220 g, 97%). This reaction may be run at a total concentration of 0.33 M (2 mL THF, 1 mL H2O) in 96% yield. The concentrated reaction was run in the same size vial. Very efficient stirring may be important, as some components of the reaction are not entirely soluble during the entire course of the reaction.

Reaction of 4-pyridyl MIDA-boronate (302)

To a 50 mL round-bottom flask equipped with a stir bar was added 4-pyridylboronic acid (8.160 mmol, 1.002 g; purple solid as received from Frontier Scientific) and N-methyliminodiacetic acid (7.728 mmol, 1.136 g). To the flask was added toluene (6 mL) and DMSO (8 mL). The flask was fitted with a Dean-Stark trap filled with toluene. The mixture was refluxed for 2 h. As the reaction progressed, a dark solid accumulated on the sides of the flask. This material was not soluble in acetone and dissolved in water to form a blue/purple solution. This material was ascribed to the impurity of the starting material. The mixture was filtered through a thin pad of Celite. The Celite pad was washed with acetone (2×10 mL). The solution was concentrated in vacuo (1 Torr, 90-100° C.). The dark purple residue was suspended in MeCN (5 mL). The mixture was agitated. To the mixture was added $Et_2O$ (10 mL). The mixture was agitated and the purple solution was then decanted away from the purple solid. The solid was washed with Et2O (5 mL). Residual solvent was removed in vacuo to afford the desired product as free-flowing, purple solid, 1.341 g (74%). This material was contaminated with DMSO (estimated 5%), which was removed via trituration, in which the solid material was suspended in MeCN (5 mL), and the suspension was rotated on a rotary evaporator at 40° C. for 5 min. to facilitate mixing. To the mixture was added $Et_2O$ (10 mL), and the mixture was agitated. The solution was decanted away from the purple solid. Residual solvent was removed in vacuo to afford the desired product as free-flowing, purple solid, 1.235 g (68%).

To a 20 mL vial equipped with a teflon-coated stirbar was added 4-bromoacetophenone (0.200 g, 1.005 mmol), 4-pyridyl MIDA-boronate (0.353 g, 1.508 mmol), and K2CO3 (1.043 g, 7.55 mmol). The vial was promptly brought into a glove box, and to it was added tetrakis (triphenylphosphine)palladium(0) (0.024 g, 0.021 mmol) and dioxane (10 mL). The vial was sealed with a septum cap and taken out of the glove box. H2O (2 mL), degassed for 20 min by sparging with argon, was added to the vial by syringe. The reaction was maintained at 100° C. with vigorous stirring for 12 h. After cooling to room temperature, the reaction was poured into 10 mL ether and 10 mL 1M NaOH(aq). The aqueous layer was separated and extracted with ether 3×10 mL. The combined organic fractions were washed with 10 mL sat'd NaHCO3(aq) and 10 mL brine and dried over MgSO4. Solvent was removed in vacuo (~20 Torr and 30° C.) to afford the crude product as a yellow solid. The crude product was purified by column chromatography (100% EtOAc) to yield a colorless crystalline solid (0.188 g, 95%). This reaction can be run at a total concentration of 0.33 M (2 mL dioxane, 1 ml, H2O) in 96% yield. The concentrated reaction was run in the same size vial. Very efficient stirring may be important, as some components of reaction are not entirely soluble during the entire course of the reaction.

Example 20: Preparation of Protected Organoboronic Acids without the Formation of the Corresponding Free Boronic Acid Phenyl-MIDA-Boronate (304)

To a dry 100 mL Schlenk flask equipped with a stir bar, fitted with a rubber septum, and placed under Ar atmosphere, was added THF (25 mL), bromoboenzene (2.0 mL, 19 mmol) and triisopropyl borate (5.3 mL, 23 mmol). The stirred solution was cooled to −78° C. To the solution was added n-BuLi (9.1 mL, 2.5 M, 23 mmol). The pale orange solution was stirred for 15 min. The solution was allowed to warm to room temperature with stirring for 30 min. To the solution was added DMSO (15 mL) and N-methyliminodiacetic acid (8.39 g, 57.1 mmol). The flask was fitted with a distillation apparatus. The mixture was brought to reflux, and as solvent was distilled the distillation pot was periodically charged with toluene to maintain a constant volume. The crude reaction mixture was concentrated in vacuo to afford an off-white solid. To the flask was added acetone (200 mL). The resulting suspension was filtered through a thin pad of celite. The filtrate was concentrated in vacuo. The resulting residue was adsorbed onto Florisil gel. This powder was dry-loaded onto a silica gel column slurry packed in $Et_2O$. The column was flushed with $Et_2O$ (approximately 400 mL), then was eluted with $Et_2O$:MeCN (5:1) to afford 304 as a colorless solid, 3.592 g (81%).

Vinyl-MIDA-Boronate (306)

To a dry 6 mL vial fitted with a septum cap, equipped with a stir bar, and placed under Ar atmosphere was added $BBr_3$ in $CH_2Cl_2$ (1.3 mL, 1.0 M, 1.3 mmol). To the stirred solution was added vinyltrimethylsilane (140 µL, 0.983 mmol). The solution was stirred at room temperature for 13 h. Separately, a dry 25 mL round bottom flask equipped with a stir bar, fitted with a rubber septum, and placed under Ar atm. was charged with sodium N-methyliminodiacetate (478 mg, 2.50 mmol) and DMSO (4 mL). To this stirred suspension was added dropwise by syringe the crude vinylboron dibromide solution. The mixture was stirred for 5 min. The mixture was concentrated in vacuo. The residue was adsorbed onto Florisil gel from an acetone suspension. The resulting powder was dry-loaded onto a silica gel column slurry packed in $Et_2O$. The column was flushed with $Et_2O$ (app. 200 mL), then was eluted with $Et_2O$:MeCN (3:1) to afford 306 as a colorless solid, 88 mg (48%).

Example 21: Three-Component Coupling in a Single Reaction Mixture

Figure 24:
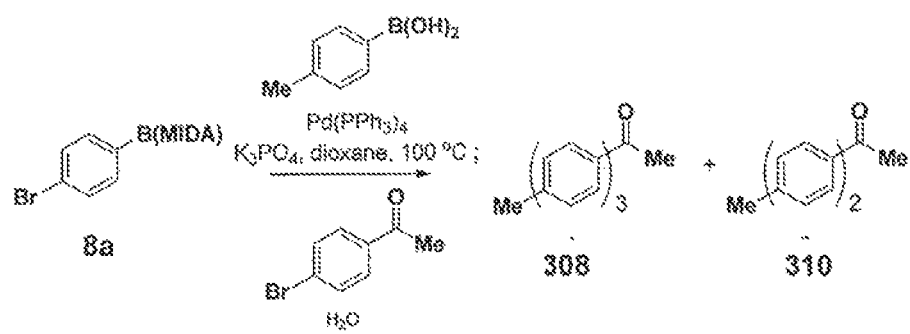
FIG. 24 represents structures and reaction schemes for a cross-coupling reaction of three separate components, carried out in a single reaction mixture.

FIG. 24 shows structures and reaction schemes for a cross-coupling reaction of three separate components, carried out in a single reaction mixture. To a flame-dried 7-mL vial was added 4-bromophenyl-MIDA-boronate (8a, 0.0625 g, 0.200 mmol, 1.00 eq) and p-tolylboronic acid (0.0410 g, 0.3016, 1.50 eq). The vial was capped w/a Kimwipe® and brought immediately into a glovebox, whereupon finely ground potassium phosphate (0.2975 g, 1.40 mmol, 7.00 eq) and tetrakis(triphenylphosphine) palladium(II) (0.0116 g, 0.0100 mmol, 0.05 eq) were added. A magnetic stirbar and dioxane (2.0 mL) were added, and the vial was sealed with a PTFE-lined screwcap. Out of the glovebox, the reaction was maintained with stirring at 100° C. for 12 h. The vial was allowed to cool to 23° C., and again brought into a glovebox, whereupon a 20 µL aliquot was taken for $^1$H-NMR analysis. 4-bromoacetophenone (0.0797 g, 0.400 mmol, 2.0 eq) was added as a solution in dioxane (1.0 mL). The vial was sealed with a PTFE-lined septum screwcap. Out of the glovebox, water (0.60 mL) was added to the vial by syringe. The reaction was maintained with stirring at 100° C. for an additional 12 h.

After cooling to 23° C., the reaction, which consisted of a white suspension in the upper organic phase and a clear colorless lower aqueous phase, was poured into a mixture of 1 M aqueous NaOH (10 mL) and $Et_2O$ (10 mL). The organic phase phase, which included an insoluble white precipitate, was isolated, and the aqueous phase was extracted with $Et_2O$ (3×10 mL). The combined organic fractions were washed with sat'd aq. $NaHCO_3$ (1×0.10 mL) and brine (1×10 mL). The white precipitate was removed by filtration, and the remaining solution was concentrated in vacuo. Analysis by $^1$H NMR revealed the resulting white residue to be a 1:1 mixture of products 308 and 310, Analysis by $^1$H NMR revealed the isolated white precipitate to be exclusively the desired compound 308. $^1$H NMR analysis of the aliquot taken at 12 h indicated complete conversion of 8a.

While various embodiments of the invention have been described, it will be apparent to those of ordinary skill in the art that other embodiments and implementations are possible within the scope of the invention. Accordingly, the invention is not to be restricted except in light of the attached claims and their equivalents.

REFERENCES

1. Barder, T. E., et al. *J. Am. Chem. Soc.* 2005, 127, 4685-4696.
2. Billingsley, K.; Buchwald, S. L. *J. Am. Chem. Soc.* 2007, 129, 3358-3366.
3. Littke, A. F.; Dai, C.; Fu, G. C. *J. Am. Chem. Soc.* 2000, 122, 4020-4028.
4. Miyaura, N.; Suzuki, A. *Chem. Rev.* 1995, 95, 2457-2483.
5. Miyaura et al. *J. Org. Chem.* 60, 7508-7510, 1995,
6. Miyaura et al. *Tet. Lett.* 38, 3447-3450, 1997.
7. Nicolaou, K. C., et al. *Angew. Chem. Int. Ed.* 2005, 44, 4442-4489.
8. Deng, X.; Mayeux. A.; Cai, C. *J. Org. Chem.* 2002, 67, 5279-5283.
9. Hohn, E.; Pietruszka, *J. Adv. Synth. Catal.* 2004, 346, 863-866.
10. Holmes, D., et al. *Org. Lett.* 2006, 8, 1407-1410.
11. Noguchi, H.; Hojo, K.; Suginome, M. *J. Am. Chem. Soc.* 2007, 129, 758-759.
12. Molander, G. A; Ellis. N. *Acc. Chem. Res.* 2007, 40, 275-286.
13. Cammidge, A. N. et al. *Organic Letters* 2006, 8, 4071-4074.
14. Hall, D. G. *Boronic Acids*, Wiley-VCH, Germany, 2005, pp. 3-14.
15. Matteson, D. S. *Stereodirected Synthesis with Organoboranes*, Springer, Berlin, 1995, pp. 1-20.
16. Contreras, R., et al. *J. Organomet. Chem.* 1983, 246, 213-217.

17. Arnone, A. et al. *Gazzetta Chimica Italiana*, 1990, 120, 397.
18. Tyrell, E.; Brookes, P. *Synthesis*, 2003, 4, 469-483.
19. Pangborn, A. B, et al. *Organometallics* 1996, 15, 1518-1520.
20. Stein, A.; Gregor, H. P.; Spoerri, P. E. *J. Am. Chem. Soc.* 1955, 77, 191-192.
21. Dubé, C. E., et al., *Inorg. Chem.*, 2005, 44, 5161-5175.
22. Perner, R. J. et al. *Biorg. Med. Chem. Lett.* 2005, 15, 2803-2807.
23. Friedman, M. R. et al. *J. Mater. Chem.*, 2001, 11, 2759-2772.
24. Albert, J. S, et al. *J. Med. Chem.*, 2002, 45, 3972-3983.
25. Lampe, J. W. et al. *J. Med. Chem.* 2002, 45, 2624-2643.
26. Hoye, T. R.; Eklov, B. M.; Voloshin, M. *Org. Lett.*, 2004, 6, 25867-2570.
27. Still, W. C.; Kahn, M.; Mitra, A., *J. Org. Chem* 1978, 43, 2923-2925.
28. Tsukayama, M. et al. *Heterocycles*, 1997, 45, 1131-1142.
29. Gligorich, K. M, et al. *J. Am. Chem. Soc.* 2006; 128, 2794-2795.
30. De Souza, M. V. N. *Curr. Org. Synth.* 2006, 3, 313-326.
31. Pattenden, G.; Sinclair, D. J. *J. Organomet. Chem.* 2002, 653, 261-268.
32. Hong, B.-C.; Nimje, R. Y. *Curr. Org. Chem.* 2006, 10, 2191-2225.
33. Lhermitte, F. et al. *Synlett* 1996, 377-379.
34. Lipshutz, B. H. et al. *J. Am. Chem. Soc.* 1997, 119, 4555-4556.
35. Pihko, P. M. et al. *Synlett* 1999, 12, 1966-1968.
36. Babudri, F. et al. *Tetrahedron* 1998, 54, 1085-1094.
37. Murakami, M. et al. *Synthesis* 2004, 9, 1522-1526.
38. Denmark, S. E. *J. Am. Chem. Soc.* 2005, 127, 8004-8005.
39. Lipshutz, B. H. et al. *Org. Lett* 2005, 7, 4561-4564.
40. Coleman, R. S. et al. *Org. Lett.* 2005, 7, 2289-2291.
41. Coleman, R. S. et al. *J. Am. Chem. Soc.* 2007, 129, 3826-3827.
42. Organ, M. G. et al. *J. Org. Chem.* 2000, 65, 7959-7970.
43. Antunes, L. M. et al. *Tetrahedron Lett.* 2003, 44, 6805-6808.
44. Organ, M. G. et al. *Tetrahedron* 2004, 60, 9453-9461.
45. Uenishi, J. et al. *Tetrahedron Lett.* 2003, 44, 3093-3096.
46. Romo, D. et al. *J. Am. Chem. Soc.* 1998, 120, 12237-12254.
47. Mancilla, T. et al. *Arkivoc* 2005, 366-376.
48. Nicolaou, K. C. et al. *J. Am. Chem. Soc.* 1987, 109, 2821-2822.
49. Nicolaou, K. C. et al. *J. Am. Chem. Soc.* 1988, 110, 4696-4705.
50. Hyuga, S. et al. *Chem. Lett.* 1987, 1757-1760.
51. Negishi, E. I. et al. *J. Org. Chem.* 1984, 49, 2629-2632.
52. Organ, M. G. et al. *J. Org. Chem.* 2004, 69, 695-700.
53. Zhang, W. et al. *J. Org. Chem.* 2006, 71, 5607.
54. Paterson, I. et al. *J. Am. Chem Soc.* 2001, 123, 9525-9544.
55. Wuts, P. G. M. et al. *J. Organomet. Chem.* 1982, 234, 137-141.
56. Raheem, I. T. et al. *J. Am. Chem. Soc.* 2004, 126, 706-707.
57. Brown, H. C. et al. *Organometallics*, 2, 1316-1319, 1983
58. Brown, *Organometallics*, 3, 1392-1395, 1984.
59. Brown, *J. Org. Chem.* 47, 3808-3810, 1982.
60. Brown, *JACS*, 94, 4370-4371, 1972.
61. Soundararajan et al. *J. Org. Chem.* 55, 2274-2275, 1990.
62. Y. Qin, *JACS* 124, 12672-12673, 2002.
63. Y. Qin, *Macromolecules* 37, 7123-7131, 2004.

What is claimed is:

1. A compound represented by formula (X):

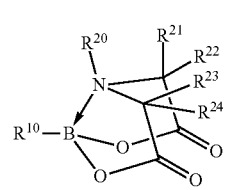

(X)

where $R^{10}$ represents an organic group;
B represents a boron having $sp^3$ hybridization;
$R^{20}$ is an alkyl group; and
$R^{21}$, $R^{22}$, $R^{23}$ and $R^{24}$ independently are selected from the group consisting of hydrogen and an alkyl group;
wherein $R^{10}$ is not selected from the group consisting of —$C_2H_5$, —$C(CH_3)_2CH(CH_3)_2$, cyclopentyl, tetrahydropyranyl, norbornyl, 2,4,4-trimethyl-bicyclo[3.1.1]heptanyl, —$C_6H_5$, —$C_6H_4$—$CH_3$, —$C_6H_4$—CHO, —$C_6H_4$—$OCH_3$, —$C_6H_4$—F, —$C_6H_4$—Cl, —$C_6H_4$—Br, —$C_6H_4$—$CF_3$, and —$C_6H_4$—$NO_2$.

2. The compound of claim 1, wherein $R^{21}$, $R^{22}$, $R^{23}$ and $R^{24}$ are hydrogen.

3. The compound of claim 1, wherein $R^{20}$ is methyl.

4. The compound of claim 1, wherein $R^{10}$ comprises at least one group selected from the group consisting of an alkyl group, a heteroalkyl group, an alkenyl group, a heteroalkenyl group, an aryl group and a heteroaryl group.

5. The compound of claim 4, wherein $R^{21}$, $R^{22}$, $R^{23}$ and $R^{24}$ are hydrogen.

6. The compound of claim 4, wherein $R^{20}$ is methyl.

7. The compound of claim 4, wherein $R^{21}$, $R^{22}$, $R^{23}$ and $R^{24}$ are hydrogen; and $R^{20}$ is methyl.

8. The compound of claim 4, wherein $R^{10}$ comprises at least two alternating carbon-carbon double bonds.

9. The compound of claim 8, wherein $R^{21}$, $R^{22}$, $R^{23}$ and $R^{24}$ are hydrogen.

10. The compound of claim 8, wherein $R^{20}$ is methyl.

11. The compound of claim 8, wherein $R^{21}$, $R^{22}$, $R^{23}$ and $R^{24}$ are hydrogen; and $R^{20}$ is methyl.

12. The compound of claim 1, wherein $R^{10}$ comprises a functional group selected from the group consisting of halogen, pseudohalogen, alcohol, aldehyde, ketone, carboxylic acid, thiol, sulfone, sulfoxide, amine, phosphine, phosphite, phosphate, metal-containing groups, a protected alcohol, a protected carboxylic acid, and a protected amine.

13. The compound of claim 12, wherein $R^{21}$, $R^{22}$, $R^{23}$ and $R^{24}$ are hydrogen.

14. The compound of claim 12, wherein $R^{20}$ is methyl.

15. The compound of claim 12, wherein $R^{21}$, $R^{22}$, $R^{23}$ and $R^{24}$ are hydrogen; and $R^{20}$ is methyl.

16. The compound of claim 1, wherein $R^{10}$ is represented by formula (III):

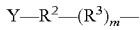

(III);

where Y represents a halogen group or a pseudohalogen group,
$R^2$ represents an aryl group,
$R^3$ comprises at least one group selected from the group consisting of an alkyl group, a heteroalkyl group, an alkenyl group, a heteroalkenyl group, an aryl group and a heteroaryl group, and
m is 0 or 1.

17. The compound of claim 16, wherein $R^{20}$ is methyl.

18. The compound of claim 16, wherein $R^{21}$, $R^{22}$, $R^{23}$ and $R^{24}$ are hydrogen.

19. The compound of claim 16, wherein $R^{21}$, $R^{22}$, $R^{23}$ and $R^{24}$ are hydrogen; and $R^{20}$ is methyl.

\* \* \* \* \*